(12) United States Patent
Monia et al.

(10) Patent No.: US 8,778,900 B2
(45) Date of Patent: Jul. 15, 2014

(54) MODULATION OF EIF4E-BP1 EXPRESSION

(75) Inventors: Brett P. Monia, Encinitas, CA (US);
Sanjay Bhanot, Carlsbad, CA (US);
Kenneth W. Dobie, Del Mar, CA (US);
Ravi Jain, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 1093 days.

(21) Appl. No.: 11/042,768

(22) Filed: Jan. 24, 2005

(65) Prior Publication Data

US 2005/0181400 A1 Aug. 18, 2005

Related U.S. Application Data

(60) Provisional application No. 60/538,751, filed on Jan. 22, 2004.

(51) Int. Cl.
*C07H 21/02* (2006.01)
*C07H 21/04* (2006.01)
*C12Q 1/68* (2006.01)

(52) U.S. Cl.
USPC ........ 514/44 A; 536/23.1; 536/24.1; 536/24.5

(58) Field of Classification Search
None
See application file for complete search history.

(56) References Cited

U.S. PATENT DOCUMENTS

| | | | |
|---|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,828,979 A | 5/1989 | Klevan et al. |
| 4,845,205 A | 7/1989 | Dinh et al. |
| 4,948,882 A | 8/1990 | Ruth |
| 4,981,957 A | 1/1991 | Lebleu et al. |
| 5,023,243 A | 6/1991 | Tullis |
| 5,034,506 A | 7/1991 | Summerton et al. |
| 5,109,124 A | 4/1992 | Ramachandran et al. |
| 5,118,800 A | 6/1992 | Smith et al. |
| 5,118,802 A | 6/1992 | Smith et al. |
| 5,130,205 A | 7/1992 | Vu et al. |
| 5,134,066 A | 7/1992 | Rogers et al. |
| 5,138,045 A | 8/1992 | Cook et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,218,105 A | 6/1993 | Cook et al. |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,512,439 A | 4/1996 | Hornes et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |

(Continued)

FOREIGN PATENT DOCUMENTS

| | | |
|---|---|---|
| WO | WO 98/39352 | 9/1998 |
| WO | WO 99/14226 | 3/1999 |

OTHER PUBLICATIONS

Bennett et al., Biochimica et Biophysica Acta, vol. 1489:19-30, 1999.*

(Continued)

*Primary Examiner* — Sean McGarry

(74) *Attorney, Agent, or Firm* — Isis Pharmaceuticals, Inc. Patent Dept.

(57) ABSTRACT

Compounds, compositions and methods are provided for modulating the expression of eIF4E-BP1. The compositions comprise oligonucleotides, targeted to nucleic acid encoding eIF4E-BP1. Methods of using these compounds for modulation of eIF4E-BP1 expression and for diagnosis and treatment of diseases and conditions associated with expression of eIF4E-BP1 are provided.

43 Claims, No Drawings

(56) References Cited

U.S. PATENT DOCUMENTS

| | | | |
|---|---|---|---|
| 5,541,306 | A | 7/1996 | Agrawal et al. |
| 5,541,307 | A | 7/1996 | Cook et al. |
| 5,541,313 | A | 7/1996 | Ruth |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,555 | A | 10/1996 | Froehler et al. |
| 5,567,811 | A | 10/1996 | Misiura et al. |
| 5,571,799 | A | 11/1996 | Tkachuk et al. |
| 5,576,427 | A | 11/1996 | Cook et al. |
| 5,578,717 | A | 11/1996 | Urdea et al. |
| 5,578,718 | A | 11/1996 | Cook et al. |
| 5,580,731 | A | 12/1996 | Chang et al. |
| 5,587,361 | A | 12/1996 | Cook et al. |
| 5,587,469 | A | 12/1996 | Cook et al. |
| 5,591,584 | A | 1/1997 | Chang et al. |
| 5,591,722 | A | 1/1997 | Montgomery et al. |
| 5,594,121 | A | 1/1997 | Froehler et al. |
| 5,596,086 | A | 1/1997 | Matteucci et al. |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bischofberger et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci et al. |
| 5,658,873 | A | 8/1997 | Bertsch-Frank et al. |
| 5,663,312 | A | 9/1997 | Chaturvedula |
| 5,670,633 | A | 9/1997 | Cook et al. |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,700,920 | A | 12/1997 | Altmann et al. |
| 5,714,331 | A | 2/1998 | Buschardt et al. |
| 5,719,262 | A | 2/1998 | Buchardt et al. |
| 5,721,218 | A | 2/1998 | Froehler |
| 5,763,588 | A | 6/1998 | Matteucci et al. |
| 5,792,608 | A | 8/1998 | Swaminathan et al. |
| 5,792,747 | A | 8/1998 | Schally et al. |
| 5,801,154 | A | 9/1998 | Baracchini et al. |
| 5,830,653 | A | 11/1998 | Froehler et al. |
| 5,998,148 | A * | 12/1999 | Bennett et al. ............... 435/6 |
| 6,005,096 | A | 12/1999 | Matteucci et al. |
| 6,287,860 | B1 | 9/2001 | Monia et al. |
| 6,410,715 | B1 | 6/2002 | Sonenberg et al. |
| 6,582,908 | B2 | 6/2003 | Fodor et al. |
| 2001/0053519 | A1 | 12/2001 | Fodor et al. |
| 2003/0041341 | A1* | 2/2003 | Sonenberg et al. ............ 800/18 |
| 2003/0228597 | A1 | 12/2003 | Cowsert et al. |
| 2007/0031844 | A1* | 2/2007 | Khvorova et al. ............. 435/6 |

OTHER PUBLICATIONS

Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.

Altschul et al., "Basic Local Alignment Search Tool" J. Mol. Biol. (1990) 215:403-410.

Blackshear et al., "Disruption of the Gene Encoding the Mitogen-regulated Translational Modulator PHAS-I in Mice" J. Biol. Chem. (1997) 272:31510-31514.

Branch et al., "A good antisense molecule is hard to find," TIBS (1998) 23:45-50.

Brazma et al., "Gene expression data analysis" FEBS Lett. (2000) 480:17-24.

Brunn et al., "Phosphorylation of the Translational Repressor PHAS-I by the Mammalian Target of Rapamycin" Science (1997) 277:99-101.

Burnett et al., "RAFT1 phosphorylation of the translational regulators p70 S6 kinase and 4E-BP1" PNAS (1998) 95:1432-1437.

Campbell et al., "Nutrients differentially regulate multiple translation factors and their control by insulin" Biochem. J. (1999) 344 Pt 2, 433-441.

Carulli et al., "High Throughput Analysis of Differential Gene Expression" J. Cell. Biochem Suppl. (1998) 30:286-296.

Celis et al., "Gene expression profiling: monitoring transcription and translation products using DNA microarrays and proteomics" FEBS Lett. (2000) 480:2-16.

Chiang et al., "Antisense Oligonucleotides Inhibit Intercellular Adhesion Molecule 1 Expression by Two Distinct Mechanisms" J. Biol. Chem. (1991) 266(27):18162-18171.

Crooke et al., "Basic Principles of Antisense Therapeutics" Antisense Research and Application (1998) Chapter 1:1-50.

Elbashir et al., "RNA interference is mediated by 21- and 22-nucleotide RNAs" Genes. Dev. (2001) 15:188-200.

Elbashir et al., "Duplexes of 21-nucleotide RNAs mediate RNA interference in cultured mammalian cells" Nature (2001) 411:494-498.

Fire et al., "Potent and specific genetic interference by double-stranded RNA in Caenorhabditis elegans" Nature (1998) 391:806-811.

Flynn et al., "Serine 209, Not Serine 53, Is the Major Site of Phosphorylation in Initiation Factor eIF-4E in Serum-treated Chinese Hamster Ovary Cells" J. Biol. Chem (1995) 270(37):21684-21688.

Fuchs et al., "Identification of Differentially Expressed Genes by Mutually Subtracted RNA Fingerprinting" Anal. Biochem. (2000) 286:91-98.

Gingras et al., "Activation of the translational suppressor 4E-BP1 following infection with encephalomyocarditis virus and poliovirus" PNAS (1996) 93:5578-5583.

Going et al., "Molecular Pathology and Future Developments" Eur. J. Cancer (1999) 35:1895-1904.

Graff et al., "Translational control and metastatic progression: Enhanced activity of the mRNA cap-binding protein eIF-4E selectively enhances translation of metastasis-related mRNAs" Clin. Exp. Metastasis (2003) 20:265-273.

Grolleau et al., "Differential Regulation of 4E-BP1 and 4E-BP2, Two Repressors of Translation Initiation, During Human Myeloid Cell Differentiation" Leukemia (2000) 14:1909-1914.

Guo et al., "par-1, a Gene Required for Establishing Polarity in C. elegans Embryos, Encodes a Putative Ser/Thr Kinase That is Asymmetrically Distributed" Cell (1995) 81:611-620.

Hu et al., "Molecular cloning and tissue distribution of PHAS-2, an intracellular target for insulin and growth factors" PNAS (1994) 91:3730-3734.

Jungblut et al., "Protemoics in human disease: Cancer, heart and infectious diseases" Electrophoresis (1999) 20:2100-2110.

Jurecic et al., "Long-distance DD-PCR and cDNA microarrays" Curr. Opin. Microbiol. (2000) 3:316-321.

Larson et al., "Rapid DNA Fingerprinting of Pathogens by Flow Cytometry" Cytometry (2000) 41:203-208.

Larsson et al., "High-throughput protein expression of cDNA products as a tool in functional genomics" J. Biotechnol. (2000) 80:143-157.

Lawrence et al., "PHAS/4E-BPs as regulators of mRNA translation and cell proliferation" Trends. Biochem. Sci. (1997) 22:345-349.

Lin et al., "Control of PHAS-1 by Insulin in 3T3-L1 Adipocytes" J. Biol. Chem. (1995) 270:18531-18538.

Lin et al., "Control of the Translational Regulators PHAS-1 and PHAS-II by Insulin and cAMP in 3T3-L1 Adipocytes" J. Biol. Chem. (1996) 271:30199-30204.

(56) References Cited

OTHER PUBLICATIONS

Madden et al., "Serial analysis of gene expression: from gene discovery to target identification" Drug Discov. Today (2000) 5(9):415-425.
Mader et al., "The Translation Initiation Factor eIF-4E Binds to a Common Motif Shared by the Translation Factor eIF-4y and the Translational Repressors 4E-Binding Proteins" Mol. Cell. Biol. (1995) 15:4990-4997.
Miura et al., "Fluorometric determination of total mRNA with oligo(dT) immobilized on microtiter plates" Clin. Chem. (1996) 42:1758-1764.
Montgomery et al., "RNA as a target of double-stranded RNA-mediated genetic interference in Caneorhabditis elegans" PNAS (1998) 95:15502-15507.
New England Biolabs 1998/99 Catalog (cover page and pp. 121 and 284).
Nielsen et al., "Sequence-Selective Recognition of DNA by Strand Displacement with a Thymine-Substituted Polyamide" Science (1991) 254:1497-1500.
Pause et al., "Insulin-dependent stimulation of protein synthesis by phosphorylation of a regulator of 5'-cap function" Nature (1994) 371:762-767.
Prashar et al., "READS: A Method for Display of 3'-End Fragments of Restriction Enzyme-Digested cDNAs for Analysis of Differential Gene Expression" Methods Enzymol. (1999) 303:258-272.
Ptushkina et al., "Repressor binding to a dorsal regulatory site traps human eIF4E in a high cap-affinity state" Embo J. (1999) 18:4068-4075.
Rau et al., "A Reevaluation of the Cap-binding Protein, eIF4E, as a Rate-limiting Factor for Initiation of Translation in Reticulocyte Lysate" J. Biol. Chem. (1996) 271:8983-8990.
Reynolds et al., "Rational siRNA design for RNA interference" Nature Biotechnology (2004) 22(3):326-330.
Roh et al., "Nutrient-sensing mTOR-medated pathways regulates leptin production in isolated rat adipocytes" Am. J. Physiol. Endocrinol. Metab. (2003) 284:E322-330.
Rosenwald et al., "Upregulation of protein synthesis initiation factor eIF-4E is an early event during colon carcinogenesis" Oncogene (1999) 18:2507-2517.
Rousseau et al., "The eIF4E-binding proteins 1 and 2 are negative regulators of cell growth" Oncogene (1996) 13:2415-2420.
Sanghvi et al., "Heterocyclic Base Modifications in Nucleic Acids and Their Applications in Antisense Oligonucleotides" Antisense Research and Applications (1993) pp. 273-288.
Schalm et al., "Identification of a Conserved Motif Required for mTOR Signaling" Curr. Biol. (2002) 12:632-639.
Scott, "Diagnosis, Prevention, and Intervention for the Metabolic Syndrome" Am. J. Cardiol. (2003) 92(1A):35i-42i.
Strudwick et al., "The emerging roles of translation factor eIF4E in the nucleus" Differentiation (2002) 70:10-22.
Sutcliffe et al., "TOGA: An automated parsing technology for analyzing expression of nearly all genes" PNAS (2000) 97:1976-1981.
Tabara et al., "RNAi in *C.elegans*: Soaking in the Genome Sequence" Science (1998) 282:430-431.
Tee et al., "Caspase Cleavage of Initiation Factor 4E-Binding Protein 1 Yields a Dominant Inhibitor of Cap-Dependent Translation and Reveals a Novel Regulatory Motif" Mol. Cell. Biol. (2002) 22:1674-1683.
Tijsterman et al., "RNA Helicase MUT-14-Dependent Gene Silencing Triggered in *C. elegans* by Short Antisense RNAs" Science (2002) 295:694-697.
Timmons et al., "Ingestion of bacterially expressed dsRNAs can produce specific and potent genetic interference in *Caenorhabditis elegans*" Gene (2001) 263:103-112.
Timmons et al., "Specific interference by ingested dsRNA" Nature (1998) 395:854.
To et al., "Identification of Differential Gene Expression by High Throughput Analysis" Comb. Chem. High Throughput Screen (2000) 3:235-241.
Tsukiyama-Kohara et al., "Tissue Distribution, Genomic Structure, and Chromosome Mapping of Mouse and Human Eukaryotic Initiation Factor 4E-Binding Proteins 1 and 2" Genomices (1996) 38:353-363.
Tuschl et al., "Targeted mRNA degradation by double-stranded RNA in vitro" Genes. Dev. (1999) 13:3191-3197.
Von Manteuffel et al., "4E-BP1 phosphorylation is mediated by the FRAP-p70s6k pathway and is independent of mitogen-activated protein kinase" PNAS (1996) 93:4076-4080.
Wang et al., "The Phosphorylation of Eukaryotic Initiation Factor eIF4E in Response to Phorbol Esters, Cell Stresses, and Cytokines Is Mediated by Distinct MAP Kinase Pathways" J. Biol. Chem. (1998) 273(16):9373-9377.
Waskiewicz et al., "Mitogen-activated protein kinases activate the serine/threonine kinases Mnk1 and Mnk2" Embo J. (1997) 16:1909-1920.
Waskiewicz et al., "Phosphorylation of the Cap-Binding Protein Eukaryotic Translation Initiation Factor 4E by Protein Kinase Mnk1 In Vivo" Mol. Cell Biol. (1999) 19:1871-1880.
Whalen et al., "Phosphorylation of eIF-4E on Serine 209 by Protein Kinase C Is Inhibited by the Translational Repressors, 4E-binding Proteins" J. Biol. Chem. (1996) 271:11831-11837.
Yoshizawa et al., "Modulation of Translation Initiation in Rat Skeletal Muscle and Liver in Response to Food Intake" Biochem. Biophys. Res. Commun. (1997) 240:825-831.
Zhang et al., "PowerBLAST: A New Network Blast Application for Interactive or Automated Sequence Analysis and Annotation" Genome Res. (1997) 7:649-656.

* cited by examiner

SEQUENCE LISTING

```
<160> NUMBER OF SEQ ID NOS: 544

<210> SEQ ID NO 1
<211> LENGTH: 20
<212> TYPE: DNA
<213> ORGANISM: Artificial Sequence
<220> FEATURE:
<223> OTHER INFORMATION: Antisense Compound

<400> SEQUENCE: 1
tccgtcatcg ctcctcaggg                                              20

<210> SEQ ID NO 2
```

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
gtgcgcgcga gcccgaaatc                                              20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
atgcattctg cccccaagga                                              20

<210> SEQ ID NO 4
<211> LENGTH: 895
<212> TYPE: DNA
<213> ORGANISM: H. sapiens
<220> FEATURE:
<221> NAME/KEY: CDS
<222> LOCATION: (65)...(421)

<400> SEQUENCE: 4
gcggagcgag gctggaggcg cgggagggca gcgagaggtt cgcgggtgca gcgcacagga    60 gacc atg tcc ggg ggc agc agc tgc agc cag acc cca agc cgg gcc atc    109
     Met Ser Gly Gly Ser Ser Cys Ser Gln Thr Pro Ser Arg Ala Ile
     1               5                  10                  15 ccc gcc act cgc cgg gtg gtg ctc ggc gac ggc gtg cag ctc ccg ccc    157
Pro Ala Thr Arg Arg Val Val Leu Gly Asp Gly Val Gln Leu Pro Pro
            20                  25                  30 ggg gac tac agc acg acc ccc ggc ggc acg ctc ttc agc acc acc ccg    205
Gly Asp Tyr Ser Thr Thr Pro Gly Gly Thr Leu Phe Ser Thr Thr Pro
        35                  40                  45 gga ggt acc agg atc atc tat gac cgg aaa ttc ctg atg gag tgt cgg    253
Gly Gly Thr Arg Ile Ile Tyr Asp Arg Lys Phe Leu Met Glu Cys Arg
    50                  55                  60 aac tca cct gtg acc aaa aca ccc cca agg gat ctg ccc acc att ccg    301
Asn Ser Pro Val Thr Lys Thr Pro Pro Arg Asp Leu Pro Thr Ile Pro
65                  70                  75 ggg gtc acc agc cct tcc agt gat gag ccc ccc atg gaa gcc agc cag    349
Gly Val Thr Ser Pro Ser Ser Asp Glu Pro Pro Met Glu Ala Ser Gln
80                  85                  90                  95 agc cac ctg cgc aat agc cca gaa gat aag cgg gcg ggc ggt gaa gag    397
Ser His Leu Arg Asn Ser Pro Glu Asp Lys Arg Ala Gly Gly Glu Glu
                100                 105                 110 tca cag ttt gag atg gac att taa agcaccagcc atcgtgtgga gcactaccaa    451
Ser Gln Phe Glu Met Asp Ile
            115 ggggcccctc agggccttcc tgggaggagt cccaccagcc aggccttatg aaagtgatca    511 tactgggcag gcgttggcgt ggggtcggac accccagccc tttctccctc actcagggca    571 cctgcccct cctcttcgtg aacaccagca gatacctcct tgtgcctcca ctgatgcagg    631 agctgccacc ccaaggggag tgaccctgc cagcacaccc tgcagccaag ggccaggaag    691 tggacaagaa cgaaccctc cttccgaatg atcagcagtt ccagcccctc gctgctgggg    751 gcgcaaccac cccttcctta ggttgatgtg cttgggaaag ctccctcccc ctccttcccc    811
```

```
aagagaggaa ataaaagcca ccttcgccct aggaaaaaaa aaaaaaaaaa aaaaaaaaaa        871
aaaaaaaaaa aaaaaaaaaa aaaa                                              895
```

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5

```
ccagcccttc cagtgatgag                                                    20
```

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6

```
atcttctggg ctattgcgca                                                    20
```

<210> SEQ ID NO 7
<211> LENGTH: 22
<212> TYPE: DNA
<213> ORGANISM: Artificial Sequence
<220> FEATURE:
<223> OTHER INFORMATION: PCR Probe

<400> SEQUENCE: 7

```
cccatggaag ccagccagag cc                                                 22
```

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8

```
gaaggtgaag gtcggagtc                                                     19
```

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9

```
gaagatggtg atgggatttc                                                    20
```

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10

```
caagcttccc gttctcagcc                                                    20
```

<210> SEQ ID NO 11
<211> LENGTH: 1915

```
<212> TYPE: DNA
<213> ORGANISM: M. musculus
<220> FEATURE:
<221> NAME/KEY: CDS
<222> LOCATION: (9)...(362)

<400> SEQUENCE: 11 gaggagac atg tcg gcg ggc agc agc tgc agc cag act ccc agc cgg gcc      50
         Met Ser Ala Gly Ser Ser Cys Ser Gln Thr Pro Ser Arg Ala
         1               5                   10 atc ccc act cgc cgg gta gcc ctc ggc gat ggc gtg cag ctc ccg ccc       98
Ile Pro Thr Arg Arg Val Ala Leu Gly Asp Gly Val Gln Leu Pro Pro
15                  20                  25                  30 ggg gac tac agc acc act ccg ggc ggc acg ctc ttc agc acc acc ccg      146
Gly Asp Tyr Ser Thr Thr Pro Gly Gly Thr Leu Phe Ser Thr Thr Pro
                35                  40                  45 gga gga acc agg att atc tat gac cgg aaa ttt ctg atg gag tgt cgg      194
Gly Gly Thr Arg Ile Ile Tyr Asp Arg Lys Phe Leu Met Glu Cys Arg
    50                  55                  60 aac tca cct gtg gcc aaa aca ccc cca aag gac ctg cca gcc att cct      242
Asn Ser Pro Val Ala Lys Thr Pro Pro Lys Asp Leu Pro Ala Ile Pro
65                  70                  75 ggg gtc act agc cct acc agc gat gag cct ccc atg caa gcc aac cag      290
Gly Val Thr Ser Pro Thr Ser Asp Glu Pro Pro Met Gln Ala Asn Gln
        80                  85                  90 agc caa ctg ccc agc agc ccg gaa gat aag cgg gca ggc ggt gaa gag      338
Ser Gln Leu Pro Ser Ser Pro Glu Asp Lys Arg Ala Gly Gly Glu Glu
    95                  100                 105                 110 tca caa ttt gag atg gac att taa gggaccagcc gtaggacgca atgatgcttc    392
Ser Gln Phe Glu Met Asp Ile *
                115 tatgtccccc aaggcccttg ggaggagagc tgcacagcat tcaggcctca taccaggcag   452
acactgggtg tgggtcggcc acccagtcct gctcctcact cagggtgcca gctctgcctt   512
gaattttgtg aacaccagca catacctcct tgtgcctctg tctataccga gctgctactg   572
caggggaatg actctcactc acaccctccc tgcatggagc tccagcgagt ggactcagag   632
gagtctatca gaatgatctg gcaatcctag ccccagcctc cggagcacac ccatctttcc   692
ttaggctggg ttacctggga aagccacact tttacttctt tccctgacag gaaataaaag   752
ccacatttac cctaggcccg cccacagctg ggccctgtct gaactgtttt ccactcgaaa   812
tgacgacatg attactattc tctgtccagt gtttatggtg tgatttccct gtacaatatt   872
ttttaaaaag atttatttta tgtatatgag taatctatct atctgtctgc ctgtctgtct   932
gtctatcatc tttctatcat ctatttatct atctatctat ctatctatct atctgtcttt   992
ctatcatctg tctgtctgtc tatctatcta tctatctatc tatctatcta tctatctatc  1052
tatctatcat ctgtctctat ctatctatct atctatctat ctatctatct atctatctat  1112
ctatctatct atctatctat ctatcaatca tctgtcttgt ctgtctgtct gtctatctat  1172
ctatctatct atctatctat ctatctatct atctatctat ctatctatca tctgtcttgt  1232
ctgtctgtct gtctgtctat tatctatctat atctatctat ctatctatct atctatctat  1292
ctatctatct atctatctat ctatctacta tctatctata tagatggtag tgagccatca  1352
tgtggttgct gggaactgac ctcaggacct ctgctcgctc cgaaaattta tttattatta  1412
tatgttaggt agactgtagc tgtcttcaga tgcaccagaa gagggcatca ggtcccatta  1472
cagatggttg tgagccactt tgtggttgct gggatttgta ctcagaacct tcagaagagc  1532
agtcagtgct cttaactgtt gagccatctc tccagccccc tttacattat catatgtgct  1592
```

-continued

```
tgttatacca gcactctggg tcagcagagc atgccttact gtcaatttac agctgagagg    1652
tctggctgaa gctagccctc tatgggcctg gaccagaacg ctgcaggtct gtaattattt    1712
ttagtagcag caagtgttac ctttgtccag tgagatggtc acctttcctc tgagcctggg    1772
ccagtgtaga gccttcggtc cacatcagaa cagtatgtca atcatctctg tgtgtgctgc    1832 tgtgggggt gcagaggaga taatagataa taggatttta ctgaggtata ccatgtaccc     1892
attaaaaaag gtagcatgaa gtc                                            1915
```

<210> SEQ ID NO 12
<211> LENGTH: 19
<212> TYPE: DNA
<213> ORGANISM: Artificial Sequence
<220> FEATURE:
<223> OTHER INFORMATION: PCR Primer

<400> SEQUENCE: 12

```
ccagcagccc ggaagataa                                                 19
```

<210> SEQ ID NO 13
<211> LENGTH: 23
<212> TYPE: DNA
<213> ORGANISM: Artificial Sequence
<220> FEATURE:
<223> OTHER INFORMATION: PCR Primer

<400> SEQUENCE: 13

```
ggtcccttaa atgtccatct caa                                            23
```

<210> SEQ ID NO 14
<211> LENGTH: 21
<212> TYPE: DNA
<213> ORGANISM: Artificial Sequence
<220> FEATURE:
<223> OTHER INFORMATION: PCR Probe

<400> SEQUENCE: 14

```
cgggcaggcg gtgaagagtc a                                              21
```

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15

```
ggcaaattca acggcacagt                                                20
```

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16

```
gggtctcgct cctggaagat                                                20
```

<210> SEQ ID NO 17
<211> LENGTH: 27
<212> TYPE: DNA
<213> ORGANISM: Artificial Sequence
<220> FEATURE:

<223> OTHER INFORMATION: PCR Probe

<400> SEQUENCE: 17
aaggccgaga atgggaagct tgtcatc    27

<210> SEQ ID NO 18
<211> LENGTH: 843
<212> TYPE: DNA
<213> ORGANISM: R. norvegicus
<220> FEATURE:
<220> FEATURE:
<221> NAME/KEY: CDS
<222> LOCATION: (53)...(406)

<400> SEQUENCE: 18

```
gggccgaggt gccgcggggt tgctggaggg tcgtgggcgg cgtgcaggag ac atg tcg    58
                                                         Met Ser
                                                           1 gcg ggc agc agt tgc agc cag act ccc agc cgg gct atc ccc act cgc   106
Ala Gly Ser Ser Cys Ser Gln Thr Pro Ser Arg Ala Ile Pro Thr Arg
        5                  10                  15 cgc gta gcc ctc ggc gac ggc gtg cag ctc ccg ccc ggg gac tac agc   154
Arg Val Ala Leu Gly Asp Gly Val Gln Leu Pro Pro Gly Asp Tyr Ser
 20                  25                  30 acc acc ccc ggc ggc acg ctc ttc agc acc acc ccg gga gga acc aga   202
Thr Thr Pro Gly Gly Thr Leu Phe Ser Thr Thr Pro Gly Gly Thr Arg
 35                  40                  45                  50 atc atc tat gac cgg aaa ttc ctg atg gag tgt cgg aac tcg cct gtg   250
Ile Ile Tyr Asp Arg Lys Phe Leu Met Glu Cys Arg Asn Ser Pro Val
                 55                  60                  65 gcc aaa aca ccc cca aag gac ctg cca acc att cca ggg gtc act agc   298
Ala Lys Thr Pro Pro Lys Asp Leu Pro Thr Ile Pro Gly Val Thr Ser
             70                  75                  80 cct acc agc gat gag cct ccc atg cag gcc agc cag agc cat ctg cac   346
Pro Thr Ser Asp Glu Pro Pro Met Gln Ala Ser Gln Ser His Leu His
         85                  90                  95 agc agc ccg gaa gat aag cgg gca ggt ggt gaa gag tca cag ttt gag   394
Ser Ser Pro Glu Asp Lys Arg Ala Gly Gly Glu Glu Ser Gln Phe Glu
    100                 105                 110 atg gac att taa gggaccagcc ataggacgca gtgatgcttc tgggcccctg        446
Met Asp Ile
115 gggcccttgg gaggagagcc acagcagtca ggccttgtac ccggcagaca ctgggtgtgg   506 atcggccacc cagtcctgct cctcactcag ggcacctgct ctgccttcca ttttgtgaat   566 accagcacat acctccttgt gcctctgttg atactgagct gctactccag ggtaatgact   626 ctcacctaca ccctccctgc atcaagcgcc agcgagtgga cacagaggag tctgtcggaa   686 tgatctggca attctagccc caacctctgg agcacaccca ccttacctta ggttggggta   746 cctgggaaag ccacccttta cttctttccc tgagaggaaa taaaagccac atttacccta   806 ggcccacagc cgggccctgt ctgaaaaaaa aaaaaaa                            843
```

<210> SEQ ID NO 19
<211> LENGTH: 20
<212> TYPE: DNA
<213> ORGANISM: Artificial Sequence
<220> FEATURE:
<223> OTHER INFORMATION: PCR Primer

<400> SEQUENCE: 19
cctacaccct ccctgcatca    20

<210> SEQ ID NO 20
<211> LENGTH: 20
<212> TYPE: DNA
<213> ORGANISM: Artificial Sequence
<220> FEATURE:
<223> OTHER INFORMATION: PCR Primer

<400> SEQUENCE: 20
tgccagatca ttccgacaga                                           20

<210> SEQ ID NO 21
<211> LENGTH: 22
<212> TYPE: DNA
<213> ORGANISM: Artificial Sequence
<220> FEATURE:
<223> OTHER INFORMATION: PCR Probe

<400> SEQUENCE: 21
cgccagcgag tggacacaga gg                                        22

<210> SEQ ID NO 22
<211> LENGTH: 23
<212> TYPE: DNA
<213> ORGANISM: Artificial Sequence
<220> FEATURE:
<223> OTHER INFORMATION: PCR Primer

<400> SEQUENCE: 22
tgttctagag acagccgcat ctt                                       23

<210> SEQ ID NO 23
<211> LENGTH: 21
<212> TYPE: DNA
<213> ORGANISM: Artificial Sequence
<220> FEATURE:
<223> OTHER INFORMATION: PCR Primer

<400> SEQUENCE: 23
caccgacctt caccatcttg t                                         21

<210> SEQ ID NO 24
<211> LENGTH: 24
<212> TYPE: DNA
<213> ORGANISM: Artificial Sequence
<220> FEATURE:
<223> OTHER INFORMATION: PCR Probe

<400> SEQUENCE: 24
ttgtgcagtg ccagcctcgt ctca                                      24

<210> SEQ ID NO 25
<211> LENGTH: 793
<212> TYPE: DNA
<213> ORGANISM: M. musculus
<220> FEATURE:
<221> NAME/KEY: CDS
<222> LOCATION: (51)...(404)

<400> SEQUENCE: 25
gccgaggtgc cgcggggttg ctggagggtc gtgggcggcg tgcaggagac atg tcg      56
                                                     Met Ser
                                                       1 gcg ggc agc agc tgc agc cag act ccc agc cgg gcc atc ccc act cgc   104
Ala Gly Ser Ser Cys Ser Gln Thr Pro Ser Arg Ala Ile Pro Thr Arg
        5                   10                  15

```
                                                                -continued cgc gta gcc ctc ggc gat ggc gtg cag ctc ccg ccc ggg gac tac agc       152
Arg Val Ala Leu Gly Asp Gly Val Gln Leu Pro Pro Gly Asp Tyr Ser
     20                  25                  30 acc act ccg ggc ggg acg ctc ttc agc acc acc ccg gga gga acc agg       200
Thr Thr Pro Gly Gly Thr Leu Phe Ser Thr Thr Pro Gly Gly Thr Arg
 35                  40                  45                  50 att atc tat gac cgg aaa ttt ctg atg gag tgt cgg aac tca cct gtg       248
Ile Ile Tyr Asp Arg Lys Phe Leu Met Glu Cys Arg Asn Ser Pro Val
                 55                  60                  65 gcc aaa aca ccc cca aag gac ctg cca gcc att cct ggg gtc act agc       296
Ala Lys Thr Pro Pro Lys Asp Leu Pro Ala Ile Pro Gly Val Thr Ser
             70                  75                  80 cct acc agc gat gag cct ccc atg caa gcc agc cag agc caa ctg ccc       344
Pro Thr Ser Asp Glu Pro Pro Met Gln Ala Ser Gln Ser Gln Leu Pro
         85                  90                  95 agc agc ccg gaa gat aag cgg gca ggc ggt gaa gag tca caa ttt gag       392
Ser Ser Pro Glu Asp Lys Arg Ala Gly Gly Glu Glu Ser Gln Phe Glu
    100                 105                 110 atg gac att taa gggaccagcc gtaggacgca atgatgcttc tatgtccccc          444
Met Asp Ile *
115 aaggcccttg ggaggagagc tgcacagcat tcaggcctca taccaggcag acactgggtg     504 tgggtcggcc acccagtcct gctcctcact caggtgccaa gctctgcctt gaattttgtg    564 aacaccagca catacctcct tgtgcctctg tctataccga gctgctactg caggggaatg    624 actctcactc acaccctccc tgcatggagc tccagcgagt ggactcagag gagtctatca    684 gaatgatctg gtaatcctag ccccagcctc cggagcacac ccatctttcc ttaggctggg    744 ttacctggga aagccacact tttacttctt tccctgacag gaaataaaa               793

<210> SEQ ID NO 26
<211> LENGTH: 30652
<212> TYPE: DNA
<213> ORGANISM: H. sapiens
<220> FEATURE:

<400> SEQUENCE: 26
ggagtgccga agggtacacc aggcctgatg tcctaatgca gaaaccgggc cttcctgcag      60
tgggccgggt cagctcggat ctccgcgcgg tcctgagtcg ccgcccccaa cccagccaag     120
gattaattta ggcgagctat cccgcccgcc atccccatat ccgtccctgc cagcgtggcg     180
gggagggacc ccggacggag gggcagtcgc tgcggggcgg cgccagcgcc cgtgcggaag     240
agcccgtgag cagacgggag tgggtcgggg ggcggcgggg gatcccacgt ggaagcagcg     300
tcctggagct gggtgggget gcggcgcgga ctacaaatcc caggggcgtg gggcgggaga    360
ggcggaaggg gcgtcctggg gcggggcggg acggggcgag gcggagcgag gctggaggcg    420
cgggagggca gcgagaggtt cgcgggtgca gcgcacagga gaccatgtcc ggggggcagca   480 gctgcagcca gaccccaagc cgggccatcc ccgccactcg ccgggtggtg ctcggcgacg    540
gcgtgcagct cccgcccggg gactacagca cgaccccggg cggcacgctc ttcagcacca    600
ccccgggagg taggcgcggg cttggcgacg ccgcttgccg gctcctgggc gggcgggagg    660
atcgggaatc gcggattgga ccgggtgtcc aggctcaagg gcgccgtgat tggaaagaac    720
ggaaaagggg catcggagag acagcgaggg tcatggaagt ggccgcccgc ttcccctctg    780
agtgcgtctt ccagacccga gttacaaact gccccgtttg tttcctcttt ctgttaggtg    840
tcagacagct gacacctaac aaaacacgcac gcctccagga cagccacatg ccgagctgtg    900
```

```
ctgcccttg tgggtgttgg gggcgctccc gaagcgggag agggcggagt tagggtggcc    960
cacgatccag gagaggcctg gcctggtgtt tttatgggat gggtattatc tgttgggata   1020
aacgattcct gcagggccct ttttccttcc cgaagcacgc cgagttttgt gttggactcg   1080
cgcgctctga ctgaggttcg gatctggggg tgcttgcctg ctccagcagc gcctcccggg   1140
cacctgtggc acgttcccca tttacgcgag tgggatctcc gcggggggga ccctggcgcc   1200
acggccaggg ctgtgcagaa aaacacgttc ttctgtccgg ggagaggagg aggcaccgtg   1260
tgacctccct gggagaggat gaggaagagg aagctgagct ggcacgggtg ggggggccag   1320
cctcgggctg ccctcaggaa cctggcattc cctcccagcc ccggagcccc agcgcacaga   1380
cgctgatgaa acctacgcgc ctgtttgcat gatgaaataa atcctcgtgg ctctctcctc   1440
ccctctcatt gtcgcactgc ccccaccct ttttgctcct ctcccttcat tctcctccac    1500
gctgctttcc atactactag aaaacgcgac agatcctggc gcttggctag tggcgggcg    1560 ggggccacat gcttattttc tcaggcagct gtcccaccag cagcgagcgc ggccagatcc   1620
gaggtcctct gctgtttgat ccaaaacata cactgttaga acggttaggg atcttgtcca   1680
gccctgccgt cttattctac agagcccggc attgaggccc cagagcttga acacgtgtct   1740
gttgcccatt gtcacaccgt tttcccagat tggacaagaa atagcaacca ggcagagaag   1800
ggagaaatgc ttccttttct attagaaatg agccaaggaa aagctcgcag gggctcttgt   1860
tgccattccc gactcatcct cttttccttg ctgggtcttt tgtagtccat gctgttctcc   1920
tttgtctctg tcacaatggt ctaccaggac aattcctgac aattttggag ttctttcaaa   1980
tgagggtgta agtgtctgct ggatttgttc agggtgggcc ctgaggccgg cctgaaggcg   2040
caggtagccc tttttttgcac tctttattgc tggattgttg ggtcaaattg aagccagga   2100 tactgtttat aggcacttct ggcccgggta ccaaggttca cacctgtaat gccagcattt   2160
tggggagcca aggcaggaga attgcttgag gccaggagtt caagaccagc ctgggcaaca   2220
tagtgagact ccatctctac aaagaaacaa acaaaacaac aacaaaatgt tgtcctagct   2280
actacagagg ctgaggccag aggatcgctt gagcccagga gttggaggct gtagtgagct   2340
atgattgacc actgcactcc agcctgggtg acagagcgag accctatctc taaaataaat   2400
aataaatata aaatataggg acttcaaatc cacttttcac tttgggttgg gaagtgggga   2460
gtgggcaggg ggctgacaga ccacagcaaa tccccttccc tttgaaggtc tttagcagta   2520
gggggagtgg ggaagggact tctgcatcag ggcatagcat atgtttctga gatcactgga   2580
agaagctagc agtgccagga gcctaaagcc agctcactgt ttggtcgtcc agtggagcag   2640
gtacagctca cagtccctaa gccagggaaa cctggctgac ttccactaaa gtcaagcaag   2700
cctggtcggc ctcgattagc caaggtgtgg actcttcctc caaagcccac ctcagcccac   2760
ctctgccagg gcagagaagc caaaatggtc acattgcagc caaaatggtc acaccctttt   2820
gctccagagc agaatactgc ctctcagtct tccaggtgct tgaggataac tgggggcttc   2880
atttaagtgc atattctgat tctgtaggtg ggggtgggaa ctagattcag catttctttc   2940
ttttctttct ttcttttttt ttttttttt tttgagacag ggtctcactc tatcacccag    3000
gctggagtgc agtggcgcaa tctcagctca cagcaacctc cacctcctgg gttcaagcaa   3060
tcctcccacc ccagcctccc caataactgg gacaacaggc atgcaccacc catgcccagc   3120 tgattttgt atttttggt agagacgggg gtttcaccat gttgaccagg ctggtctcaa     3180
actcctggcc tcaagtgatc tgcctgcctc ggccttccag aatgctggga ttacaggcgt   3240
```

```
gagtcaccat gcccggccta gattcagcat ttctaactag ctctgactga ttggtgcaca    3300
taccacactc tgagtactca ggaattagtg aaacataact tccctcacct ttcagatctc    3360
tggagtctag caaaaaaaaa aaaagatgg ctccatccag gtaaactttg atctctaaat     3420
cgtggtgtgg agagccaggc ttttgataga gtgtctgcat ggctgtctgc acctgcttac    3480
ttatagggac tgtcagcttc tcaggaaaaa ccattggagt aagtaccccc cagtcactcc    3540
tgctgggaat ggccctcaag tgattgtccc tggagggaaa gaagcagcag ttgggttgca    3600
ctatctccat tcctatgact ccagtttgct ttcctttttt tttttttttt tttttgaga     3660 tggagtttcg ctttgtcgcc caagctggag tgcaatggtg agatcttggc tcactgcaag    3720
ctccgcctcc cgggttcacg ccattctctt gcctcagcct cccaagtagc tgggactaca    3780
ggcgcccgcg atcaagcccg gctgattttt tgtgttttta gtagagacag ggtttcaccg    3840
tgttagccag gatggtctcg atctcctgac ctcgtgatcc gcctgcattg gcctcccaaa    3900
gtactgggat tacaggcgtg agccactgca cccggccctt ttttgtttt ttcctgaga     3960 cagggtctca tggtgtcacc caggctggag tacagtggca caaacatagc tcactgcagt    4020
ctcaaactcc tgggctcaag tgatcctcct gcctcagcct tgcaagtagc tgggactata    4080
ggcacgtgcc accatgccct gctaattttt ttatttttt atagaggcag ggtctctatg     4140
tattacccag gctggcctca aactcctggg ctcaagcagt cctcccacct cagcctccca    4200
aactgctggg attgtaggca tgagtcacct cacctggcct ccagtttgct ttccatggtc    4260
attaaccatt tgcacactga ggctctgctc tgaggttagc tgtccagagt acttaagata    4320
atttaattgc cgaagggagt gtcatgtatg aatatttgag tctgtggagt cttaaaaata    4380
tccagcgaca ccataaacag ctcattagcc agcagaacct ttgagtgggt cagaagaaa     4440 cttccctca tcaatctcca cattcccagc tccgtgttgc atgtttgact ctgaagccta     4500
tatacaggct tggatggcag ttgtgccaaa gacccgtacc tggataaggt gaatccgagg    4560
tgagcaggta gggctgcagg tgttaatggc accctgtttg gttaagcaaa caaggtctgt    4620
gcccaggaag cttaccttgg agcagctccc aagtctttgg acatgaaaca ggcagtgctg    4680
ggaagaaggg gatgtaggct gggcaccaaa gccagagcac agcccatgtc ctgaggcctt    4740
agtcacatgg agggaagaaa ttattaagga tgggttaaaa gagcttggac attaatgcag    4800
tgagggagaa acgatggacc ctcttctcac atttacctga gcttcctttt aaagtgtttg    4860
aaggagctgg gtgcggtggc tcactcctgt aatcccagct attaggaagg ctgagacagg    4920
aaaattactt gaggccagga gttcaagacc agcctgagca acatagtgag actctgtcgg    4980
tataaattaa ataaataaaa tttttttaaag tgttggaagc attccacact gtgtccctta    5040
ttaaagattt ggtggggggt tcctggtgta gagcactcca aaatccctcc aatccccaga    5100 ctcctttta ttattattat tattttgaga cagagtttcg ctcttgttgc ccaggctgga    5160
gtgcagtggt gcaatcttgg cacactgcaa cctacgcctc ctgggttcaa gtgattctcc    5220
tgcctcagcc tcccaagtag ctgggattac aggcatgtgc caccacaccc ggctaatttt    5280 tgtatttta ttagagacag ggtttcacca tgttagtcag ctggtctca aactcctgac     5340 ctcaggtgat ccaccgcct cagcttccca aagtgctggg attacaggca tgagccacca    5400
cacccggcct tattatttta ttttattta ttttatttt gaggcagtct aactctgtcg     5460
cccaggctag agtgcagtgg catgatttca gctcactgca gcctccacct gccaggttca    5520
ggctgagaca ggagaatccc gggtagctgg gatgacaggc acgcaccacc atgcccagct    5580
aattatttat ttatttattt atttattatt attttcctca agatggagcc ttgctctgtc    5640
```

```
gcccaggctg gagtgcaatg gtgcgatctc ggctcactgc aacctccacc tcctgggttc   5700
aagcaattct cctgcctcag cctcccgaat agctgggttt acaggcgcgc taccacgcct   5760
ggctaatttt ttgtattttt agtagagatg gggtttcacc acgttggcca ggctggtctc   5820
gaactcctga cctcgtgatc cgcccgcctc agcctcccaa agtgctgaca ttacagccat   5880
gagtcaccgc acccggccta ttttatttta tttttgaggc agagtctcat tctgtcaccc   5940
aggctggagt gcagtggcac cgtctcagct cactgcagca tccgcctcct gagttcaagc   6000
aattctcctg cctcggcctc ccgagtagct gggaccacaa acccggctat ttattttgt    6060
agagacaggg tcatgctttg cttctgagtc tgaccctcta gttttttatt atttgaaagg   6120
agaggccagg tgcgatggct cacacctgta atcccagcac tttgggaggc taagcagatc   6180
acctgaggtc aggagttcaa gaccagcttg gccaacatgg tgaaacccca tctctaataa   6240
aaatacaaaa aaaaattagc cgggcctggt ggcaggcgcc tgtaatccca gctacacagg   6300
aggctgaggc acgagactca ctcgaacgat tctgggtgac aagagtgaaa ctccgtctca   6360
aagaaaaaag agagagagtt tgattttttt gcttcctaaa agaccaaaaa agtccttcat   6420
tgccaaatct gaggaaaaag ggtcagcaga gcaataccat atttatccat tgacataaag   6480
tagcgaggca ttttctcata tagacccttta ttttcatgtt ctggaagatg agttaggaag   6540
gcacagcaat attgtttctt cttttttttt taatttgaaa cagggtctca ctttgtcacc   6600
caggctggag tgcagttgca gcctcaacct cctgggctca agcaatcctc ccatctcagc   6660
ctcccaagta gctgggacta caggcatgca ccaccacaac cggctaattt ttgtattttt   6720
tggtagagat gaggtttcgc catgttgccc aggctggcct caaactcctg agctcaagta   6780
atccaccgc cttgacctcc caaagttctg ggattagagg catgctccac tgtgcttggc    6840
ctgggaaggc acagcaatat tgaaaaaaag gaacattgct ttctaaggtg agttttaaaa   6900
aaaaaaaatg ttcagttgtg cacatagatt cttgcctgtg ccaacaaacc catgaaaaac   6960
ctgtttcttt ctggtctgac ttagacccat gcctgggtc tctctccatt atgattcata    7020
gcaatgaat cacacgtttt tgtttacgtg tttgttccct aggttagcca ggaaattttt    7080
tctgagcagt cttactcatc tttgtatcca catgacctaa tgccaggtct agtgtctgga   7140
aggtgaagag ttgaaaagaa tgctggaatg aaagcgttcc cctcaggata acctagtttt   7200
cttattttat ttatttattt attttgaga ctgagtcttg ctctgtcgcc caggctggag    7260
tgcagtggca cgatctcagc tcactgcaac ctccacctcc ctggttcaag tgactctcct   7320
gcctcgcctc ctgagtagct gggattacag gcacgcacca ccacacccag ctaattttg    7380
tattttagt agagacgggg tttaccatgt tggccaggat ggtctcaatc tcctgacctt    7440
gtgatccacc cgcctcgacc tcccaaaatg ctgggattac aggcgtgagc taccatgcct   7500
ggtcaggata acctagtttt cttactgtca ggcctgagtc tccgctggct taatgatgac   7560
gtttaaattt cctttctgt cctttcagtt gcagggtata agtgtttatc tcagaatgtc     7620
ccaggggcag aaactaactt tctctgtttt gatgatgttg tctgtttttt gtttgtttgt   7680
tttttgagac aaagtcttac tctgttgcag gttggagtac agtggcacga tcatgcctca   7740
ctgcagtctc aaccccctga gctcaggtga tccttttgcc tcagcctctc cagtagctgg   7800
gactacaggc acacccacc acgcctggct aatctttaaa ttttttagtag tgacagagtt    7860
ttgtcatgtt gccaggctg gtctggaact cctgggctca agagatccac cacctcagcc    7920
tcccaaaaca ctgggattac aggcgtgagc cactggacca gccagagaat aaccttctct    7980
```

```
gaaccctcct acttatcctc atacagatag tccccgatta tgatggtgtg actacaattt    8040
ttgactttac gatggtatga aagtgatatg tgttcagtag gaattgtact tttaaaaatt    8100
gttttaagac agattcttgg ccggacacgg tggctcatgc ctgtaatccc agcactttgg    8160
gaggctgagg tggtggatc acgaggtcaa gagatagaga ccatcctggc taacatggtg    8220
aaaccccgtc tctactaaaa gtacaaaaaa ttagccaggt gtggtggcac acacctgtac    8280
tcccagctac tcaggaggct gaggcagaag aatcgcttga acccgggaga cagaggttgc    8340
agtgagccga gatcacgcca ctgcactcca gcctgggaga cagagcaaga ctccatctca    8400
aaaaaaaaaa aaaaggcaga gtcttgttct attacctaca ttagagtgca ttggcatgat    8460
atcggctcac tgcaacctcc gcctctcagg ctcaagcaat cctcccacct cagtctctca    8520
agtagctggg attacaggtg tgcgccacca cgcccagcct agaaattgta cattgaattg    8580
tgaattttga tctgtttctg ggccagcgat acgaggtaca tgctctcgag atgctcagca    8640
gggacagtga gctgcagctc ccatttagcc ccacaaacat gaggacaaat ggccagtcac    8700
aagcttgtcc aacccgagac cctcaggcca catgcactct ggacagcttt gaatgaggcc    8760
caatacaagt ccgtaaactt ccttaaaaca ttatgaaatt tctttctttt ttttttttt    8820 ttaagctcag ctggagtgca atggcacaat ctcggctcac tgcaacctct gcctcccagg    8880
ttcaagtgat tctcctgcct cagcctcctg agtagctggg attacaggca cgcgcaacca    8940
cacccagcta attttgtatt tttagtagaa atggtgtttc tctatattgg tcaggctggt    9000
ctcgaactcc caagctcagg tgatccgccc acctcgtcct cccaaagtgt gggattaca    9060 ggcgtgagcc accgcaccca gccagtgtta gtgtatttta tgtgtagtcc aagcaattc    9120 ttcttccagt gtgggcccagg gaagccagaa gattggacag cccactatag agtctatagt    9180
gtgctgtgtt gccaggtggt tttgtccaac tgtaggctaa tgtaagtgtt ctgagcacat    9240
ttaaagtagg gaaggctaag ctataatgtt cagtaggtta ggtgtactaa atactttttt    9300
tttttttttt ttttgagttg gagtgttgct ctgtcgccca ggctggagtg cagtggtgca    9360
atctctgctc actacagcct ctgcctccca ggttcaagcc attctcctgc ctcagcctct    9420
tgagtagctg ggattatagg cgtgtgccac cacacccagc taatttgtat ttttagtaga    9480
gatggggttt caccatgttg gccaggctgg tctcaaactc ctgacctcaa gtgatctgcc    9540
cgcctcagcc tccaaagtg ctggaattac aggcgtgagc cactgcacct ggccctaaat    9600 gcattttga cttaagatat tttctatgta tggtggattt attgggacat acttcatttt    9660
aagtcaagga acatttgtat taaacagtat tgctggtatt tcttgtccca atattaccga    9720
acagggagtg gatgtgactt ttttttcttt ttttaaaaag caaaaacaaa aaacttttaa    9780
cagatagggc ctcacctctg tggcccaggc tggagtgtct atgggctgaa gtacagtggc    9840
gcgatcacca ctcactgtaa cttgagctc ctgggctcaa gcaatcttcc tgcctcagct    9900
tcccgagtag ctgggaccac aggcacatgc taccacacct ggctaatttt tatttttgt    9960 agagatgagg tctatgttgc ccaggctggt cttgaactcc tggcctcagg caatcctcct    10020
gcctcaacct cccaaagcat tgggattaca gatgtgagcc actgcatctg gcaactttt    10080 cttacactga acaagccagt attggggccg ggtctcaga cactgtgact gatgctgttt    10140
atttacctgt ttgcatccag cattgctgac aaggcaagag taagtaactg ctgctcactg    10200
acatttgggt atgcacagca aagggcttca tgtaatctga tggttatgcc catgaaagct    10260
cattaagaga gctcagatac taggcccaga ggatcagggc ttcttaggtg tgcagggaca    10320
cttggtgaaa atggttgtat cagttagcta ttgctatata acaagccatc cccaaacagt    10380
```

```
aactaaacag cagcgatttg ttattgttct ccatcttttg ggttcgttgg gttctttgta   10440
gatcttgctg agcttactca tatggctgca tacagtgtac agctggactg tcctggggtg   10500
gaagctccaa gatggtctta cccatacatc tggggcattg ctggggacag ctggaagcct   10560
gggagttccc tctatcctct tggtctccca acattctgat cactcagtag tctagcttga   10620
gttttattta catggtagtt tccaaggcca cttaaggcct aggctcagaa gtcccataac   10680
atcacttacc aagtattctg tcggtcaaag caagtcacag ggccagccca gattcaggga   10740 gagggaaat acatgcctgt tgttgttgtt gttgttgttg ttgttgttgt tttgagatgg    10800
agtctctctc tgttgcctga gtagctggga ttacaagcgt gcaccaccat gcccagctaa   10860
tttttgtatt tttagtagag acagggtttt accatgttgc ccatgctggt cttgaactcc   10920
tgagctcaag tgatccgccc gcctcggcct cccaaagtgc tgggattaca ggcgtgagcc   10980
atcgcgcctg gccttttttg tttgcttgtt tgtttgacag aatctggctc tgtcgcccag   11040
gccagagtgc agtggcacga tctcagctca ctgcaacctc cgcctcccag gttcaagtga   11100
ttcttttgcc tcagcctccc aagtagctgg gattacaggc acctgccacc acgcccggct   11160 aattttttgta tttttagtag aggcgggggt ctcaccatgt tggccaggct ggtctcgaac   11220
ttctaacctc aggcgatctg cctgccttgg cctcccaaat cactgggatt acaggcatga   11280
tccaccacac ctggcaggaa atatatgcct tttaatgaga gaagctacat gtgcaaacag   11340
gaatgggagg agtggtagga gccacatttt cgaataatcc tccacaaggg ccagacctca   11400
aagaatgggt cttagaggga acgtgctgcc tgtcctgatg tgtggccagc agagccagga   11460
ccaggtgcag aagccgactg gaatcacaac cctgtgaatc agggttaaag aacaaaggac   11520
accttcctaa aggtactgac tcatagatcc catacccctgt tctcacggcc ttatgttcac   11580
ttccacaaag caaaccacac aaggtcgggt gcagtagctc atgcctgtaa tcccagcact   11640
gtgggaagcc aaggcaggtg gattgcttga ggccaggagt tggagaccag cttgggcaac   11700
atagtgagac cctgtctta caaaaaaatt ttaaaactag ccaggtgtag cagcatgcac   11760
ctctagtcct agttacttgg gaagctgagg caggaggatc tctggagccc aggaatttga   11820
ggttacggtg agctatgatc acgccactgc acttcagcct gtgtaataga gtgagaccct   11880
gtctcagaag aaaaaaaaaa agcaaaccac acaggtggcc atgatgctgg accgctaagc   11940
aatctattcc tctttgtgtt gagccttcat tgcaggccat cacccaaacc atctcctctt   12000 cccctccaa gtgtcctgca ggccaggctt tgggaacact cttcagagga gcccacacct    12060
gccctgccct acccagcgct accatgtgaa tatccttaat tttctgtagt acttgcaata   12120
ggatggactc atgtgtctgt gcccagcagt acaaaaccag gcaggaatga gaatagcaga   12180
gggtacagtc gggctcagta ctccctttgg tttggaagtg gacagtgtgg aggtctcttg   12240
ccttaaggag catgtgtgtg agtgtgtggt gtaaacagat ttctctcttc tgcccttctg   12300
aacacaaggg tagagtgggc ctgccttagt ttactatggc tgccataaca aaataccaca   12360
gattgggtgc tttaaacaaa atgaattatc tcctagttct ggaggctgga agtccaagat   12420
caaagtgcca gcagggctgg gttctgaggc ccttctcctt ggcttgcaga tggccacctt   12480
ctccctgtat ctgcacatgg ccttcctct gtctgcatcc aaatctcttc tcataaggac    12540
cccagtcaga ctggattagg gccccaccct aacagcctca ttttaattta atcatcccct   12600
tgaagacttt atctccaaat acagttgcat tccgaggtac tggggttggg cttcaacata   12660
agagttttgg gggcaggccg agcatggtgg ctcatgcctg taatcccagc actttgggag   12720
```

```
gtcaaggcgg gcagatcgct tgaggtcagg agttcaagac cagcctggcc aacatggcaa   12780
aactctgtct ctactgaaaa tacaaaaaat tacccaggcg tggtggcagg tgcctataat   12840
ctcagctacc aggaggaggc tgaggcagga gaatctctgg aaccggggag gcggaggctg   12900
cagtgagtta agatcatgcc actgaactct agtctgggtg acagagtgag acccatctc   12960 acacacacga aaaaagttt tgggagagag tgctattcaa ctattcagct cataacaggg   13020
ccattcccct ttccaactgg gacagcaatc actactgttt gtaatgggag gcatttcaga   13080
aggtcattcc ctattggtaa tgaatttcag ggacagcttc acccataggg tgcatttgaa   13140
gtgtttggga ggaggttaag gaaggggagg agcttggcca gcaatcagaa taattagctc   13200
agctattttg ttctgaaagt ctctgtcaaa gccaattttc ttttcttttc ttttcttttt   13260
cttttttttt tttttttgaga tggagtcttg ctctgttgcc caggctggag tgcagtggtg   13320
cgatcttggc tcactgcaac ctctgcctcc tggattcaag cgattctcct gcctcagcct   13380
cctgagtagc tgggaccacc cggctagttt ttgtattttt agtagagaca gagtttcaac   13440
acgttggcat gctggtctca aactcctgac ctcaggcgat ccacctgcct cggcctccca   13500
aagtgctggg ataacaggtg tgagctatca cacctggcct gaagccaatt ttcaaagaaa   13560
ctgacctatt ccctcccatg ccagggcctc agagggagag gctgccgatc gtccccatct   13620
ggtatccagc agcttcataa gaccccctggc ccctgagaaa tgttgggatc ttggttctct   13680
ttgtggaggt cagcggttgc ggggcagagg taaagaaaag tcttggactg agtgtgctct   13740
gcatctctca ccaggatttc caccccggca gttctgtcct gcttgttaaa tagaccatcc   13800
agccagaaaa gccacccaga cacatgtgat tcctccctgg actgtgtggc gaggagggag   13860
ggaagaccga gattctggca tgtcggcgta tttacctcca ggttaacagg gagctgcctc   13920
agagctggag ttcagattgt ccagggtgtt ttgctcactg gctgttggct tggatctgag   13980
cagaagcatt tggacctccc ccaccccggc cctgttgtga aatgctctcc ctctccctgg   14040
aatgggaaca gcagttctag gaattccatc ctcgtactct cactaagcct cacgtcccca   14100
catccaatgg aagaatgctt ctgccaaagg aaccccaggg gaaagtgagg gccatgcgcg   14160
gctcagttta cagaagtcct atccagccgc agagtatggg cactggaggg ctatggggaa   14220
gcgctcaagg cagggaacat cctgttctga caagcaccca gaagtctaag acctcctaat   14280
ttttccagct gagagtgtta gctaaggggt ggtagcctgg tctgccttac taattttatt   14340
ttattttgta gagacagggt ctcactctat cacccaggct agagtacagt agcatgatcc   14400
cagctcactg cagcctcaaa ctcctgggct aaagcgatcc tcctgcctca gcctctggag   14460
tagctgggat cataggcgca tgccatcatg ccaggctact ttttaaattt tttgtagaga   14520
tgggggtctc actgtgttgc ccaggctggt ctcaaactcc tggcctcaag caattctcat   14580
gccttggcct cccaaagcat tgtgattgca ggcatgatcc agccttgcta atttttaaaca   14640 gtaggaggca tttaggattg gagtcgaggt gggttaggtt ggcctctgga cggctgtgag   14700
gggacagcct ttctgggcct cagtttcctc ttctgcaagg tgaagctcct gcgtggggag   14760
ttgtaagggg gaataagacc tagcacgtca ggctgtgagc acagaccgga ggggatgaca   14820
gatggcaatg attgctgtat gcacctcgcc cgaaaatcta agccttcatt catgcagcac   14880
tccaatgctc cttggcctcc aaaaatgctt cctgttcccg gcttgtgaca tctttctttg   14940
gttgcgtatg ttctcccaag tgattttctc tttaacagca attatgtgag tgtcacttta   15000
ttctcacaca aagaatcttg atgttcttta ttttattaa tcttcacgat actccctga   15060 ggtgtggatt ttgttattcc ctccctctta taactgagga atgaaagtgc aacttggagt   15120
```

```
tcagggactg acatgtggca agctcaggtt tgagcccaga acatctgcct ccaagcacta   15180
tgctatttgt acattaagta cctgccaaca aggagatcct aaaaataaat ggcacgtgcc   15240
tggtgctttc aaaatagttt gaatgagcct agtacaatgc cgttgtttta caggtgagga   15300
aactagaacc taagggaatg tctctatggc tttatttatt gtaatcccag aactttggga   15360
ggccgaggtg gggggattgc ttgagcccac aagttcaaga ccagtcaagg caacatgaca   15420
aaaccttgtc tacaaaaaaa aaaaaaaaat tagctgggca tggtggtgca tgcctgtagt   15480
cccagctact tgggaggctg aggcaagagg ctcacttgag cccaggaggc agaagttgca   15540
gtaagccaag atcacactat tgttctccag cctgggcagc agaccgagac tctatctcaa   15600
aaaataataa taatgataat taattaatag aaatatttcc ttactttttt tagagacaga   15660
tcttgttctg tctcccagac taccgtgcag tggtaaaatt gtagttccct acaaccttga   15720
attctgggtt caagccatcc tcctgcctca gcctcctaag tagctgggac tgcagacatg   15780
caccacaaca cctgactaat ttttttttg tttgtttgag acagagtctt gctctgtcac   15840
ccaagctgga gtgcaatggt gcgattttgg ctcactgcaa cctctgcctg ggttcaagca   15900
atcctcctgc ctcagcctcc caagtagctg ggattacagg cgtctgccac cacgcccagc   15960 taattttttgt atgtttaata gagacagggt ttcaccatgt tggtcaggct ggtctcaaac   16020
tcctgacctc aagtgatcca cctgccttgg cctcccagtg tgctgggatt acaggcgtga   16080
gcttccccac ccggcctaca cctggctaat ttttaacttc ttttgtagag atgggatcgt   16140
gctttgttac ccatgctggt cttgaacccc cccattgctt tatatattga aagcaaacta   16200
ctgtcaccac aaagcatgcc ttgaaaaaaa aatatcattc ctatatttgg tgcacatttg   16260
gagtttaaaa tcctgaagga tactggctaa caaacatgct gaagtttatg atggttcttg   16320
gtttccgtgg gcctaaaaag gagggaggac accctcaccc tgtcccttcc aagtgtctct   16380
cctgagttgc ttacctgtcc tctgatttat ccctgctttg actgataatt ggttgctggt   16440
atggatggaa ctgaataaat ggtgaaatta tgtcacctgg accctgcagg tcatgataat   16500
aactagaatt gtatggggct tacattgtgt cagccactgt tcaaatccac acagtaatcc   16560
tatgaagttg gcactaccat catcatcatc atcattgtcg tcgccaatct ggagaagcag   16620
aaactgaggc acaaagattt taagtcataa cttcccagga gtcatgagag ctagcaaatg   16680
gaatgacaga gctgggtttc caaaggattt caggtagaat gagcctcagt tatttgtcccc   16740 agatagttca agaccgaacc ttgaactcta cccccagcac acaacgggct ggatcccagc   16800
tacacaaatg gtttgaggtg tagggtgct cctctcttct tcccttgccc tgctgggagg   16860
cagggttctg ggtttccctg ctctgcatct ctgggttggc aatcaaggtc agccttagct   16920
cacctccctc accctcggg cactggagaa ctggggtgag atggatgttt ctctgggccg   16980
ggggtttagg gtcaggctgc ttggaagcag gaagatggag gacttgggat ctgtgtccct   17040
tggtgatctc ctcttacgcc tgtctgtgga cttcacacac ttggctgtaa tcacttgttt   17100
acgggtcttt ctcgactaaa ttacataagg tttggatcta ggcactttca ctacatctga   17160 ctttttaaa tccctagcac ctcgcatggt gctagtacaa agtagaggtt cagtgagtaa   17220
gtaaatgaga ccagcacacc tactttcagg aaaaaaggat tgagcaaaga ccggcaaata   17280
tgtgggtaag gattaacatt tttgtccctg gattgcagta gtctctatac ttgaatacag   17340
ttcatgggag ttaaggtgta gtgtaggggtt ttgggttttg ttttttgtttt tttttttgag   17400 acagagtctc actctcttgc ccagggtgga atgcagtgat gcgatctcaa ctcactgcaa   17460
```

```
catctgcctc ccgggttcaa gcagttttcc tgcctcagcc tcccaagtag ctgggattac   17520
aggcacatgc caccacgccc agctaatttt tgtatttttta gtaaagacag ggttttgcca   17580
tgttggccag gctggtctcg aactcctgac ctcaggtgat ccacccacct tggcctccca   17640
aagcactgag attacaggca tgagccactg cgcccagcct gaatcacttt tttgataaat   17700 gaggttttttt ttatttctgt attttctctc ttcctctccc ctcattgtcc caataaaatt   17760
acatttcaaa gttttaaaaa tccagccagg tgcagtggca cacacctgta atcccagctc   17820
ctcaggaggc tgaggcagga ggatcacttg agcccagaag tttgagtcta gcctgggcaa   17880
catagcaaga ttctgtcttt aaggaaaaca aaaacaaaa acaggctggg tgcagtggat   17940
cacttgagcc caggagttcc agcccaccct aggcaacatg gtaaaaccct gtctctacaa   18000
aaaagtatat acaaaaatta gctgggtgtg gtgacacttg cctgtagtcc cagctactca   18060
ggaagctgag gtgggaggat cacctgagcc caggaggtcc aaggttgcag tgagccatga   18120
tggcaccact gcactccagc ctgagtgaca gagcaagacc ctgtttcaaa aaaaaaaaa   18180 tttaaactaa aattaaaagt aaacatttgt tgttttatt atgatgattc ttgagccaag   18240
tactatctat aataatagca tttccacttt tatatatata tatttttaa aaaagcaga   18300 gttaataatt gctttgtttt aaaaatgtgc ttagttttca tttaggtttt cccaaacctt   18360
ccagaagctc tctaaaatgc ctcacagtaa ggtcttgcac acagttggac ttctagattt   18420
atctgcccat ttttccctc tctcctaaac taagacaaga tttggagtaa cagtttggct   18480
gctccagccc tgccacacaa ctgtcaatgt ggggttccct gaagccctag tctttctata   18540
attttggcag aacacatctt actgtattct ttctgaaatg tctctatggc caggtgcagt   18600
ggctcacacc tgtaatccca gcactttggg aggctgaggc aggaggatca tttgaaacca   18660
ggggtttgag accagcctgg gtaacatagc gagaccctgt ctccaaaaat aaaatttgat   18720
ttaatttaaa gaaaaagag aggccgggta cggtggctca tgcctgtaat ccctgcactt   18780
tgggaggccg agacgggtgg atcacctgag gtcaggaatt caagaccagc ctcgacatgt   18840
agaaacccca tctctactaa aaatacaaaa ttagccgggc ttggtggtgc aggcctgtaa   18900
tcccagctac tcgggaggct gaggcaggag aattgcttga atctgggagg cggaggttgc   18960
agtgagccga gattgcgcca ttgcactcca tcctgggcaa caagagcgaa actccgtctc   19020 aaaaaaaaa aaaagaaaag aaaagaaaaa agagaagtat ctctgttata cttttacttg   19080
atttgtgttt ggcagggat aagatgcagg ttgaagtgaa ttttctgtca gattgtgaag   19140
gcgtcaaggc accgtttgca ggcttccagt cttgccattt aagacatttt acgcccttct   19200
cattccctgt ccttgtgtat acctgaaaat cctataaagg attttctctt tatcgccagt   19260
attgtgaatt tcacaatgat gttaactgag tgttttgaat tcattgcact acttactgaa   19320
aggggagctt caatttcaag acatctcttt caattcagga aaatttccgt cttctttttt   19380
tttttttttt tcttgagaca ggttctcgct ctgtccccca ggccggagtg cagtagcgtg   19440
atctcaactc actgcaacct ccaccttgtg ggtttaagca atcctcctgc ctcagcctcc   19500
cgagtagctg ggattataga cacacaccac catgcctggc taattttttgt attttttagta   19560 gagatgggtt tcaccatgt tgtctaggct ggtcttaaac tcttgatctc aagtgatcta   19620
cccacctcgg cctcccaaag tgctgggatt acaggcgtga gccaccacac caggcctttc   19680
ttcatatttt taaagtaaat tccctttat tagtttctct tttctccttc tggacttcct   19740
gccatccaat attggacccc taatttatta tcttttgcc tattgttcat ctctttgtcc   19800
tttttctttt ttcttttttt tttgagatgg aatgtttctc tgtccccagg cccggagtgc   19860
```

```
agtggcacaa tctcggctca ctgcagcctc cgcctcctgg gttcaagcgg ttctcgtgcc    19920
tcagcctcct gaatagctgg actacaggtg tgcaccacca cacccagcta atgttttgta    19980
tttttagtag agacggggtt tcaccatgtt ggccaggctg tcttgaact  cctgacctca    20040
tgtgatccac ccgcctcagc ctcccaaagt gttggggttg tatacgtgaa ccactgcacc    20100
cggcctcttt tgttttcctt taagattttc tgcttccttt attacctgtt tcctcctgtt    20160
gatttgctta gatctcgcct taaatgctac aagcctttct cagaaatgtg tgggaacatt    20220
tgactggttg gttttttaaa tttttaaaa  ttagttttt  gacacagggt ttcactctgt    20280
caatcaaact ggagtatagt ggtgcagtct tagctcactg cagccttgga cctcctgggc    20340
tctggtgatc ctcccacctc tgcctcctgg gtagctggaa ctacagacgt gtgccaccac    20400
gcttggctaa ttttgtctt  ttttgtaaag acagggtttt accgtgttgc tcaggctggt    20460
ctcaaactcc tgggctcaag caatccgcct gcctcggtct tttctttctt tctttctttt    20520
ttgaaagaca gggtctcgct ctttcgctca ggctacggtg caatgtcatg attatagctc    20580
actgcagcct caacttccta ggctcaactg atcctcccac ctcagccttc cagagtgttg    20640
ggattactta caggtgtgaa ccactgcacc gggcctggct gttttattt  aagggtgggg    20700
aactcaggag ctgaccagga gtcccttgtg tggcccagag actgatgggt tccatctggt    20760
ggctagctgg ttttattcac tgtggacccc catgccacaa tcagtttctg taggtcttta    20820
tcttcactct ttattctgaa gcaggggaga ggagagggct taaggctcac cattcaggag    20880
gtcaacttta atttctctgt cacccctctc cttggggcaa gggacacctg cacccctct    20940
ggtaagtttg cttaagagag taaacctcag ggcagctgct agatgctggt aagaacctgg    21000
ggtttccatt ttccatacag acttccaagc agtctccctg ttatcagccc ccatccccag    21060
attccatgct gtgcctaatt cctgaacctt cctggggttc tctggggcaa acggagaact    21120
tgctccaccc ccacctccct gcatttcagt gtcacccgct tcctcccat  gagatcgttg    21180
accgctcctg tacttgcctc tgtctttacc tgttgtgatt tggggtgaca gttggagctc    21240
tccctgcatc caggttggag aacgtgcttg tacttctcat tcttggtgtt tggcatgact    21300
tttgagagga gtaggagaaa aatgtcatgg ctctgccatc ttgaagtcac tttgatcctc    21360
aaaagtactt catactcttt gtagtgacct agtggaggtg ggtcatttac cccagtgtac    21420
agaggggtcc aagacaggcc tgctgatgac ataggacctc agttaaagag gttttgtttt    21480
ccttttattt atatttttt  ttattttttt gtgacagagt cgtgctctgt ctcccaggct    21540
ggagtgcagt ggcacgatct cggctcactg caacccccgc ctcccaggtt caagtgattc    21600
tcctgcctca gcctcctgag tagctaggat taggtgtgtg ccaccatgcc cggctaattt    21660
ttgtgttttt aatagaggcg ggatttcgcc atgttggcca ggctggtctc gaactcctga    21720
cctcaggtga tctgcctgcc tcggcctccc aaagtgctgg gattacaggc gtgagccact    21780
gcgcccagcc tgttttactt ttaaagatga ggtctgctg  tgttggccaa gctggtctgg    21840
aactcccagc ctcaagtgat cctccaacct tggcctccca aactgttggg atttacagat    21900
gtgagtcact gcgcccagcc gtagccccca cctttggcta aagagtttta tgtggaggcc    21960
accctagcgt gatgccactc cacctgctga acacacacac aggtttctgt cagaccacac    22020
ctgaccagca gccctgaagg gaccttggca tccatcccac ccactcgtgt ttccatttcc    22080
tgaccttgta catgggccaa gtgtcccag  caccaagtag ctctgcagca ggtgtcttca    22140
gccaggcttt aaggtttgtc tttttttttt tttagacagg gtctcgctct gtctcccaga    22200
```

-continued

```
ctggagtcca atggtgcaac cactgctcac cacagcctca atctctcagg ctcaagcgat    22260
cctcccatct cagcctcccg cgtagctagg actccaagcg catgccacca tgcctggtta    22320
attttttaaa aattttagta ggccaggtgc agtggctcat gcctgtaatc ccagcacttt    22380
gggaggccga ggcaggcgga tcacctgagg tcaggaactc aagacctgcc tggccaacat    22440
ggcaaaaccc tgtctccact gaaactacaa aaattagcca ggcatctgta atcccagcta    22500
cttgggaggc tgaggcaagg agaattgctt gaacccagga ggcagaggtt acagtgagcc    22560
gagatcgcac cactgcactc cagcctgggc aacagaatga gactccatct caaaaaaaaa    22620
aaaaaaattg tagataaggt cttgcaatgt tgcccaggct ggtctcaaac tcctgggctc    22680
aagtgatcct cccacctcag cctcccaaag tgctgggatt gcaggtgcga gccacctcac    22740
ccagccttcg gctgactttc tgcatgctgc tgtttactcc tcacagaccc ctccccaact    22800
gaaatctctg cttttattag gtaaaattag gattcttatt tttaagtaac tgtggtagcc    22860
atagaacaaa gggcacagag gcttttctct tcacttttaa gtataattaa tgatttaatt    22920
ttttttgaga cagagtcttg cttgctctgt tgcccaggct ggagtgtagt ggcatgatct    22980
tggctcactg caacctccgc ctcccaggtt caacaattct cctgcttcaa cctcccaagt    23040
agctgggatt acagggtgt gccaccacgc ccagctaatt tttgtatttt tagtagagac    23100 agggttcac cgtgttgacc aggctggtct tgaactcctg acctcaggtg atctgcctgc    23160
ctctgcctcc caaagtgcta ggattacaag catgagccac tgtacctggc ctgttttttt    23220
gttttgtttt gttttgagac agggtcttgt tctgtcgccc aggctggagg gcagcggcgc    23280
gatctcagct cactggagcg cagtggcgcc atctcagctc actgcagcct ctgcctccca    23340
ggttcaagcg attctcctgc ctcagtccag agtagctggg attacaggtg tgtgccacca    23400
cgcctggcta attttttgtat ttttggtaga cgggtttt caccatgctg gccaggctgg    23460
tgaaagcaag atcttcaaga agtatttgta ttcccatgtt catagcagca tgattcacaa    23520
taactgagaa gtggaagcaa cccaggtgtc catcagtcag aggaaaggat aagcaaaatg    23580
cgcgcacact ctcaatggga tattattcag ccttcagcag aaggaaaatc ctatcacatg    23640
ctacagtgtg gagggacctt gaggacatta tgctaagtga aataagccgg tcatgaaaaa    23700
gcaaatcctg tatgatttca ctatataaga tacctagagt agtcaaattc agagagacag    23760
aaagtagaac cctgcttgcc agggcctaga gggagtgggg aagggagtt gttgtagagt    23820 ttcagtttca catgatgaaa acgttttgga gatgattggc ggtgatggta gcacaacacc    23880
ctaccgaaaa tgtttaagat ggtcaatgtt atgtgtattt caccacaatt tttaaaaagt    23940 caccagggc tgatgaccctt taaagaggct ctccagatgg ttgctggccc ctgggcgctt    24000
ctttgagact gttgaatctt taactcttag gtttcacgct atgataaaca aaccaacaac    24060
aacaaaaaaa gtgtggctca tgtctgtaac cccagcactt cgggaggctg aggccagtgg    24120
atcacttgag gtcaggagtt caagaccagc ttggccaaca tggtgaaacc ctgtctctac    24180
caaaaaatac aaaaattagc cgggcgtgat agcacatgcc tgttgtccca gctactgggg    24240
aggctgaggc gggaggattg ctagaaccca ggaggcagag attgcagtga gccaagattg    24300
tgccactgca ttccagcctg ggtgacagag caagactcca tctcaaaaca aacaaacaaa    24360
aagcaaagtt gggggggaaac aagaagggg gcactcttgc cgagtctcaa agattaagaa    24420
acaacagaaa aaagtggtc ccatctggag ccaggatgtc cagccacttg tccactgagt    24480
ccccaccccg ctgcctggac cctggggtct ctgggcttcc ctcccctctg gggaggagag    24540
attgtacaac cccaagcctt gcagagtgga gcagtgccac atctggcctc tagaaccaaa    24600
```

```
acaaatctgg gtcactttt aaaaaaaaga gttagaaatt ggtcttccct tacctcccct   24660
cactgtcacc ccagccctgc aaagagaggg caccactgct ctccatttgt aatctgggct   24720
cataggcact cagacctaga aggtgcatgg gtctttattt tacagatgag gagatggagg   24780
cccaaaacag ggggtgcaag gagcaaggtg cataggtca cacagctgac tgggaacgga   24840
gcccaaatgc accctggttc tttacacccc tcctcctaag aaacagctgt gcgctggagt   24900
cccataggca atgagcaggg ctgtcagctt cagtatcact gcctctcctg caaggggaca   24960
ggagagtaag accagtgact gcctggaggg gccacagcca gactagagga acacagccag   25020
caggtgaagt ttatctttag gtatctctct gcattcctct gcccttcagc atctcacgtc   25080
atcctcagca cagagccccg tttcaggaac tcacactcag actccgagat ggaaattggt   25140
tcctttccag gggtttacag agtccagtgc tgagcatcaa gaaatgaatc tcaatatgta   25200
caactattat ggatccataa aaattaaaaa tcaaaaaagt aaaataaagt gtaagaaatg   25260
aatctcagct gttggaatgc tactcatcat agcccctaag tgaaggagag atttcaaggt   25320
tattgctaag gaagggcatt cctgaagtcc ttaaatcatg attcccaaac ttgggttatt   25380 catatttat ctgcacaatt attaccatac cttgcattcc acttgtacag atatttaata   25440 tttcttata tcaccttagc ttttgaattt aatttacatt attttattat agaatctata   25500
atatattatt atattattgt atattaaaag gaattgctat cactactata tatgaacac   25560 cggattcact tgccataaat agaaggtagc tataaaaga tacaaagggg ccgggcacgg   25620
tggctcacac ctgtaatccc agcactttgg gaggccgagg caggcagatc acgaggtcaa   25680
gagtttgaga ccagcctggc caacatggtg aaatcccgtc tctactaaag atacaaaaaa   25740
ttagctgggc atggtggcac gcacctataa tcccagctac ttgggatggt ggggtagaat   25800
tccaaggtca gtgacacact ggcaggacac actgggggcc tcacaaagga ggggctcagc   25860
aggagagccc acccttcact cctgcctctg gctcttctcc gcaaagccca ggcatttctc   25920
tctttttttt ttggaactgt cttttgaga tagggtctca ctgcagcctg gacctcctgg   25980
gctcaagcaa tcctcctgtc tcagcttccc gagtagctgg gactacaggc acgtacccat   26040
catgcccgac tcattttaac attttgtag agatgaggtc tctctaagtt gtccaggcta   26100
gtctcaagct cctgggctca agcagtcctc ccacggtggc ctcccaaagt gctgagatta   26160
caggtgtgag ctaccacacc tggcaaaagt tcttattttt actactctgg ttgaatcaca   26220
agtattttct gtttggtcat ttgtaaaatg cagctattct gggtatccca caggagtgct   26280
gtaaggacag gactgaataa tgactagaaa tgcatttttt ccaccgtggt atgtgattgt   26340
catgggtaat taacactaag cccaggtggg tgagtgagct gagggctat agggacagag   26400 cacagtgtgc acagagctct gggaagacac aggtgcagtt ggtggcctgc agacccttc   26460 cattggatca ttccatgtga agggagttg gggccgtttg gaggtagcag agttctgggt   26520
ggcagccagg cccccaaata agcctcacta ctctggcttt ttttttttt tttttatgaa   26580 aaggagtctc gctctgttac ccaggctggt gtacagtggt gcaatcggct cactgcaacc   26640
tctgcctccc aggttcaagt gattctcctg ccccagcctc ctgagtagct gggattacag   26700
gctaccacca ccacgctggc taattttgt attttagta gagacggggt ttcaccatgt   26760
tagccaggct ggtctcgaac tcctgacctc aggtgatcca cccatgttgg tctcccaaag   26820
tgctgggatt atgggcatga gccaccgcac ccagcctcct ctgggttttt caggagaatc   26880
tgctgcctct actgcagcca cgcctttaaa aagtggaaaa accggcaggc aagaggctgc   26940
```

```
agatggcttg accaacctcc ctgttccctt ctaggtacca ggatcatcta tgaccggaaa    27000
ttcctgatgg agtgtcggaa ctcacctgtg accaaaacac ccccaaggga tctgcccacc    27060
attccggggg tcaccagccc ttccagtgat gagcccccca tggaagccag ccagagccac    27120
ctgcgcaata gcccagaaga taagcgggcg ggcggtgagt gtcggggctt ggccaggctc    27180
taccttggga aagggaatgt atgaggctcc tggagtccat ccactggggg caattccagg    27240
gaggaggaac aacagggact ctgccctacc ctctaaggag cagctcagag cccagagggt    27300
gagagtaggg gtgggaggt tgaactcttc attggtagca actttccccc tgaaaggggc    27360
ccaggcacct caggaaaggt gatctggcac ctttgggtca tgtaattagc ggggagtttg    27420
tttgaaatgg cagcggctgc acacagcaac tttcgtaagc atgtgcctct gtataattgt    27480
ctctgaagca tttccacttg aacacaccc atgatgtttg tggtgcaaga dacaagttat    27540
caaagacaca gtgtacttgt cctttgggaa attatatgtc tacaagataa gaaatacatc    27600
cgggatgcct cctgttgggc tgttggtccc ctagtggatc ttcatgaagg caggtagaaa    27660
caatgcagcc agttgtctct gccgatttga catttggtag ctgggtcctt cctgctgtcc    27720
ccacctcccg agtaattaga gcagccactg tggtagtggt gtaagtgaat gcactctttg    27780
tggcatcctg actggcttgg cagagtgttg gagttctctg ctgcaagatg atgcagcata    27840
agcacttccg ggcaactata atcagattgg aacccgccga cccttcaccc ggaaggccgt    27900
accccaggcc cagacaggaa gcagcaggga cctcagcttg gctggctctg ctaacagcag    27960
cagaattaat ctccccaggg cctgcaggac atgattcata attaccttgg gaacctcaca    28020
gtacaagaca gacaatagtt gcctgtgtct tagtctgttt ttttatggct gtaactgaat    28080
acctgagact gggtaattta tgaagaaaaa tggtttattt cttacagttc tagaggctgg    28140
gaaggccaag gcatggtgc ccgcatctgc tgggcttctg gtgagggcct cctgctgcat    28200
cataacatgg cggaaggcat cacagggcaa gagggggcaca tgagagagaa ccaagctgcc    28260
tttttataac actcttgtga taactagccc actcctgtgg taacccatta atccaggaat    28320
gggctaatcc attcatgagg acagagcctt catgacccaa ttacctctta acggccccaa    28380
ctcttaatac tgttacattg gggattaagt ttctgtatga atttcaaacc atagcattcc    28440
agccctggac cccccaaact catgtccttc tcatatacac atatattaat ttggtcccca    28500 tatcccccaaa gacttaacac gttgcagtcc tagctcaaaa gttcaaagtc cagaatttca    28560
tctgaatcag acaagactca cagcatgatt catctcaagc ttaatttcct tccagctgtg    28620
agcctgtgaa actaaacaag ttatctactt tcaaaaaata ggggctgtcc ctggccccta    28680
aaaacatcag ctggtggcca ggcacagtgg ctcatgcctg aaatcccagc actctgggag    28740
gctgaggcag gatgaatact tgaggccaga agttcaatac cagcctgggc aacaatgcaa    28800
gaccccatct ctacataaaa ttttaaaatt agccaggcat ggtggtgcat gcctgtaatc    28860
ccaactactt gggaggctga ggccagagga tcatttgagc ccaggaggtc aaggctgcag    28920
tgagctatga ttgcgtaact gcacgccagc ctggccaaga gagtgagacc ctgtctctaa    28980
agaaaaaagc aaaaacaaca agagtcagac gaaatgatat agtctggata tttgtccctg    29040
cccaaatctc atgttaaatt gtaatcccca gtgttggagg tagggcctgg tgggaggtgt    29100
ttgggtcgtg gggacagatc cctcacagct tggtgctgtc ctcatgatag tgaatgagtt    29160
ctctcgagat ctggttgttg taaagtgtgg gagcgccact ccaccctctc tcttgctcct    29220
gcttcctcca tgtgacatgc ctgctcccgc tttgctttcc accatgacga aaagcccct    29280 gaggcctccc cagaagccaa gctgaggccg gcgtcatgct tgtacagcct gcagaaccgc    29340
```

```
gagccagtta aacctctttt cttggctggg cacggtggct cgcacctgta atcccagcac    29400
tttgggaggc tgaggagggt ggatcatctg agatcaggag ttcgagacca gcctggccaa    29460
catggcaaaa ccccgggtct actaaaaata caaaaattag ctgggtgtgg tggtgggtgc    29520
ctataatccc agctactctt tgggaggct taggtaggaa aatcgcttga acccaggagg    29580
cggaggttgc agtgagccga aattgggcca ctgcactcca gcctcggaga cagagtgaga    29640
ctccatctca aaaaaaaaaa acaaaaaaac aaaaaaaac ttattttctt tataaattac    29700
ccaacctcag gtatttcttt atagcaatga agaatggcc tcatatacca agcattcacc    29760
cattgttgac ctggccctct gtcccctctc tccccaggtg aagagtcaca gtttgagatg    29820
gacatttaaa gcaccagcca tcgtgtggag cactaccaag gggcccctca gggccttcct    29880
gggaggagtc ccaccagcca ggccttatga aagtgatcat actgggcagg cgttggcgtg    29940
gggtcggaca ccccagccct ttctccctca ctcagggcac ctgccccctc ctcttcgtga    30000
acaccagcag atacctcctt gtgcctccac tgatgcagga gctgccaccc caaggggagt    30060 gaccctgcc agcacaccct gcagccaagg gccaggaagt ggacaagaac gaacccttcc    30120
ttccgaatga tcagcagttc cagccctcg ctgctggggg cgcaaccacc ccttccttag    30180
gttgatgtgc ttgggaaagc tccctccccc tccttcccca agagaggaaa taaaagccac    30240
cttcgcccta gggccaagag ttgggccccg tctgagcttt tttcaactct gtttggtaac    30300
taacaccagc tgctatctgt acagtgctgc tgctttttt tttttttt ttttgagacg    30360 gagtttcact cttgtggccc aggctggagt gcaatgcgc aatctcagct gattgcaacc    30420
tccacctcct gggttcaagc aattctcctg cctcagcctc ccgagtagct gggattacag    30480
gtgcccgcca ccatgcccag ctagtatttt tttgtatttt tgtagagaca gggtttcacc    30540
atgttggcca ggctggtctc gaactcttga cctcaggtga tccacccgcc ttggcctccc    30600
aaagtgctgg gattacaggt gtaagccacc gtgcccagcc ttgtacagtg ct            30652
```

<210> SEQ ID NO 27
<211> LENGTH: 20
<212> TYPE: DNA
<213> ORGANISM: Artificial Sequence
<220> FEATURE:
<223> OTHER INFORMATION: Antisense Compound

<400> SEQUENCE: 27
aggtggctct ggctggcttc                                                  20

<210> SEQ ID NO 28
<211> LENGTH: 20
<212> TYPE: DNA
<213> ORGANISM: Artificial Sequence
<220> FEATURE:
<223> OTHER INFORMATION: Antisense Compound

<400> SEQUENCE: 28
ctcatcactg gaagggctgg                                                  20

<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29

-continued

| gttccgacac tccatcagga | 20 |

<210> SEQ ID NO 30
<211> LENGTH: 20
<212> TYPE: DNA
<213> ORGANISM: Artificial Sequence
<220> FEATURE:
<223> OTHER INFORMATION: Antisense Compound

<400> SEQUENCE: 30

| ctggtgaccc ccggaatggt | 20 |

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31

| gggctattgc gcaggtggct | 20 |

<210> SEQ ID NO 32
<211> LENGTH: 20
<212> TYPE: DNA
<213> ORGANISM: Artificial Sequence
<220> FEATURE:
<223> OTHER INFORMATION: Antisense Compound

<400> SEQUENCE: 32

| attgcgcagg tggctctggc | 20 |

<210> SEQ ID NO 33
<211> LENGTH: 20
<212> TYPE: DNA
<213> ORGANISM: Artificial Sequence
<220> FEATURE:
<223> OTHER INFORMATION: Antisense Compound

<400> SEQUENCE: 33

| tcatcactgg aagggctggt | 20 |

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34

| ggtcgtgctg tagtccccgg | 20 |

<210> SEQ ID NO 35
<211> LENGTH: 20
<212> TYPE: DNA
<213> ORGANISM: Artificial Sequence
<220> FEATURE:
<223> OTHER INFORMATION: Antisense Compound

<400> SEQUENCE: 35

| cttctgggct attgcgcagg | 20 |

<210> SEQ ID NO 36
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 36
ccgcttatct tctgggctat                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
gctgcagctg ctgcccccgg                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
gtccatctca aactgtgact                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense Compound

<400> SEQUENCE: 39
gcccgcttat cttctgggct                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Compound

<400> SEQUENCE: 40
ggctgcagct gctgccccg                                                20

<210> SEQ ID NO 41
<211> LENGTH: 20
<212> TYPE: DNA
<213> ORGANISM: Artificial Sequence
<220> FEATURE:
<223> OTHER INFORMATION: Antisense Compound

<400> SEQUENCE: 41
ccgcccgctt atcttctggg                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Compound

<400> SEQUENCE: 42
ttttggtcac aggtgagttc                                               20
```

```
<210> SEQ ID NO 43
<211> LENGTH: 20
<212> TYPE: DNA
<213> ORGANISM: Artificial Sequence
<220> FEATURE:
<223> OTHER INFORMATION: Antisense Compound

<400> SEQUENCE: 43
tgacccccgg aatggtgggc                                                  20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
tcaggaattt ccggtcatag                                                  20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound

<400> SEQUENCE: 45
gaccccggga atggtgggca                                                  20

<210> SEQ ID NO 46
<211> LENGTH: 20
<212> TYPE: DNA
<213> ORGANISM: Artificial Sequence
<220> FEATURE:
<223> OTHER INFORMATION: Antisense Compound

<400> SEQUENCE: 46
ttctgggcta ttgcgcaggt                                                  20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
gggtctggct gcagctgctg                                                  20

<210> SEQ ID NO 48
<211> LENGTH: 20
<212> TYPE: DNA
<213> ORGANISM: Artificial Sequence
<220> FEATURE:
<223> OTHER INFORMATION: Antisense Compound

<400> SEQUENCE: 48
tggaagggct ggtgaccccc                                                  20

<210> SEQ ID NO 49
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 49
ccatcaggaa tttccggtca                                          20

<210> SEQ ID NO 50
<211> LENGTH: 20
<212> TYPE: DNA
<213> ORGANISM: Artificial Sequence
<220> FEATURE:
<223> OTHER INFORMATION: Antisense Compound

<400> SEQUENCE: 50
gacactccat caggaatttc                                          20

<210> SEQ ID NO 51
<211> LENGTH: 20
<212> TYPE: DNA
<213> ORGANISM: Artificial Sequence
<220> FEATURE:
<223> OTHER INFORMATION: Antisense Compound

<400> SEQUENCE: 51
ccgacactcc atcaggaatt                                          20

<210> SEQ ID NO 52
<211> LENGTH: 20
<212> TYPE: DNA
<213> ORGANISM: Artificial Sequence
<220> FEATURE:
<223> OTHER INFORMATION: Antisense Compound

<400> SEQUENCE: 52
tgagttccga cactccatca                                          20

<210> SEQ ID NO 53
<211> LENGTH: 20
<212> TYPE: DNA
<213> ORGANISM: Artificial Sequence
<220> FEATURE:
<223> OTHER INFORMATION: Antisense Compound

<400> SEQUENCE: 53
ggtgagttcc gacactccat                                          20

<210> SEQ ID NO 54
<211> LENGTH: 20
<212> TYPE: DNA
<213> ORGANISM: Artificial Sequence
<220> FEATURE:
<223> OTHER INFORMATION: Antisense Compound

<400> SEQUENCE: 54
cagctgctgc ccccggacat                                          20

<210> SEQ ID NO 55
<211> LENGTH: 20
<212> TYPE: DNA
<213> ORGANISM: Artificial Sequence
<220> FEATURE:
<223> OTHER INFORMATION: Antisense Compound

<400> SEQUENCE: 55
tggctgcagc tgctgccccc                                          20

<210> SEQ ID NO 56
```

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 56
ggctcatcac tggaagggct                                             20

<210> SEQ ID NO 57
<211> LENGTH: 20
<212> TYPE: DNA
<213> ORGANISM: Artificial Sequence
<220> FEATURE:
<223> OTHER INFORMATION: Antisense Compound

<400> SEQUENCE: 57
cggaatggtg ggcagatccc                                             20

<210> SEQ ID NO 58
<211> LENGTH: 20
<212> TYPE: DNA
<213> ORGANISM: Artificial Sequence
<220> FEATURE:
<223> OTHER INFORMATION: Antisense Compound

<400> SEQUENCE: 58
cgcccgctta tcttctgggc                                             20

<210> SEQ ID NO 59
<211> LENGTH: 20
<212> TYPE: DNA
<213> ORGANISM: Artificial Sequence
<220> FEATURE:
<223> OTHER INFORMATION: Antisense Compound

<400> SEQUENCE: 59
cgcaggtggc tctggctggc                                             20

<210> SEQ ID NO 60
<211> LENGTH: 20
<212> TYPE: DNA
<213> ORGANISM: Artificial Sequence
<220> FEATURE:
<223> OTHER INFORMATION: Antisense Compound

<400> SEQUENCE: 60
tccatctcaa actgtgactc                                             20

<210> SEQ ID NO 61
<211> LENGTH: 20
<212> TYPE: DNA
<213> ORGANISM: Artificial Sequence
<220> FEATURE:
<223> OTHER INFORMATION: Antisense Compound

<400> SEQUENCE: 61
gagcaccacc cggcgagtgg                                             20

<210> SEQ ID NO 62
<211> LENGTH: 20
<212> TYPE: DNA
<213> ORGANISM: Artificial Sequence
<220> FEATURE:
<223> OTHER INFORMATION: Antisense Compound

<400> SEQUENCE: 62
```

-continued

```
gcaggtggct ctggctggct                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Compound

<400> SEQUENCE: 63
tcgtgctgta gtccccgggc                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Compound

<400> SEQUENCE: 64
gtgctgtagt ccccgggcgg                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Compound

<400> SEQUENCE: 65
gtgctgaaga gcgtgccgcc                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Compound

<400> SEQUENCE: 66
gaatttccgg tcatagatga                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Compound

<400> SEQUENCE: 67
atcaggaatt tccggtcata                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Compound

<400> SEQUENCE: 68
actccatcag gaatttccgg                                              20

<210> SEQ ID NO 69
<211> LENGTH: 20
<212> TYPE: DNA
```

```
<213> ORGANISM: Artificial Sequence
<220> FEATURE:
<223> OTHER INFORMATION: Antisense Compound

<400> SEQUENCE: 69
tctcctgtgc gctgcacccg                                                   20

<210> SEQ ID NO 70
<211> LENGTH: 20
<212> TYPE: DNA
<213> ORGANISM: Artificial Sequence
<220> FEATURE:
<223> OTHER INFORMATION: Antisense Compound

<400> SEQUENCE: 70
ggtctcctgt gcgctgcacc                                                   20

<210> SEQ ID NO 71
<211> LENGTH: 20
<212> TYPE: DNA
<213> ORGANISM: Artificial Sequence
<220> FEATURE:
<223> OTHER INFORMATION: Antisense Compound

<400> SEQUENCE: 71
gacatggtct cctgtgcgct                                                   20

<210> SEQ ID NO 72
<211> LENGTH: 20
<212> TYPE: DNA
<213> ORGANISM: Artificial Sequence
<220> FEATURE:
<223> OTHER INFORMATION: Antisense Compound

<400> SEQUENCE: 72
ccccggacat ggtctcctgt                                                   20

<210> SEQ ID NO 73
<211> LENGTH: 20
<212> TYPE: DNA
<213> ORGANISM: Artificial Sequence
<220> FEATURE:
<223> OTHER INFORMATION: Antisense Compound

<400> SEQUENCE: 73
gcccccggac atggtctcct                                                   20

<210> SEQ ID NO 74
<211> LENGTH: 20
<212> TYPE: DNA
<213> ORGANISM: Artificial Sequence
<220> FEATURE:
<223> OTHER INFORMATION: Antisense Compound

<400> SEQUENCE: 74
gctgcccccg gacatggtct                                                   20

<210> SEQ ID NO 75
<211> LENGTH: 20
<212> TYPE: DNA
<213> ORGANISM: Artificial Sequence
<220> FEATURE:
<223> OTHER INFORMATION: Antisense Compound

<400> SEQUENCE: 75
ctgcagctgc tgccccgga                                                    20
```

```
<210> SEQ ID NO 76
<211> LENGTH: 20
<212> TYPE: DNA
<213> ORGANISM: Artificial Sequence
<220> FEATURE:
<223> OTHER INFORMATION: Antisense Compound

<400> SEQUENCE: 76
tctggctgca gctgctgccc                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Compound

<400> SEQUENCE: 77
gggtcgtgct gtagtccccg                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Compound

<400> SEQUENCE: 78
acactccatc aggaatttcc                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense Compound

<400> SEQUENCE: 79
ttccgacact ccatcaggaa                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense Compound

<400> SEQUENCE: 80
agttccgaca ctccatcagg                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Compound

<400> SEQUENCE: 81
caggtgagtt ccgacactcc                                              20

<210> SEQ ID NO 82
<211> LENGTH: 20
<212> TYPE: DNA
<213> ORGANISM: Artificial Sequence
<220> FEATURE:
```

<223> OTHER INFORMATION: Antisense Compound

<400> SEQUENCE: 82
ttggtcacag gtgagttccg                                         20

<210> SEQ ID NO 83
<211> LENGTH: 20
<212> TYPE: DNA
<213> ORGANISM: Artificial Sequence
<220> FEATURE:
<223> OTHER INFORMATION: Antisense Compound

<400> SEQUENCE: 83
gggtgttttg gtcacaggtg                                         20

<210> SEQ ID NO 84
<211> LENGTH: 20
<212> TYPE: DNA
<213> ORGANISM: Artificial Sequence
<220> FEATURE:
<223> OTHER INFORMATION: Antisense Compound

<400> SEQUENCE: 84
aatggtgggc agatcccttg                                         20

<210> SEQ ID NO 85
<211> LENGTH: 20
<212> TYPE: DNA
<213> ORGANISM: Artificial Sequence
<220> FEATURE:
<223> OTHER INFORMATION: Antisense Compound

<400> SEQUENCE: 85
cccggaatgg tgggcagatc                                         20

<210> SEQ ID NO 86
<211> LENGTH: 20
<212> TYPE: DNA
<213> ORGANISM: Artificial Sequence
<220> FEATURE:
<223> OTHER INFORMATION: Antisense Compound

<400> SEQUENCE: 86 gtgaccccccg gaatggtggg                                        20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
ggctggtgac ccccggaatg                                         20

<210> SEQ ID NO 88
<211> LENGTH: 20
<212> TYPE: DNA
<213> ORGANISM: Artificial Sequence
<220> FEATURE:
<223> OTHER INFORMATION: Antisense Compound

<400> SEQUENCE: 88
gggctggtga ccccggaat                                          20

```
<210> SEQ ID NO 89
<211> LENGTH: 20
<212> TYPE: DNA
<213> ORGANISM: Artificial Sequence
<220> FEATURE:
<223> OTHER INFORMATION: Antisense Compound

<400> SEQUENCE: 89
cactggaagg gctggtgacc                                               20

<210> SEQ ID NO 90
<211> LENGTH: 20
<212> TYPE: DNA
<213> ORGANISM: Artificial Sequence
<220> FEATURE:
<223> OTHER INFORMATION: Antisense Compound

<400> SEQUENCE: 90
atcactggaa gggctggtga                                               20

<210> SEQ ID NO 91
<211> LENGTH: 20
<212> TYPE: DNA
<213> ORGANISM: Artificial Sequence
<220> FEATURE:
<223> OTHER INFORMATION: Antisense Compound

<400> SEQUENCE: 91
gtggctctgg ctggcttcca                                               20

<210> SEQ ID NO 92
<211> LENGTH: 20
<212> TYPE: DNA
<213> ORGANISM: Artificial Sequence
<220> FEATURE:
<223> OTHER INFORMATION: Antisense Compound

<400> SEQUENCE: 92
tattgcgcag gtggctctgg                                               20

<210> SEQ ID NO 93
<211> LENGTH: 20
<212> TYPE: DNA
<213> ORGANISM: Artificial Sequence
<220> FEATURE:
<223> OTHER INFORMATION: Antisense Compound

<400> SEQUENCE: 93
tgggctattg cgcaggtggc                                               20

<210> SEQ ID NO 94
<211> LENGTH: 20
<212> TYPE: DNA
<213> ORGANISM: Artificial Sequence
<220> FEATURE:
<223> OTHER INFORMATION: Antisense Compound

<400> SEQUENCE: 94
tatcttctgg gctattgcgc                                               20

<210> SEQ ID NO 95
<211> LENGTH: 20
<212> TYPE: DNA
<213> ORGANISM: Artificial Sequence
<220> FEATURE:
<223> OTHER INFORMATION: Antisense Compound
```

<400> SEQUENCE: 95
ttatcttctg ggctattgcg                                                     20

<210> SEQ ID NO 96
<211> LENGTH: 20
<212> TYPE: DNA
<213> ORGANISM: Artificial Sequence
<220> FEATURE:
<223> OTHER INFORMATION: Antisense Compound

<400> SEQUENCE: 96
cccgcccgct tatcttctgg                                                     20

<210> SEQ ID NO 97
<211> LENGTH: 20
<212> TYPE: DNA
<213> ORGANISM: Artificial Sequence
<220> FEATURE:
<223> OTHER INFORMATION: Antisense Compound

<400> SEQUENCE: 97
tgtgactctt caccgcccgc                                                     20

<210> SEQ ID NO 98
<211> LENGTH: 20
<212> TYPE: DNA
<213> ORGANISM: Artificial Sequence
<220> FEATURE:
<223> OTHER INFORMATION: Antisense Compound

<400> SEQUENCE: 98
tcaaactgtg actcttcacc                                                     20

<210> SEQ ID NO 99
<211> LENGTH: 20
<212> TYPE: DNA
<213> ORGANISM: Artificial Sequence
<220> FEATURE:
<223> OTHER INFORMATION: Antisense Compound

<400> SEQUENCE: 99
atctcaaact gtgactcttc                                                     20

<210> SEQ ID NO 100
<211> LENGTH: 20
<212> TYPE: DNA
<213> ORGANISM: Artificial Sequence
<220> FEATURE:
<223> OTHER INFORMATION: Antisense Compound

<400> SEQUENCE: 100
ccatctcaaa ctgtgactct                                                     20

<210> SEQ ID NO 101
<211> LENGTH: 20
<212> TYPE: DNA
<213> ORGANISM: Artificial Sequence
<220> FEATURE:
<223> OTHER INFORMATION: Antisense Compound

<400> SEQUENCE: 101
gctggtgctt taaatgtcca                                                     20

<210> SEQ ID NO 102
<211> LENGTH: 20

```
<212> TYPE: DNA
<213> ORGANISM: Artificial Sequence
<220> FEATURE:
<223> OTHER INFORMATION: Antisense Compound

<400> SEQUENCE: 102
ctccacacga tggctggtgc                                              20

<210> SEQ ID NO 103
<211> LENGTH: 20
<212> TYPE: DNA
<213> ORGANISM: Artificial Sequence
<220> FEATURE:
<223> OTHER INFORMATION: Antisense Compound

<400> SEQUENCE: 103
tagtgctcca cacgatggct                                              20

<210> SEQ ID NO 104
<211> LENGTH: 20
<212> TYPE: DNA
<213> ORGANISM: Artificial Sequence
<220> FEATURE:
<223> OTHER INFORMATION: Antisense Compound

<400> SEQUENCE: 104
cccctBggta gtgctccaca                                              20
```
*(line reads: ccccttggta gtgctccaca)*
```
<210> SEQ ID NO 105
<211> LENGTH: 20
<212> TYPE: DNA
<213> ORGANISM: Artificial Sequence
<220> FEATURE:
<223> OTHER INFORMATION: Antisense Compound

<400> SEQUENCE: 105
ggcccctkgg tagtgctcca                                              20
```
*(line reads: ggcccctgg tagtgctcca)*
```
<210> SEQ ID NO 106
<211> LENGTH: 20
<212> TYPE: DNA
<213> ORGANISM: Artificial Sequence
<220> FEATURE:
<223> OTHER INFORMATION: Antisense Compound

<400> SEQUENCE: 106
cctcccagga aggccctgag                                              20

<210> SEQ ID NO 107
<211> LENGTH: 20
<212> TYPE: DNA
<213> ORGANISM: Artificial Sequence
<220> FEATURE:
<223> OTHER INFORMATION: Antisense Compound

<400> SEQUENCE: 107
tgggactcct cccaggaagg                                              20

<210> SEQ ID NO 108
<211> LENGTH: 20
<212> TYPE: DNA
<213> ORGANISM: Artificial Sequence
<220> FEATURE:
<223> OTHER INFORMATION: Antisense Compound

<400> SEQUENCE: 108
```
ctggtgggac tcctcccagg                                           20

<210> SEQ ID NO 109
<211> LENGTH: 20
<212> TYPE: DNA
<213> ORGANISM: Artificial Sequence
<220> FEATURE:
<223> OTHER INFORMATION: Antisense Compound

<400> SEQUENCE: 109
gcctggctgg tgggactcct                                           20

<210> SEQ ID NO 110
<211> LENGTH: 20
<212> TYPE: DNA
<213> ORGANISM: Artificial Sequence
<220> FEATURE:
<223> OTHER INFORMATION: Antisense Compound

<400> SEQUENCE: 110
ataaggcctg gctggtggga                                           20

<210> SEQ ID NO 111
<211> LENGTH: 20
<212> TYPE: DNA
<213> ORGANISM: Artificial Sequence
<220> FEATURE:
<223> OTHER INFORMATION: Antisense Compound

<400> SEQUENCE: 111
ttcataaggc ctggctggtg                                           20

<210> SEQ ID NO 112
<211> LENGTH: 20
<212> TYPE: DNA
<213> ORGANISM: Artificial Sequence
<220> FEATURE:
<223> OTHER INFORMATION: Antisense Compound

<400> SEQUENCE: 112
tatgatcact ttcataaggc                                           20

<210> SEQ ID NO 113
<211> LENGTH: 20
<212> TYPE: DNA
<213> ORGANISM: Artificial Sequence
<220> FEATURE:
<223> OTHER INFORMATION: Antisense Compound

<400> SEQUENCE: 113
cccagtatga tcactttcat                                           20

<210> SEQ ID NO 114
<211> LENGTH: 20
<212> TYPE: DNA
<213> ORGANISM: Artificial Sequence
<220> FEATURE:
<223> OTHER INFORMATION: Antisense Compound

<400> SEQUENCE: 114
acgcctgccc agtatgatca                                           20

<210> SEQ ID NO 115
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 115
ggtgtccgac cccacgccaa                                              20

<210> SEQ ID NO 116
<211> LENGTH: 20
<212> TYPE: DNA
<213> ORGANISM: Artificial Sequence
<220> FEATURE:
<223> OTHER INFORMATION: Antisense Compound

<400> SEQUENCE: 116
ccctgagtga gggagaaagg                                              20

<210> SEQ ID NO 117
<211> LENGTH: 20
<212> TYPE: DNA
<213> ORGANISM: Artificial Sequence
<220> FEATURE:
<223> OTHER INFORMATION: Antisense Compound

<400> SEQUENCE: 117
gtatctgctg gtgttcacga                                              20

<210> SEQ ID NO 118
<211> LENGTH: 20
<212> TYPE: DNA
<213> ORGANISM: Artificial Sequence
<220> FEATURE:
<223> OTHER INFORMATION: Antisense Compound

<400> SEQUENCE: 118
aaggaggtat ctgctggtgt                                              20

<210> SEQ ID NO 119
<211> LENGTH: 20
<212> TYPE: DNA
<213> ORGANISM: Artificial Sequence
<220> FEATURE:
<223> OTHER INFORMATION: Antisense Compound

<400> SEQUENCE: 119
aggcacaagg aggtatctgc                                              20

<210> SEQ ID NO 120
<211> LENGTH: 20
<212> TYPE: DNA
<213> ORGANISM: Artificial Sequence
<220> FEATURE:
<223> OTHER INFORMATION: Antisense Compound

<400> SEQUENCE: 120
ctgcatcagt ggaggcacaa                                              20

<210> SEQ ID NO 121
<211> LENGTH: 20
<212> TYPE: DNA
<213> ORGANISM: Artificial Sequence
<220> FEATURE:
<223> OTHER INFORMATION: Antisense Compound

<400> SEQUENCE: 121
agctcctgca tcagtggagg                                              20
```

```
<210> SEQ ID NO 122
<211> LENGTH: 20
<212> TYPE: DNA
<213> ORGANISM: Artificial Sequence
<220> FEATURE:
<223> OTHER INFORMATION: Antisense Compound

<400> SEQUENCE: 122
gcagctcctg catcagtgga                                                 20

<210> SEQ ID NO 123
<211> LENGTH: 20
<212> TYPE: DNA
<213> ORGANISM: Artificial Sequence
<220> FEATURE:
<223> OTHER INFORMATION: Antisense Compound

<400> SEQUENCE: 123
ggcccttggc tgcagggtgt                                                 20

<210> SEQ ID NO 124
<211> LENGTH: 20
<212> TYPE: DNA
<213> ORGANISM: Artificial Sequence
<220> FEATURE:
<223> OTHER INFORMATION: Antisense Compound

<400> SEQUENCE: 124
cttcctggcc cttggctgca                                                 20

<210> SEQ ID NO 125
<211> LENGTH: 20
<212> TYPE: DNA
<213> ORGANISM: Artificial Sequence
<220> FEATURE:
<223> OTHER INFORMATION: Antisense Compound

<400> SEQUENCE: 125
tccacttcct ggcccttggc                                                 20

<210> SEQ ID NO 126
<211> LENGTH: 20
<212> TYPE: DNA
<213> ORGANISM: Artificial Sequence
<220> FEATURE:
<223> OTHER INFORMATION: Antisense Compound

<400> SEQUENCE: 126
tgtccacttc ctggcccttg                                                 20

<210> SEQ ID NO 127
<211> LENGTH: 20
<212> TYPE: DNA
<213> ORGANISM: Artificial Sequence
<220> FEATURE:
<223> OTHER INFORMATION: Antisense Compound

<400> SEQUENCE: 127
cttgtccact tcctggccct                                                 20

<210> SEQ ID NO 128
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 128
gttcgttctt gtccacttcc                                          20

<210> SEQ ID NO 129
<211> LENGTH: 20
<212> TYPE: DNA
<213> ORGANISM: Artificial Sequence
<220> FEATURE:
<223> OTHER INFORMATION: Antisense Compound

<400> SEQUENCE: 129
ggaagggttc gttcttgtcc                                          20

<210> SEQ ID NO 130
<211> LENGTH: 20
<212> TYPE: DNA
<213> ORGANISM: Artificial Sequence
<220> FEATURE:
<223> OTHER INFORMATION: Antisense Compound

<400> SEQUENCE: 130
ggaaggaagg gttcgttctt                                          20

<210> SEQ ID NO 131
<211> LENGTH: 20
<212> TYPE: DNA
<213> ORGANISM: Artificial Sequence
<220> FEATURE:
<223> OTHER INFORMATION: Antisense Compound

<400> SEQUENCE: 131
gatcattcgg aaggaagggt                                          20

<210> SEQ ID NO 132
<211> LENGTH: 20
<212> TYPE: DNA
<213> ORGANISM: Artificial Sequence
<220> FEATURE:
<223> OTHER INFORMATION: Antisense Compound

<400> SEQUENCE: 132
tgctgatcat tcggaaggaa                                          20

<210> SEQ ID NO 133
<211> LENGTH: 20
<212> TYPE: DNA
<213> ORGANISM: Artificial Sequence
<220> FEATURE:
<223> OTHER INFORMATION: Antisense Compound

<400> SEQUENCE: 133
gtggttgcgc ccccagcagc                                          20

<210> SEQ ID NO 134
<211> LENGTH: 20
<212> TYPE: DNA
<213> ORGANISM: Artificial Sequence
<220> FEATURE:
<223> OTHER INFORMATION: Antisense Compound

<400> SEQUENCE: 134
ccaagcacat caacctaagg                                          20

<210> SEQ ID NO 135
```

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 135
tacaactccc cacgcaggag                                                   20

<210> SEQ ID NO 136
<211> LENGTH: 20
<212> TYPE: DNA
<213> ORGANISM: Artificial Sequence
<220> FEATURE:
<223> OTHER INFORMATION: Antisense Compound

<400> SEQUENCE: 136
acatcattgt gaaattcaca                                                   20

<210> SEQ ID NO 137
<211> LENGTH: 20
<212> TYPE: DNA
<213> ORGANISM: Artificial Sequence
<220> FEATURE:
<223> OTHER INFORMATION: Antisense Compound

<400> SEQUENCE: 137
cagctgagat tcatttctta                                                   20

<210> SEQ ID NO 138
<211> LENGTH: 20
<212> TYPE: DNA
<213> ORGANISM: Artificial Sequence
<220> FEATURE:
<223> OTHER INFORMATION: Antisense Compound

<400> SEQUENCE: 138
cctggtacct agaagggaac                                                   20

<210> SEQ ID NO 139
<211> LENGTH: 20
<212> TYPE: DNA
<213> ORGANISM: Artificial Sequence
<220> FEATURE:
<223> OTHER INFORMATION: Antisense Compound

<400> SEQUENCE: 139
caaagcggga gcaggcatgt                                                   20

<210> SEQ ID NO 140
<211> LENGTH: 20
<212> TYPE: DNA
<213> ORGANISM: Artificial Sequence
<220> FEATURE:
<223> OTHER INFORMATION: Antisense Compound

<400> SEQUENCE: 140
gcccgccgac atgtctcctg                                                   20

<210> SEQ ID NO 141
<211> LENGTH: 20
<212> TYPE: DNA
<213> ORGANISM: Artificial Sequence
<220> FEATURE:
<223> OTHER INFORMATION: Antisense Compound

<400> SEQUENCE: 141
```

```
gctggtccct taaatgtcca                                          20

<210> SEQ ID NO 142
<211> LENGTH: 20
<212> TYPE: DNA
<213> ORGANISM: Artificial Sequence
<220> FEATURE:
<223> OTHER INFORMATION: Antisense Compound

<400> SEQUENCE: 142
cagagctggc accctgagtg                                          20

<210> SEQ ID NO 143
<211> LENGTH: 20
<212> TYPE: DNA
<213> ORGANISM: Artificial Sequence
<220> FEATURE:
<223> OTHER INFORMATION: Antisense Compound

<400> SEQUENCE: 143
tttatttcct gtcagggaaa                                          20

<210> SEQ ID NO 144
<211> LENGTH: 20
<212> TYPE: DNA
<213> ORGANISM: Artificial Sequence
<220> FEATURE:
<223> OTHER INFORMATION: Antisense Compound

<400> SEQUENCE: 144
gagtgagagt cattcccctg                                          20

<210> SEQ ID NO 145
<211> LENGTH: 20
<212> TYPE: DNA
<213> ORGANISM: Artificial Sequence
<220> FEATURE:
<223> OTHER INFORMATION: Antisense Compound

<400> SEQUENCE: 145
tccactcgct ggagctccat                                          20

<210> SEQ ID NO 146
<211> LENGTH: 20
<212> TYPE: DNA
<213> ORGANISM: Artificial Sequence
<220> FEATURE:
<223> OTHER INFORMATION: Antisense Compound

<400> SEQUENCE: 146
ccctgagtga ggagcaggac                                          20

<210> SEQ ID NO 147
<211> LENGTH: 20
<212> TYPE: DNA
<213> ORGANISM: Artificial Sequence
<220> FEATURE:
<223> OTHER INFORMATION: Antisense Compound

<400> SEQUENCE: 147
gagtccactc gctggagctc                                          20

<210> SEQ ID NO 148
<211> LENGTH: 20
<212> TYPE: DNA
```

```
<213> ORGANISM: Artificial Sequence
<220> FEATURE:
<223> OTHER INFORMATION: Antisense Compound

<400> SEQUENCE: 148
ggtatgaggc ctgaatgctg                                               20

<210> SEQ ID NO 149
<211> LENGTH: 20
<212> TYPE: DNA
<213> ORGANISM: Artificial Sequence
<220> FEATURE:
<223> OTHER INFORMATION: Antisense Compound

<400> SEQUENCE: 149
gacatagaag catcattgcg                                               20

<210> SEQ ID NO 150
<211> LENGTH: 20
<212> TYPE: DNA
<213> ORGANISM: Artificial Sequence
<220> FEATURE:
<223> OTHER INFORMATION: Antisense Compound

<400> SEQUENCE: 150
aacccagcct aaggaaagat                                               20

<210> SEQ ID NO 151
<211> LENGTH: 20
<212> TYPE: DNA
<213> ORGANISM: Artificial Sequence
<220> FEATURE:
<223> OTHER INFORMATION: Antisense Compound

<400> SEQUENCE: 151
tcattgcgtc ctacggctgg                                               20

<210> SEQ ID NO 152
<211> LENGTH: 20
<212> TYPE: DNA
<213> ORGANISM: Artificial Sequence
<220> FEATURE:
<223> OTHER INFORMATION: Antisense Compound

<400> SEQUENCE: 152
agtccactcg ctggagctcc                                               20

<210> SEQ ID NO 153
<211> LENGTH: 20
<212> TYPE: DNA
<213> ORGANISM: Artificial Sequence
<220> FEATURE:
<223> OTHER INFORMATION: Antisense Compound

<400> SEQUENCE: 153
tgaatgctgt gcagctctcc                                               20

<210> SEQ ID NO 154
<211> LENGTH: 20
<212> TYPE: DNA
<213> ORGANISM: Artificial Sequence
<220> FEATURE:
<223> OTHER INFORMATION: Antisense Compound

<400> SEQUENCE: 154
tggtagggct agtgacccca                                               20
```

```
<210> SEQ ID NO 155
<211> LENGTH: 20
<212> TYPE: DNA
<213> ORGANISM: Artificial Sequence
<220> FEATURE:
<223> OTHER INFORMATION: Antisense Compound

<400> SEQUENCE: 155
ttcaccgcct gcccgcttat                                           20

<210> SEQ ID NO 156
<211> LENGTH: 20
<212> TYPE: DNA
<213> ORGANISM: Artificial Sequence
<220> FEATURE:
<223> OTHER INFORMATION: Antisense Compound

<400> SEQUENCE: 156
ttatttcctg tcagggaaag                                           20

<210> SEQ ID NO 157
<211> LENGTH: 20
<212> TYPE: DNA
<213> ORGANISM: Artificial Sequence
<220> FEATURE:
<223> OTHER INFORMATION: Antisense Compound

<400> SEQUENCE: 157
cagttggctc tggctggctt                                           20

<210> SEQ ID NO 158
<211> LENGTH: 20
<212> TYPE: DNA
<213> ORGANISM: Artificial Sequence
<220> FEATURE:
<223> OTHER INFORMATION: Antisense Compound

<400> SEQUENCE: 158
agatcattct gatagactcc                                           20

<210> SEQ ID NO 159
<211> LENGTH: 20
<212> TYPE: DNA
<213> ORGANISM: Artificial Sequence
<220> FEATURE:
<223> OTHER INFORMATION: Antisense Compound

<400> SEQUENCE: 159
ggtgttttgg ccacaggtga                                           20

<210> SEQ ID NO 160
<211> LENGTH: 20
<212> TYPE: DNA
<213> ORGANISM: Artificial Sequence
<220> FEATURE:
<223> OTHER INFORMATION: Antisense Compound

<400> SEQUENCE: 160
ccactcgctg gagctccatg                                           20

<210> SEQ ID NO 161
<211> LENGTH: 20
<212> TYPE: DNA
<213> ORGANISM: Artificial Sequence
<220> FEATURE:
```

<223> OTHER INFORMATION: Antisense Compound

<400> SEQUENCE: 161
gtgagtgaga gtcattcccc                                              20

<210> SEQ ID NO 162
<211> LENGTH: 20
<212> TYPE: DNA
<213> ORGANISM: Artificial Sequence
<220> FEATURE:
<223> OTHER INFORMATION: Antisense Compound

<400> SEQUENCE: 162
gcttgcatgg gaggctcatc                                              20

<210> SEQ ID NO 163
<211> LENGTH: 20
<212> TYPE: DNA
<213> ORGANISM: Artificial Sequence
<220> FEATURE:
<223> OTHER INFORMATION: Antisense Compound

<400> SEQUENCE: 163
gagttccgac actccatcag                                              20

<210> SEQ ID NO 164
<211> LENGTH: 20
<212> TYPE: DNA
<213> ORGANISM: Artificial Sequence
<220> FEATURE:
<223> OTHER INFORMATION: Antisense Compound

<400> SEQUENCE: 164
gtccactcgc tggagctcca                                              20

<210> SEQ ID NO 165
<211> LENGTH: 20
<212> TYPE: DNA
<213> ORGANISM: Artificial Sequence
<220> FEATURE:
<223> OTHER INFORMATION: Antisense Compound

<400> SEQUENCE: 165
gatagactcc tctgagtcca                                              20

<210> SEQ ID NO 166
<211> LENGTH: 20
<212> TYPE: DNA
<213> ORGANISM: Artificial Sequence
<220> FEATURE:
<223> OTHER INFORMATION: Antisense Compound

<400> SEQUENCE: 166
tgcagctgct gcccgccgac                                              20

<210> SEQ ID NO 167
<211> LENGTH: 20
<212> TYPE: DNA
<213> ORGANISM: Artificial Sequence
<220> FEATURE:
<223> OTHER INFORMATION: Antisense Compound

<400> SEQUENCE: 167
agtaaaagtg tggctttccc                                              20

```
<210> SEQ ID NO 168
<211> LENGTH: 20
<212> TYPE: DNA
<213> ORGANISM: Artificial Sequence
<220> FEATURE:
<223> OTHER INFORMATION: Antisense Compound

<400> SEQUENCE: 168
ctctggctgg cttgcatggg                                              20

<210> SEQ ID NO 169
<211> LENGTH: 20
<212> TYPE: DNA
<213> ORGANISM: Artificial Sequence
<220> FEATURE:
<223> OTHER INFORMATION: Antisense Compound

<400> SEQUENCE: 169
ggtaacccag cctaaggaaa                                              20

<210> SEQ ID NO 170
<211> LENGTH: 20
<212> TYPE: DNA
<213> ORGANISM: Artificial Sequence
<220> FEATURE:
<223> OTHER INFORMATION: Antisense Compound

<400> SEQUENCE: 170
cggagtggtg ctgtagtccc                                              20

<210> SEQ ID NO 171
<211> LENGTH: 20
<212> TYPE: DNA
<213> ORGANISM: Artificial Sequence
<220> FEATURE:
<223> OTHER INFORMATION: Antisense Compound

<400> SEQUENCE: 171
cgacactcca tcagaaattt                                              20

<210> SEQ ID NO 172
<211> LENGTH: 20
<212> TYPE: DNA
<213> ORGANISM: Artificial Sequence
<220> FEATURE:
<223> OTHER INFORMATION: Antisense Compound

<400> SEQUENCE: 172
gcacaaggag gtatgtgctg                                              20

<210> SEQ ID NO 173
<211> LENGTH: 20
<212> TYPE: DNA
<213> ORGANISM: Artificial Sequence
<220> FEATURE:
<223> OTHER INFORMATION: Antisense Compound

<400> SEQUENCE: 173
tccatcagaa atttccggtc                                              20

<210> SEQ ID NO 174
<211> LENGTH: 20
<212> TYPE: DNA
<213> ORGANISM: Artificial Sequence
<220> FEATURE:
<223> OTHER INFORMATION: Antisense Compound
```

<400> SEQUENCE: 174
gtcatagata atcctggttc                                                         20

<210> SEQ ID NO 175
<211> LENGTH: 20
<212> TYPE: DNA
<213> ORGANISM: Artificial Sequence
<220> FEATURE:
<223> OTHER INFORMATION: Antisense Compound

<400> SEQUENCE: 175
atagataatc ctggttcctc                                                         20

<210> SEQ ID NO 176
<211> LENGTH: 20
<212> TYPE: DNA
<213> ORGANISM: Artificial Sequence
<220> FEATURE:
<223> OTHER INFORMATION: Antisense Compound

<400> SEQUENCE: 176
tggcaccctg agtgaggagc                                                         20

<210> SEQ ID NO 177
<211> LENGTH: 20
<212> TYPE: DNA
<213> ORGANISM: Artificial Sequence
<220> FEATURE:
<223> OTHER INFORMATION: Antisense Compound

<400> SEQUENCE: 177
acatgtctcc tgcacgccgc                                                         20

<210> SEQ ID NO 178
<211> LENGTH: 20
<212> TYPE: DNA
<213> ORGANISM: Artificial Sequence
<220> FEATURE:
<223> OTHER INFORMATION: Antisense Compound

<400> SEQUENCE: 178
cgccgacatg tctcctgcac                                                         20

<210> SEQ ID NO 179
<211> LENGTH: 20
<212> TYPE: DNA
<213> ORGANISM: Artificial Sequence
<220> FEATURE:
<223> OTHER INFORMATION: Antisense Compound

<400> SEQUENCE: 179
gctgcccgcc gacatgtctc                                                         20

<210> SEQ ID NO 180
<211> LENGTH: 20
<212> TYPE: DNA
<213> ORGANISM: Artificial Sequence
<220> FEATURE:
<223> OTHER INFORMATION: Antisense Compound

<400> SEQUENCE: 180
caactgctgc ccgccgacat                                                         20

<210> SEQ ID NO 181
<211> LENGTH: 20

```
<212> TYPE: DNA
<213> ORGANISM: Artificial Sequence
<220> FEATURE:
<223> OTHER INFORMATION: Antisense Compound

<400> SEQUENCE: 181
agtctggctg caactgctgc                                               20

<210> SEQ ID NO 182
<211> LENGTH: 20
<212> TYPE: DNA
<213> ORGANISM: Artificial Sequence
<220> FEATURE:
<223> OTHER INFORMATION: Antisense Compound

<400> SEQUENCE: 182
cggctgggag tctggctgca                                               20

<210> SEQ ID NO 183
<211> LENGTH: 20
<212> TYPE: DNA
<213> ORGANISM: Artificial Sequence
<220> FEATURE:
<223> OTHER INFORMATION: Antisense Compound

<400> SEQUENCE: 183
atagcccggc tgggagtctg                                               20

<210> SEQ ID NO 184
<211> LENGTH: 20
<212> TYPE: DNA
<213> ORGANISM: Artificial Sequence
<220> FEATURE:
<223> OTHER INFORMATION: Antisense Compound

<400> SEQUENCE: 184
tccggtcata gatgattctg                                               20

<210> SEQ ID NO 185
<211> LENGTH: 20
<212> TYPE: DNA
<213> ORGANISM: Artificial Sequence
<220> FEATURE:
<223> OTHER INFORMATION: Antisense Compound

<400> SEQUENCE: 185
cacaggcgag ttccgacact                                               20

<210> SEQ ID NO 186
<211> LENGTH: 20
<212> TYPE: DNA
<213> ORGANISM: Artificial Sequence
<220> FEATURE:
<223> OTHER INFORMATION: Antisense Compound

<400> SEQUENCE: 186
tgttttggcc acaggcgagt                                               20

<210> SEQ ID NO 187
<211> LENGTH: 20
<212> TYPE: DNA
<213> ORGANISM: Artificial Sequence
<220> FEATURE:
<223> OTHER INFORMATION: Antisense Compound

<400> SEQUENCE: 187
```
acccctggaa tggttggcag                                              20

<210> SEQ ID NO 188
<211> LENGTH: 20
<212> TYPE: DNA
<213> ORGANISM: Artificial Sequence
<220> FEATURE:
<223> OTHER INFORMATION: Antisense Compound

<400> SEQUENCE: 188
tagtgacccc tggaatggtt                                              20

<210> SEQ ID NO 189
<211> LENGTH: 20
<212> TYPE: DNA
<213> ORGANISM: Artificial Sequence
<220> FEATURE:
<223> OTHER INFORMATION: Antisense Compound

<400> SEQUENCE: 189
agggctagtg acccctggaa                                              20

<210> SEQ ID NO 190
<211> LENGTH: 20
<212> TYPE: DNA
<213> ORGANISM: Artificial Sequence
<220> FEATURE:
<223> OTHER INFORMATION: Antisense Compound

<400> SEQUENCE: 190
ctggtagggc tagtgacccc                                              20

<210> SEQ ID NO 191
<211> LENGTH: 20
<212> TYPE: DNA
<213> ORGANISM: Artificial Sequence
<220> FEATURE:
<223> OTHER INFORMATION: Antisense Compound

<400> SEQUENCE: 191
catcgctggt agggctagtg                                              20

<210> SEQ ID NO 192
<211> LENGTH: 20
<212> TYPE: DNA
<213> ORGANISM: Artificial Sequence
<220> FEATURE:
<223> OTHER INFORMATION: Antisense Compound

<400> SEQUENCE: 192
aggctcatcg ctggtagggc                                              20

<210> SEQ ID NO 193
<211> LENGTH: 20
<212> TYPE: DNA
<213> ORGANISM: Artificial Sequence
<220> FEATURE:
<223> OTHER INFORMATION: Antisense Compound

<400> SEQUENCE: 193
atgggaggct catcgctggt                                              20

<210> SEQ ID NO 194
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 194
gcctgcatgg gaggctcatc                                                    20

<210> SEQ ID NO 195
<211> LENGTH: 20
<212> TYPE: DNA
<213> ORGANISM: Artificial Sequence
<220> FEATURE:
<223> OTHER INFORMATION: Antisense Compound

<400> SEQUENCE: 195
tctggctggc ctgcatggga                                                    20

<210> SEQ ID NO 196
<211> LENGTH: 20
<212> TYPE: DNA
<213> ORGANISM: Artificial Sequence
<220> FEATURE:
<223> OTHER INFORMATION: Antisense Compound

<400> SEQUENCE: 196
gatggctctg gctggcctgc                                                    20

<210> SEQ ID NO 197
<211> LENGTH: 20
<212> TYPE: DNA
<213> ORGANISM: Artificial Sequence
<220> FEATURE:
<223> OTHER INFORMATION: Antisense Compound

<400> SEQUENCE: 197
cttccgggct gctgtgcaga                                                    20

<210> SEQ ID NO 198
<211> LENGTH: 20
<212> TYPE: DNA
<213> ORGANISM: Artificial Sequence
<220> FEATURE:
<223> OTHER INFORMATION: Antisense Compound

<400> SEQUENCE: 198
gcttatcttc cgggctgctg                                                    20

<210> SEQ ID NO 199
<211> LENGTH: 20
<212> TYPE: DNA
<213> ORGANISM: Artificial Sequence
<220> FEATURE:
<223> OTHER INFORMATION: Antisense Compound

<400> SEQUENCE: 199
tgcccgctta tcttccgggc                                                    20

<210> SEQ ID NO 200
<211> LENGTH: 20
<212> TYPE: DNA
<213> ORGANISM: Artificial Sequence
<220> FEATURE:
<223> OTHER INFORMATION: Antisense Compound

<400> SEQUENCE: 200
ttcaccacct gcccgcttat                                                    20
```

<210> SEQ ID NO 201
<211> LENGTH: 20
<212> TYPE: DNA
<213> ORGANISM: Artificial Sequence
<220> FEATURE:
<223> OTHER INFORMATION: Antisense Compound

<400> SEQUENCE: 201
tgtgactctt caccacctgc                                               20

<210> SEQ ID NO 202
<211> LENGTH: 20
<212> TYPE: DNA
<213> ORGANISM: Artificial Sequence
<220> FEATURE:
<223> OTHER INFORMATION: Antisense Compound

<400> SEQUENCE: 202
ccttaaatgt ccatctcaaa                                               20

<210> SEQ ID NO 203
<211> LENGTH: 20
<212> TYPE: DNA
<213> ORGANISM: Artificial Sequence
<220> FEATURE:
<223> OTHER INFORMATION: Antisense Compound

<400> SEQUENCE: 203
tggtccctta aatgtccatc                                               20

<210> SEQ ID NO 204
<211> LENGTH: 20
<212> TYPE: DNA
<213> ORGANISM: Artificial Sequence
<220> FEATURE:
<223> OTHER INFORMATION: Antisense Compound

<400> SEQUENCE: 204
tcactgcgtc ctatggctgg                                               20

<210> SEQ ID NO 205
<211> LENGTH: 20
<212> TYPE: DNA
<213> ORGANISM: Artificial Sequence
<220> FEATURE:
<223> OTHER INFORMATION: Antisense Compound

<400> SEQUENCE: 205
cagaagcatc actgcgtcct                                               20

<210> SEQ ID NO 206
<211> LENGTH: 20
<212> TYPE: DNA
<213> ORGANISM: Artificial Sequence
<220> FEATURE:
<223> OTHER INFORMATION: Antisense Compound

<400> SEQUENCE: 206
gctgtggctc tcctcccaag                                               20

<210> SEQ ID NO 207
<211> LENGTH: 20
<212> TYPE: DNA
<213> ORGANISM: Artificial Sequence
<220> FEATURE:
<223> OTHER INFORMATION: Antisense Compound

```
<400> SEQUENCE: 207
aaggcctgac tgctgtggct                                              20

<210> SEQ ID NO 208
<211> LENGTH: 20
<212> TYPE: DNA
<213> ORGANISM: Artificial Sequence
<220> FEATURE:
<223> OTHER INFORMATION: Antisense Compound

<400> SEQUENCE: 208
ctgccgggta caaggcctga                                              20

<210> SEQ ID NO 209
<211> LENGTH: 20
<212> TYPE: DNA
<213> ORGANISM: Artificial Sequence
<220> FEATURE:
<223> OTHER INFORMATION: Antisense Compound

<400> SEQUENCE: 209
ccagtgtctg ccgggtacaa                                              20

<210> SEQ ID NO 210
<211> LENGTH: 20
<212> TYPE: DNA
<213> ORGANISM: Artificial Sequence
<220> FEATURE:
<223> OTHER INFORMATION: Antisense Compound

<400> SEQUENCE: 210
ccgatccaca cccagtgtct                                              20

<210> SEQ ID NO 211
<211> LENGTH: 20
<212> TYPE: DNA
<213> ORGANISM: Artificial Sequence
<220> FEATURE:
<223> OTHER INFORMATION: Antisense Compound

<400> SEQUENCE: 211
tgggtggccg atccacaccc                                              20

<210> SEQ ID NO 212
<211> LENGTH: 20
<212> TYPE: DNA
<213> ORGANISM: Artificial Sequence
<220> FEATURE:
<223> OTHER INFORMATION: Antisense Compound

<400> SEQUENCE: 212
caggactggg tggccgatcc                                              20

<210> SEQ ID NO 213
<211> LENGTH: 20
<212> TYPE: DNA
<213> ORGANISM: Artificial Sequence
<220> FEATURE:
<223> OTHER INFORMATION: Antisense Compound

<400> SEQUENCE: 213
ctgagtgagg agcaggactg                                              20

<210> SEQ ID NO 214
```

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 214
gtgccctgag tgaggagcag                                          20

<210> SEQ ID NO 215
<211> LENGTH: 20
<212> TYPE: DNA
<213> ORGANISM: Artificial Sequence
<220> FEATURE:
<223> OTHER INFORMATION: Antisense Compound

<400> SEQUENCE: 215
ggaaggcaga gcaggtgccc                                          20

<210> SEQ ID NO 216
<211> LENGTH: 20
<212> TYPE: DNA
<213> ORGANISM: Artificial Sequence
<220> FEATURE:
<223> OTHER INFORMATION: Antisense Compound

<400> SEQUENCE: 216
caaaatggaa ggcagagcag                                          20

<210> SEQ ID NO 217
<211> LENGTH: 20
<212> TYPE: DNA
<213> ORGANISM: Artificial Sequence
<220> FEATURE:
<223> OTHER INFORMATION: Antisense Compound

<400> SEQUENCE: 217
attcacaaaa tggaaggcag                                          20

<210> SEQ ID NO 218
<211> LENGTH: 20
<212> TYPE: DNA
<213> ORGANISM: Artificial Sequence
<220> FEATURE:
<223> OTHER INFORMATION: Antisense Compound

<400> SEQUENCE: 218
tgctggtatt cacaaaatgg                                          20

<210> SEQ ID NO 219
<211> LENGTH: 20
<212> TYPE: DNA
<213> ORGANISM: Artificial Sequence
<220> FEATURE:
<223> OTHER INFORMATION: Antisense Compound

<400> SEQUENCE: 219
ggtatgtgct ggtattcaca                                          20

<210> SEQ ID NO 220
<211> LENGTH: 20
<212> TYPE: DNA
<213> ORGANISM: Artificial Sequence
<220> FEATURE:
<223> OTHER INFORMATION: Antisense Compound

<400> SEQUENCE: 220
```

```
ggaggtatgt gctggtattc                                              20

<210> SEQ ID NO 221
<211> LENGTH: 20
<212> TYPE: DNA
<213> ORGANISM: Artificial Sequence
<220> FEATURE:
<223> OTHER INFORMATION: Antisense Compound

<400> SEQUENCE: 221
acaaggaggt atgtgctggt                                              20

<210> SEQ ID NO 222
<211> LENGTH: 20
<212> TYPE: DNA
<213> ORGANISM: Artificial Sequence
<220> FEATURE:
<223> OTHER INFORMATION: Antisense Compound

<400> SEQUENCE: 222
gaggcacaag gaggtatgtg                                              20

<210> SEQ ID NO 223
<211> LENGTH: 20
<212> TYPE: DNA
<213> ORGANISM: Artificial Sequence
<220> FEATURE:
<223> OTHER INFORMATION: Antisense Compound

<400> SEQUENCE: 223
aacagaggca caaggaggta                                              20

<210> SEQ ID NO 224
<211> LENGTH: 20
<212> TYPE: DNA
<213> ORGANISM: Artificial Sequence
<220> FEATURE:
<223> OTHER INFORMATION: Antisense Compound

<400> SEQUENCE: 224
atcaacagag gcacaaggag                                              20

<210> SEQ ID NO 225
<211> LENGTH: 20
<212> TYPE: DNA
<213> ORGANISM: Artificial Sequence
<220> FEATURE:
<223> OTHER INFORMATION: Antisense Compound

<400> SEQUENCE: 225
agtatcaaca gaggcacaag                                              20

<210> SEQ ID NO 226
<211> LENGTH: 20
<212> TYPE: DNA
<213> ORGANISM: Artificial Sequence
<220> FEATURE:
<223> OTHER INFORMATION: Antisense Compound

<400> SEQUENCE: 226
gtagcagctc agtatcaaca                                              20

<210> SEQ ID NO 227
<211> LENGTH: 20
<212> TYPE: DNA
```

```
<213> ORGANISM: Artificial Sequence
<220> FEATURE:
<223> OTHER INFORMATION: Antisense Compound

<400> SEQUENCE: 227
cctggagtag cagctcagta                                                  20

<210> SEQ ID NO 228
<211> LENGTH: 20
<212> TYPE: DNA
<213> ORGANISM: Artificial Sequence
<220> FEATURE:
<223> OTHER INFORMATION: Antisense Compound

<400> SEQUENCE: 228
accctggagt agcagctcag                                                  20

<210> SEQ ID NO 229
<211> LENGTH: 20
<212> TYPE: DNA
<213> ORGANISM: Artificial Sequence
<220> FEATURE:
<223> OTHER INFORMATION: Antisense Compound

<400> SEQUENCE: 229
agtcattacc ctggagtagc                                                  20

<210> SEQ ID NO 230
<211> LENGTH: 20
<212> TYPE: DNA
<213> ORGANISM: Artificial Sequence
<220> FEATURE:
<223> OTHER INFORMATION: Antisense Compound

<400> SEQUENCE: 230
gtgagagtca ttaccctgga                                                  20

<210> SEQ ID NO 231
<211> LENGTH: 20
<212> TYPE: DNA
<213> ORGANISM: Artificial Sequence
<220> FEATURE:
<223> OTHER INFORMATION: Antisense Compound

<400> SEQUENCE: 231
gtgtaggtga gagtcattac                                                  20

<210> SEQ ID NO 232
<211> LENGTH: 20
<212> TYPE: DNA
<213> ORGANISM: Artificial Sequence
<220> FEATURE:
<223> OTHER INFORMATION: Antisense Compound

<400> SEQUENCE: 232
ctgtgtccac tcgctggcgc                                                  20

<210> SEQ ID NO 233
<211> LENGTH: 20
<212> TYPE: DNA
<213> ORGANISM: Artificial Sequence
<220> FEATURE:
<223> OTHER INFORMATION: Antisense Compound

<400> SEQUENCE: 233
ctcctctgtg tccactcgct                                                  20
```

```
<210> SEQ ID NO 234
<211> LENGTH: 20
<212> TYPE: DNA
<213> ORGANISM: Artificial Sequence
<220> FEATURE:
<223> OTHER INFORMATION: Antisense Compound

<400> SEQUENCE: 234
gccagatcat tccgacagac                                                     20

<210> SEQ ID NO 235
<211> LENGTH: 20
<212> TYPE: DNA
<213> ORGANISM: Artificial Sequence
<220> FEATURE:
<223> OTHER INFORMATION: Antisense Compound

<400> SEQUENCE: 235
aattgccaga tcattccgac                                                     20

<210> SEQ ID NO 236
<211> LENGTH: 20
<212> TYPE: DNA
<213> ORGANISM: Artificial Sequence
<220> FEATURE:
<223> OTHER INFORMATION: Antisense Compound

<400> SEQUENCE: 236
ggctagaatt gccagatcat                                                     20

<210> SEQ ID NO 237
<211> LENGTH: 20
<212> TYPE: DNA
<213> ORGANISM: Artificial Sequence
<220> FEATURE:
<223> OTHER INFORMATION: Antisense Compound

<400> SEQUENCE: 237
gtgggtgtgc tccagaggtt                                                     20

<210> SEQ ID NO 238
<211> LENGTH: 20
<212> TYPE: DNA
<213> ORGANISM: Artificial Sequence
<220> FEATURE:
<223> OTHER INFORMATION: Antisense Compound

<400> SEQUENCE: 238
taaggtaagg tgggtgtgct                                                     20

<210> SEQ ID NO 239
<211> LENGTH: 20
<212> TYPE: DNA
<213> ORGANISM: Artificial Sequence
<220> FEATURE:
<223> OTHER INFORMATION: Antisense Compound

<400> SEQUENCE: 239
cccaacctaa ggtaaggtgg                                                     20

<210> SEQ ID NO 240
<211> LENGTH: 20
<212> TYPE: DNA
<213> ORGANISM: Artificial Sequence
<220> FEATURE:
```

```
<223> OTHER INFORMATION: Antisense Compound

<400> SEQUENCE: 240
aggtacccca acctaaggta                                              20

<210> SEQ ID NO 241
<211> LENGTH: 20
<212> TYPE: DNA
<213> ORGANISM: Artificial Sequence
<220> FEATURE:
<223> OTHER INFORMATION: Antisense Compound

<400> SEQUENCE: 241
ggtggctttc ccaggtaccc                                              20

<210> SEQ ID NO 242
<211> LENGTH: 20
<212> TYPE: DNA
<213> ORGANISM: Artificial Sequence
<220> FEATURE:
<223> OTHER INFORMATION: Antisense Compound

<400> SEQUENCE: 242
agggtggctt tcccaggtac                                              20

<210> SEQ ID NO 243
<211> LENGTH: 20
<212> TYPE: DNA
<213> ORGANISM: Artificial Sequence
<220> FEATURE:
<223> OTHER INFORMATION: Antisense Compound

<400> SEQUENCE: 243
ggaaagaagt aaagggtggc                                              20

<210> SEQ ID NO 244
<211> LENGTH: 20
<212> TYPE: DNA
<213> ORGANISM: Artificial Sequence
<220> FEATURE:
<223> OTHER INFORMATION: Antisense Compound

<400> SEQUENCE: 244
cttttatttc ctctcaggga                                              20

<210> SEQ ID NO 245
<211> LENGTH: 20
<212> TYPE: DNA
<213> ORGANISM: Artificial Sequence
<220> FEATURE:
<223> OTHER INFORMATION: Antisense Compound

<400> SEQUENCE: 245
tagggtaaat gtggctttta                                              20

<210> SEQ ID NO 246
<211> LENGTH: 20
<212> TYPE: DNA
<213> ORGANISM: Artificial Sequence
<220> FEATURE:
<223> OTHER INFORMATION: Antisense Compound

<400> SEQUENCE: 246
ttcagacagg gcccggctgt                                              20
```

```
<210> SEQ ID NO 247
<211> LENGTH: 20
<212> TYPE: DNA
<213> ORGANISM: H. sapiens
<220> FEATURE:

<400> SEQUENCE: 247
gaagccagcc agagccacct                                               20

<210> SEQ ID NO 248
<211> LENGTH: 20
<212> TYPE: DNA
<213> ORGANISM: H. sapiens
<220> FEATURE:

<400> SEQUENCE: 248
ccagcccttc cagtgatgag                                               20

<210> SEQ ID NO 249
<211> LENGTH: 20
<212> TYPE: DNA
<213> ORGANISM: H. sapiens
<220> FEATURE:

<400> SEQUENCE: 249
tcctgatgga gtgtcggaac                                               20

<210> SEQ ID NO 250
<211> LENGTH: 20
<212> TYPE: DNA
<213> ORGANISM: H. sapiens
<220> FEATURE:

<400> SEQUENCE: 250
accattccgg gggtcaccag                                               20

<210> SEQ ID NO 251
<211> LENGTH: 20
<212> TYPE: DNA
<213> ORGANISM: H. sapiens
<220> FEATURE:

<400> SEQUENCE: 251
gccagagcca cctgcgcaat                                               20

<210> SEQ ID NO 252
<211> LENGTH: 20
<212> TYPE: DNA
<213> ORGANISM: H. sapiens
<220> FEATURE:

<400> SEQUENCE: 252
agtcacagtt tgagatggac                                               20

<210> SEQ ID NO 253
<211> LENGTH: 20
<212> TYPE: DNA
<213> ORGANISM: H. sapiens
<220> FEATURE:

<400> SEQUENCE: 253
ctatgaccgg aaattcctga                                               20

<210> SEQ ID NO 254
<211> LENGTH: 20
```

-continued

```
<212> TYPE: DNA
<213> ORGANISM: H. sapiens
<220> FEATURE:

<400> SEQUENCE: 254
tgcccaccat tccggggtc                                                   20

<210> SEQ ID NO 255
<211> LENGTH: 20
<212> TYPE: DNA
<213> ORGANISM: H. sapiens
<220> FEATURE:

<400> SEQUENCE: 255
cagcagctgc agccagaccc                                                  20

<210> SEQ ID NO 256
<211> LENGTH: 20
<212> TYPE: DNA
<213> ORGANISM: H. sapiens
<220> FEATURE:

<400> SEQUENCE: 256
gggggtcacc agcccttcca                                                  20

<210> SEQ ID NO 257
<211> LENGTH: 20
<212> TYPE: DNA
<213> ORGANISM: H. sapiens
<220> FEATURE:

<400> SEQUENCE: 257
tgaccggaaa ttcctgatgg                                                  20

<210> SEQ ID NO 258
<211> LENGTH: 20
<212> TYPE: DNA
<213> ORGANISM: H. sapiens
<220> FEATURE:

<400> SEQUENCE: 258
agcccttcca gtgatgagcc                                                  20

<210> SEQ ID NO 259
<211> LENGTH: 20
<212> TYPE: DNA
<213> ORGANISM: H. sapiens
<220> FEATURE:

<400> SEQUENCE: 259
gccagccaga gccacctgcg                                                  20

<210> SEQ ID NO 260
<211> LENGTH: 20
<212> TYPE: DNA
<213> ORGANISM: H. sapiens
<220> FEATURE:

<400> SEQUENCE: 260
ccactcgccg ggtggtgctc                                                  20

<210> SEQ ID NO 261
<211> LENGTH: 20
<212> TYPE: DNA
<213> ORGANISM: H. sapiens
```

<220> FEATURE:

<400> SEQUENCE: 261
agccagccag agccacctgc                                           20

<210> SEQ ID NO 262
<211> LENGTH: 20
<212> TYPE: DNA
<213> ORGANISM: H. sapiens
<220> FEATURE:

<400> SEQUENCE: 262
gcccggggac tacagcacga                                           20

<210> SEQ ID NO 263
<211> LENGTH: 20
<212> TYPE: DNA
<213> ORGANISM: H. sapiens
<220> FEATURE:

<400> SEQUENCE: 263
ccgcccgggg actacagcac                                           20

<210> SEQ ID NO 264
<211> LENGTH: 20
<212> TYPE: DNA
<213> ORGANISM: H. sapiens
<220> FEATURE:

<400> SEQUENCE: 264
ggcggcacgc tcttcagcac                                           20

<210> SEQ ID NO 265
<211> LENGTH: 20
<212> TYPE: DNA
<213> ORGANISM: H. sapiens
<220> FEATURE:

<400> SEQUENCE: 265
tatgaccgga aattcctgat                                           20

<210> SEQ ID NO 266
<211> LENGTH: 20
<212> TYPE: DNA
<213> ORGANISM: H. sapiens
<220> FEATURE:

<400> SEQUENCE: 266
ccggaaattc ctgatggagt                                           20

<210> SEQ ID NO 267
<211> LENGTH: 20
<212> TYPE: DNA
<213> ORGANISM: H. sapiens
<220> FEATURE:

<400> SEQUENCE: 267
cgggtgcagc gcacaggaga                                           20

<210> SEQ ID NO 268
<211> LENGTH: 20
<212> TYPE: DNA
<213> ORGANISM: H. sapiens
<220> FEATURE:

<400> SEQUENCE: 268
ggtgcagcgc acaggagacc                                               20

<210> SEQ ID NO 269
<211> LENGTH: 20
<212> TYPE: DNA
<213> ORGANISM: H. sapiens
<220> FEATURE:

<400> SEQUENCE: 269
agcgcacagg agaccatgtc                                               20

<210> SEQ ID NO 270
<211> LENGTH: 20
<212> TYPE: DNA
<213> ORGANISM: H. sapiens
<220> FEATURE:

<400> SEQUENCE: 270
acaggagacc atgtccgggg                                               20

<210> SEQ ID NO 271
<211> LENGTH: 20
<212> TYPE: DNA
<213> ORGANISM: H. sapiens
<220> FEATURE:

<400> SEQUENCE: 271
aggagaccat gtccgggggc                                               20

<210> SEQ ID NO 272
<211> LENGTH: 20
<212> TYPE: DNA
<213> ORGANISM: H. sapiens
<220> FEATURE:

<400> SEQUENCE: 272
agaccatgtc cgggggcagc                                               20

<210> SEQ ID NO 273
<211> LENGTH: 20
<212> TYPE: DNA
<213> ORGANISM: H. sapiens
<220> FEATURE:

<400> SEQUENCE: 273
tccgggggca gcagctgcag                                               20

<210> SEQ ID NO 274
<211> LENGTH: 20
<212> TYPE: DNA
<213> ORGANISM: H. sapiens
<220> FEATURE:

<400> SEQUENCE: 274
gggcagcagc tgcagccaga                                               20

<210> SEQ ID NO 275
<211> LENGTH: 20
<212> TYPE: DNA
<213> ORGANISM: H. sapiens
<220> FEATURE:

<400> SEQUENCE: 275
cggggactac agcacgaccc    20

<210> SEQ ID NO 276
<211> LENGTH: 20
<212> TYPE: DNA
<213> ORGANISM: H. sapiens
<220> FEATURE:

<400> SEQUENCE: 276
ggaaattcct gatggagtgt    20

<210> SEQ ID NO 277
<211> LENGTH: 20
<212> TYPE: DNA
<213> ORGANISM: H. sapiens
<220> FEATURE:

<400> SEQUENCE: 277
ttcctgatgg agtgtcggaa    20

<210> SEQ ID NO 278
<211> LENGTH: 20
<212> TYPE: DNA
<213> ORGANISM: H. sapiens
<220> FEATURE:

<400> SEQUENCE: 278
cctgatggag tgtcggaact    20

<210> SEQ ID NO 279
<211> LENGTH: 20
<212> TYPE: DNA
<213> ORGANISM: H. sapiens
<220> FEATURE:

<400> SEQUENCE: 279
ggagtgtcgg aactcacctg    20

<210> SEQ ID NO 280
<211> LENGTH: 20
<212> TYPE: DNA
<213> ORGANISM: H. sapiens
<220> FEATURE:

<400> SEQUENCE: 280
cggaactcac ctgtgaccaa    20

<210> SEQ ID NO 281
<211> LENGTH: 20
<212> TYPE: DNA
<213> ORGANISM: H. sapiens
<220> FEATURE:

<400> SEQUENCE: 281
cacctgtgac caaaacaccc    20

<210> SEQ ID NO 282
<211> LENGTH: 20
<212> TYPE: DNA
<213> ORGANISM: H. sapiens
<220> FEATURE:

<400> SEQUENCE: 282
caagggatct gcccaccatt    20

```
<210> SEQ ID NO 283
<211> LENGTH: 20
<212> TYPE: DNA
<213> ORGANISM: H. sapiens
<220> FEATURE:

<400> SEQUENCE: 283
gatctgccca ccattccggg                                              20

<210> SEQ ID NO 284
<211> LENGTH: 20
<212> TYPE: DNA
<213> ORGANISM: H. sapiens
<220> FEATURE:

<400> SEQUENCE: 284
cattccgggg gtcaccagcc                                              20

<210> SEQ ID NO 285
<211> LENGTH: 20
<212> TYPE: DNA
<213> ORGANISM: H. sapiens
<220> FEATURE:

<400> SEQUENCE: 285
ggtcaccagc ccttccagtg                                              20

<210> SEQ ID NO 286
<211> LENGTH: 20
<212> TYPE: DNA
<213> ORGANISM: H. sapiens
<220> FEATURE:

<400> SEQUENCE: 286
tcaccagccc ttccagtgat                                              20

<210> SEQ ID NO 287
<211> LENGTH: 20
<212> TYPE: DNA
<213> ORGANISM: H. sapiens
<220> FEATURE:

<400> SEQUENCE: 287
tggaagccag ccagagccac                                              20

<210> SEQ ID NO 288
<211> LENGTH: 20
<212> TYPE: DNA
<213> ORGANISM: H. sapiens
<220> FEATURE:

<400> SEQUENCE: 288
gccacctgcg caatagccca                                              20

<210> SEQ ID NO 289
<211> LENGTH: 20
<212> TYPE: DNA
<213> ORGANISM: H. sapiens
<220> FEATURE:

<400> SEQUENCE: 289
gcgcaatagc ccagaagata                                              20

<210> SEQ ID NO 290
```

```
<211> LENGTH: 20
<212> TYPE: DNA
<213> ORGANISM: H. sapiens
<220> FEATURE:

<400> SEQUENCE: 290
cgcaatagcc cagaagataa                                                 20

<210> SEQ ID NO 291
<211> LENGTH: 20
<212> TYPE: DNA
<213> ORGANISM: H. sapiens
<220> FEATURE:

<400> SEQUENCE: 291
ccagaagata agcgggcggg                                                 20

<210> SEQ ID NO 292
<211> LENGTH: 20
<212> TYPE: DNA
<213> ORGANISM: H. sapiens
<220> FEATURE:

<400> SEQUENCE: 292
gcgggcggtg aagagtcaca                                                 20

<210> SEQ ID NO 293
<211> LENGTH: 20
<212> TYPE: DNA
<213> ORGANISM: H. sapiens
<220> FEATURE:

<400> SEQUENCE: 293
ggtgaagagt cacagtttga                                                 20

<210> SEQ ID NO 294
<211> LENGTH: 20
<212> TYPE: DNA
<213> ORGANISM: H. sapiens
<220> FEATURE:

<400> SEQUENCE: 294
gaagagtcac agtttgagat                                                 20

<210> SEQ ID NO 295
<211> LENGTH: 20
<212> TYPE: DNA
<213> ORGANISM: H. sapiens
<220> FEATURE:

<400> SEQUENCE: 295
agagtcacag tttgagatgg                                                 20

<210> SEQ ID NO 296
<211> LENGTH: 20
<212> TYPE: DNA
<213> ORGANISM: H. sapiens
<220> FEATURE:

<400> SEQUENCE: 296
tggacattta aagcaccagc                                                 20

<210> SEQ ID NO 297
<211> LENGTH: 20
<212> TYPE: DNA
```

```
<213> ORGANISM: H. sapiens
<220> FEATURE:

<400> SEQUENCE: 297
gcaccagcca tcgtgtggag                                               20

<210> SEQ ID NO 298
<211> LENGTH: 20
<212> TYPE: DNA
<213> ORGANISM: H. sapiens
<220> FEATURE:

<400> SEQUENCE: 298
agccatcgtg tggagcacta                                               20

<210> SEQ ID NO 299
<211> LENGTH: 20
<212> TYPE: DNA
<213> ORGANISM: H. sapiens
<220> FEATURE:

<400> SEQUENCE: 299
tgtggagcac taccaagggg                                               20

<210> SEQ ID NO 300
<211> LENGTH: 20
<212> TYPE: DNA
<213> ORGANISM: H. sapiens
<220> FEATURE:

<400> SEQUENCE: 300
tggagcacta ccaaggggcc                                               20

<210> SEQ ID NO 301
<211> LENGTH: 20
<212> TYPE: DNA
<213> ORGANISM: H. sapiens
<220> FEATURE:

<400> SEQUENCE: 301
ctcagggcct tcctgggagg                                               20

<210> SEQ ID NO 302
<211> LENGTH: 20
<212> TYPE: DNA
<213> ORGANISM: H. sapiens
<220> FEATURE:

<400> SEQUENCE: 302
ccttcctggg aggagtccca                                               20

<210> SEQ ID NO 303
<211> LENGTH: 20
<212> TYPE: DNA
<213> ORGANISM: H. sapiens
<220> FEATURE:

<400> SEQUENCE: 303
cctgggagga gtcccaccag                                               20

<210> SEQ ID NO 304
<211> LENGTH: 20
<212> TYPE: DNA
<213> ORGANISM: H. sapiens
<220> FEATURE:
```

<400> SEQUENCE: 304
aggagtccca ccagccaggc                                               20

<210> SEQ ID NO 305
<211> LENGTH: 20
<212> TYPE: DNA
<213> ORGANISM: H. sapiens
<220> FEATURE:

<400> SEQUENCE: 305
tcccaccagc caggccttat                                               20

<210> SEQ ID NO 306
<211> LENGTH: 20
<212> TYPE: DNA
<213> ORGANISM: H. sapiens
<220> FEATURE:

<400> SEQUENCE: 306
caccagccag gccttatgaa                                               20

<210> SEQ ID NO 307
<211> LENGTH: 20
<212> TYPE: DNA
<213> ORGANISM: H. sapiens
<220> FEATURE:

<400> SEQUENCE: 307
gccttatgaa agtgatcata                                               20

<210> SEQ ID NO 308
<211> LENGTH: 20
<212> TYPE: DNA
<213> ORGANISM: H. sapiens
<220> FEATURE:

<400> SEQUENCE: 308
atgaaagtga tcatactggg                                               20

<210> SEQ ID NO 309
<211> LENGTH: 20
<212> TYPE: DNA
<213> ORGANISM: H. sapiens
<220> FEATURE:

<400> SEQUENCE: 309
tgatcatact gggcaggcgt                                               20

<210> SEQ ID NO 310
<211> LENGTH: 20
<212> TYPE: DNA
<213> ORGANISM: H. sapiens
<220> FEATURE:

<400> SEQUENCE: 310
ttggcgtggg gtcggacacc                                               20

<210> SEQ ID NO 311
<211> LENGTH: 20
<212> TYPE: DNA
<213> ORGANISM: H. sapiens
<220> FEATURE:

<400> SEQUENCE: 311
cctttctccc tcactcaggg                                                    20

<210> SEQ ID NO 312
<211> LENGTH: 20
<212> TYPE: DNA
<213> ORGANISM: H. sapiens
<220> FEATURE:

<400> SEQUENCE: 312
tcgtgaacac cagcagatac                                                    20

<210> SEQ ID NO 313
<211> LENGTH: 20
<212> TYPE: DNA
<213> ORGANISM: H. sapiens
<220> FEATURE:

<400> SEQUENCE: 313
acaccagcag atacctcctt                                                    20

<210> SEQ ID NO 314
<211> LENGTH: 20
<212> TYPE: DNA
<213> ORGANISM: H. sapiens
<220> FEATURE:

<400> SEQUENCE: 314
gcagatacct ccttgtgcct                                                    20

<210> SEQ ID NO 315
<211> LENGTH: 20
<212> TYPE: DNA
<213> ORGANISM: H. sapiens
<220> FEATURE:

<400> SEQUENCE: 315
ttgtgcctcc actgatgcag                                                    20

<210> SEQ ID NO 316
<211> LENGTH: 20
<212> TYPE: DNA
<213> ORGANISM: H. sapiens
<220> FEATURE:

<400> SEQUENCE: 316
cctccactga tgcaggagct                                                    20

<210> SEQ ID NO 317
<211> LENGTH: 20
<212> TYPE: DNA
<213> ORGANISM: H. sapiens
<220> FEATURE:

<400> SEQUENCE: 317
tccactgatg caggagctgc                                                    20

<210> SEQ ID NO 318
<211> LENGTH: 20
<212> TYPE: DNA
<213> ORGANISM: H. sapiens
<220> FEATURE:

<400> SEQUENCE: 318
acaccctgca gccaagggcc                                                    20

```
<210> SEQ ID NO 319
<211> LENGTH: 20
<212> TYPE: DNA
<213> ORGANISM: H. sapiens
<220> FEATURE:

<400> SEQUENCE: 319
tgcagccaag ggccaggaag                                               20

<210> SEQ ID NO 320
<211> LENGTH: 20
<212> TYPE: DNA
<213> ORGANISM: H. sapiens
<220> FEATURE:

<400> SEQUENCE: 320
gccaagggcc aggaagtgga                                               20

<210> SEQ ID NO 321
<211> LENGTH: 20
<212> TYPE: DNA
<213> ORGANISM: H. sapiens
<220> FEATURE:

<400> SEQUENCE: 321
caagggccag gaagtggaca                                               20

<210> SEQ ID NO 322
<211> LENGTH: 20
<212> TYPE: DNA
<213> ORGANISM: H. sapiens
<220> FEATURE:

<400> SEQUENCE: 322
agggccagga agtggacaag                                               20

<210> SEQ ID NO 323
<211> LENGTH: 20
<212> TYPE: DNA
<213> ORGANISM: H. sapiens
<220> FEATURE:

<400> SEQUENCE: 323
ggaagtggac aagaacgaac                                               20

<210> SEQ ID NO 324
<211> LENGTH: 20
<212> TYPE: DNA
<213> ORGANISM: H. sapiens
<220> FEATURE:

<400> SEQUENCE: 324
ggacaagaac gaacccttcc                                               20

<210> SEQ ID NO 325
<211> LENGTH: 20
<212> TYPE: DNA
<213> ORGANISM: H. sapiens
<220> FEATURE:

<400> SEQUENCE: 325
aagaacgaac ccttccttcc                                               20
```

```
<210> SEQ ID NO 326
<211> LENGTH: 20
<212> TYPE: DNA
<213> ORGANISM: H. sapiens
<220> FEATURE:

<400> SEQUENCE: 326
acccttcctt ccgaatgatc                                              20

<210> SEQ ID NO 327
<211> LENGTH: 20
<212> TYPE: DNA
<213> ORGANISM: H. sapiens
<220> FEATURE:

<400> SEQUENCE: 327
ttccttccga atgatcagca                                              20

<210> SEQ ID NO 328
<211> LENGTH: 20
<212> TYPE: DNA
<213> ORGANISM: H. sapiens
<220> FEATURE:

<400> SEQUENCE: 328
gctgctgggg gcgcaaccac                                              20

<210> SEQ ID NO 329
<211> LENGTH: 20
<212> TYPE: DNA
<213> ORGANISM: H. sapiens
<220> FEATURE:

<400> SEQUENCE: 329
ccttaggttg atgtgcttgg                                              20

<210> SEQ ID NO 330
<211> LENGTH: 20
<212> TYPE: DNA
<213> ORGANISM: H. sapiens
<220> FEATURE:

<400> SEQUENCE: 330
tgtgaatttc acaatgatgt                                              20

<210> SEQ ID NO 331
<211> LENGTH: 20
<212> TYPE: DNA
<213> ORGANISM: H. sapiens
<220> FEATURE:

<400> SEQUENCE: 331
taagaaatga atctcagctg                                              20

<210> SEQ ID NO 332
<211> LENGTH: 20
<212> TYPE: DNA
<213> ORGANISM: H. sapiens
<220> FEATURE:

<400> SEQUENCE: 332
acatgcctgc tcccgctttg                                              20

<210> SEQ ID NO 333
<211> LENGTH: 20
```

```
<212> TYPE: DNA
<213> ORGANISM: M. musculus
<220> FEATURE:

<400> SEQUENCE: 333
caggagacat gtcggcgggc                                           20

<210> SEQ ID NO 334
<211> LENGTH: 20
<212> TYPE: DNA
<213> ORGANISM: M. musculus
<220> FEATURE:

<400> SEQUENCE: 334
tggacattta agggaccagc                                           20

<210> SEQ ID NO 335
<211> LENGTH: 20
<212> TYPE: DNA
<213> ORGANISM: M. musculus
<220> FEATURE:

<400> SEQUENCE: 335
cactcagggt gccagctctg                                           20

<210> SEQ ID NO 336
<211> LENGTH: 20
<212> TYPE: DNA
<213> ORGANISM: M. musculus
<220> FEATURE:

<400> SEQUENCE: 336
caggggaatg actctcactc                                           20

<210> SEQ ID NO 337
<211> LENGTH: 20
<212> TYPE: DNA
<213> ORGANISM: M. musculus
<220> FEATURE:

<400> SEQUENCE: 337
atggagctcc agcgagtgga                                           20

<210> SEQ ID NO 338
<211> LENGTH: 20
<212> TYPE: DNA
<213> ORGANISM: M. musculus
<220> FEATURE:

<400> SEQUENCE: 338
gtcctgctcc tcactcaggg                                           20

<210> SEQ ID NO 339
<211> LENGTH: 20
<212> TYPE: DNA
<213> ORGANISM: M. musculus
<220> FEATURE:

<400> SEQUENCE: 339
gagctccagc gagtggactc                                           20

<210> SEQ ID NO 340
<211> LENGTH: 20
<212> TYPE: DNA
<213> ORGANISM: M. musculus
```

```
<220> FEATURE:

<400> SEQUENCE: 340
cagcattcag gcctcatacc                                         20

<210> SEQ ID NO 341
<211> LENGTH: 20
<212> TYPE: DNA
<213> ORGANISM: M. musculus
<220> FEATURE:

<400> SEQUENCE: 341
cgcaatgatg cttctatgtc                                         20

<210> SEQ ID NO 342
<211> LENGTH: 20
<212> TYPE: DNA
<213> ORGANISM: M. musculus
<220> FEATURE:

<400> SEQUENCE: 342
atctttcctt aggctgggtt                                         20

<210> SEQ ID NO 343
<211> LENGTH: 20
<212> TYPE: DNA
<213> ORGANISM: M. musculus
<220> FEATURE:

<400> SEQUENCE: 343
ccagccgtag gacgcaatga                                         20

<210> SEQ ID NO 344
<211> LENGTH: 20
<212> TYPE: DNA
<213> ORGANISM: M. musculus
<220> FEATURE:

<400> SEQUENCE: 344
ggagctccag cgagtggact                                         20

<210> SEQ ID NO 345
<211> LENGTH: 20
<212> TYPE: DNA
<213> ORGANISM: M. musculus
<220> FEATURE:

<400> SEQUENCE: 345
ggagagctgc acagcattca                                         20

<210> SEQ ID NO 346
<211> LENGTH: 20
<212> TYPE: DNA
<213> ORGANISM: M. musculus
<220> FEATURE:

<400> SEQUENCE: 346
tggggtcact agccctacca                                         20

<210> SEQ ID NO 347
<211> LENGTH: 20
<212> TYPE: DNA
<213> ORGANISM: M. musculus
<220> FEATURE:
```

<400> SEQUENCE: 347
ataagcgggc aggcggtgaa                                                 20

<210> SEQ ID NO 348
<211> LENGTH: 20
<212> TYPE: DNA
<213> ORGANISM: M. musculus
<220> FEATURE:

<400> SEQUENCE: 348
ctttccctga caggaaataa                                                 20

<210> SEQ ID NO 349
<211> LENGTH: 20
<212> TYPE: DNA
<213> ORGANISM: M. musculus
<220> FEATURE:

<400> SEQUENCE: 349
aagccagcca gagccaactg                                                 20

<210> SEQ ID NO 350
<211> LENGTH: 20
<212> TYPE: DNA
<213> ORGANISM: M. musculus
<220> FEATURE:

<400> SEQUENCE: 350
ggagtctatc agaatgatct                                                 20

<210> SEQ ID NO 351
<211> LENGTH: 20
<212> TYPE: DNA
<213> ORGANISM: M. musculus
<220> FEATURE:

<400> SEQUENCE: 351
tcacctgtgg ccaaaacacc                                                 20

<210> SEQ ID NO 352
<211> LENGTH: 20
<212> TYPE: DNA
<213> ORGANISM: M. musculus
<220> FEATURE:

<400> SEQUENCE: 352
catggagctc cagcgagtgg                                                 20

<210> SEQ ID NO 353
<211> LENGTH: 20
<212> TYPE: DNA
<213> ORGANISM: M. musculus
<220> FEATURE:

<400> SEQUENCE: 353 gggggaatgac tctcactcac                                                20

<210> SEQ ID NO 354
<211> LENGTH: 20
<212> TYPE: DNA
<213> ORGANISM: M. musculus
<220> FEATURE:

<400> SEQUENCE: 354
gatgagcctc ccatgcaagc                                              20

<210> SEQ ID NO 355
<211> LENGTH: 20
<212> TYPE: DNA
<213> ORGANISM: M. musculus
<220> FEATURE:

<400> SEQUENCE: 355
ctgatggagt gtcggaactc                                              20

<210> SEQ ID NO 356
<211> LENGTH: 20
<212> TYPE: DNA
<213> ORGANISM: M. musculus
<220> FEATURE:

<400> SEQUENCE: 356
tggagctcca gcgagtggac                                              20

<210> SEQ ID NO 357
<211> LENGTH: 20
<212> TYPE: DNA
<213> ORGANISM: M. musculus
<220> FEATURE:

<400> SEQUENCE: 357
tggactcaga ggagtctatc                                              20

<210> SEQ ID NO 358
<211> LENGTH: 20
<212> TYPE: DNA
<213> ORGANISM: M. musculus
<220> FEATURE:

<400> SEQUENCE: 358
gtcggcgggc agcagctgca                                              20

<210> SEQ ID NO 359
<211> LENGTH: 20
<212> TYPE: DNA
<213> ORGANISM: M. musculus
<220> FEATURE:

<400> SEQUENCE: 359
gggaaagcca cacttttact                                              20

<210> SEQ ID NO 360
<211> LENGTH: 20
<212> TYPE: DNA
<213> ORGANISM: M. musculus
<220> FEATURE:

<400> SEQUENCE: 360
cccatgcaag ccagccagag                                              20

<210> SEQ ID NO 361
<211> LENGTH: 20
<212> TYPE: DNA
<213> ORGANISM: M. musculus
<220> FEATURE:

<400> SEQUENCE: 361
tttccttagg ctgggttacc                                              20

```
<210> SEQ ID NO 362
<211> LENGTH: 20
<212> TYPE: DNA
<213> ORGANISM: M. musculus
<220> FEATURE:

<400> SEQUENCE: 362
aaatttctga tggagtgtcg                                              20

<210> SEQ ID NO 363
<211> LENGTH: 20
<212> TYPE: DNA
<213> ORGANISM: M. musculus
<220> FEATURE:

<400> SEQUENCE: 363
cagcacatac ctccttgtgc                                              20

<210> SEQ ID NO 364
<211> LENGTH: 20
<212> TYPE: DNA
<213> ORGANISM: M. musculus
<220> FEATURE:

<400> SEQUENCE: 364
gaccggaaat ttctgatgga                                              20

<210> SEQ ID NO 365
<211> LENGTH: 20
<212> TYPE: DNA
<213> ORGANISM: M. musculus
<220> FEATURE:

<400> SEQUENCE: 365
gaaccaggat tatctatgac                                              20

<210> SEQ ID NO 366
<211> LENGTH: 20
<212> TYPE: DNA
<213> ORGANISM: M. musculus
<220> FEATURE:

<400> SEQUENCE: 366
gctcctcact cagggtgcca                                              20

<210> SEQ ID NO 367
<211> LENGTH: 20
<212> TYPE: DNA
<213> ORGANISM: R. norvegicus
<220> FEATURE:

<400> SEQUENCE: 367
gcggcgtgca ggagacatgt                                              20

<210> SEQ ID NO 368
<211> LENGTH: 20
<212> TYPE: DNA
<213> ORGANISM: R. norvegicus
<220> FEATURE:

<400> SEQUENCE: 368
gtgcaggaga catgtcggcg                                              20

<210> SEQ ID NO 369
```

```
<211> LENGTH: 20
<212> TYPE: DNA
<213> ORGANISM: R. norvegicus
<220> FEATURE:

<400> SEQUENCE: 369
gagacatgtc ggcgggcagc                                              20

<210> SEQ ID NO 370
<211> LENGTH: 20
<212> TYPE: DNA
<213> ORGANISM: R. norvegicus
<220> FEATURE:

<400> SEQUENCE: 370
atgtcggcgg gcagcagttg                                              20

<210> SEQ ID NO 371
<211> LENGTH: 20
<212> TYPE: DNA
<213> ORGANISM: R. norvegicus
<220> FEATURE:

<400> SEQUENCE: 371
gcagcagttg cagccagact                                              20

<210> SEQ ID NO 372
<211> LENGTH: 20
<212> TYPE: DNA
<213> ORGANISM: R. norvegicus
<220> FEATURE:

<400> SEQUENCE: 372
tgcagccaga ctcccagccg                                              20

<210> SEQ ID NO 373
<211> LENGTH: 20
<212> TYPE: DNA
<213> ORGANISM: R. norvegicus
<220> FEATURE:

<400> SEQUENCE: 373
cagactccca gccgggctat                                              20

<210> SEQ ID NO 374
<211> LENGTH: 20
<212> TYPE: DNA
<213> ORGANISM: R. norvegicus
<220> FEATURE:

<400> SEQUENCE: 374
cagaatcatc tatgaccgga                                              20

<210> SEQ ID NO 375
<211> LENGTH: 20
<212> TYPE: DNA
<213> ORGANISM: R. norvegicus
<220> FEATURE:

<400> SEQUENCE: 375
agtgtcggaa ctcgcctgtg                                              20

<210> SEQ ID NO 376
<211> LENGTH: 20
<212> TYPE: DNA
```

```
<213> ORGANISM: R. norvegicus
<220> FEATURE:

<400> SEQUENCE: 376
actcgcctgt ggccaaaaca                                               20

<210> SEQ ID NO 377
<211> LENGTH: 20
<212> TYPE: DNA
<213> ORGANISM: R. norvegicus
<220> FEATURE:

<400> SEQUENCE: 377
ctgccaacca ttccaggggt                                               20

<210> SEQ ID NO 378
<211> LENGTH: 20
<212> TYPE: DNA
<213> ORGANISM: R. norvegicus
<220> FEATURE:

<400> SEQUENCE: 378
aaccattcca ggggtcacta                                               20

<210> SEQ ID NO 379
<211> LENGTH: 20
<212> TYPE: DNA
<213> ORGANISM: R. norvegicus
<220> FEATURE:

<400> SEQUENCE: 379
ttccaggggt cactagccct                                               20

<210> SEQ ID NO 380
<211> LENGTH: 20
<212> TYPE: DNA
<213> ORGANISM: R. norvegicus
<220> FEATURE:

<400> SEQUENCE: 380
ggggtcacta gccctaccag                                               20

<210> SEQ ID NO 381
<211> LENGTH: 20
<212> TYPE: DNA
<213> ORGANISM: R. norvegicus
<220> FEATURE:

<400> SEQUENCE: 381
cactagccct accagcgatg                                               20

<210> SEQ ID NO 382
<211> LENGTH: 20
<212> TYPE: DNA
<213> ORGANISM: R. norvegicus
<220> FEATURE:

<400> SEQUENCE: 382
gccctaccag cgatgagcct                                               20

<210> SEQ ID NO 383
<211> LENGTH: 20
<212> TYPE: DNA
<213> ORGANISM: R. norvegicus
<220> FEATURE:
```

<400> SEQUENCE: 383
accagcgatg agcctcccat                                          20

<210> SEQ ID NO 384
<211> LENGTH: 20
<212> TYPE: DNA
<213> ORGANISM: R. norvegicus
<220> FEATURE:

<400> SEQUENCE: 384
gcaggccagc cagagccatc                                          20

<210> SEQ ID NO 385
<211> LENGTH: 20
<212> TYPE: DNA
<213> ORGANISM: R. norvegicus
<220> FEATURE:

<400> SEQUENCE: 385
tctgcacagc agcccggaag                                          20

<210> SEQ ID NO 386
<211> LENGTH: 20
<212> TYPE: DNA
<213> ORGANISM: R. norvegicus
<220> FEATURE:

<400> SEQUENCE: 386
cagcagcccg gaagataagc                                          20

<210> SEQ ID NO 387
<211> LENGTH: 20
<212> TYPE: DNA
<213> ORGANISM: R. norvegicus
<220> FEATURE:

<400> SEQUENCE: 387
gcaggtggtg aagagtcaca                                          20

<210> SEQ ID NO 388
<211> LENGTH: 20
<212> TYPE: DNA
<213> ORGANISM: R. norvegicus
<220> FEATURE:

<400> SEQUENCE: 388
tttgagatgg acatttaagg                                          20

<210> SEQ ID NO 389
<211> LENGTH: 20
<212> TYPE: DNA
<213> ORGANISM: R. norvegicus
<220> FEATURE:

<400> SEQUENCE: 389
gatggacatt taagggacca                                          20

<210> SEQ ID NO 390
<211> LENGTH: 20
<212> TYPE: DNA
<213> ORGANISM: R. norvegicus
<220> FEATURE:

<400> SEQUENCE: 390

```
ccagccatag gacgcagtga                                                    20

<210> SEQ ID NO 391
<211> LENGTH: 20
<212> TYPE: DNA
<213> ORGANISM: R. norvegicus
<220> FEATURE:

<400> SEQUENCE: 391
aggacgcagt gatgcttctg                                                    20

<210> SEQ ID NO 392
<211> LENGTH: 20
<212> TYPE: DNA
<213> ORGANISM: R. norvegicus
<220> FEATURE:

<400> SEQUENCE: 392
cttgggagga gagccacagc                                                    20

<210> SEQ ID NO 393
<211> LENGTH: 20
<212> TYPE: DNA
<213> ORGANISM: R. norvegicus
<220> FEATURE:

<400> SEQUENCE: 393
agccacagca gtcaggcctt                                                    20

<210> SEQ ID NO 394
<211> LENGTH: 20
<212> TYPE: DNA
<213> ORGANISM: R. norvegicus
<220> FEATURE:

<400> SEQUENCE: 394
tcaggccttg tacccggcag                                                    20

<210> SEQ ID NO 395
<211> LENGTH: 20
<212> TYPE: DNA
<213> ORGANISM: R. norvegicus
<220> FEATURE:

<400> SEQUENCE: 395
ttgtacccgg cagacactgg                                                    20

<210> SEQ ID NO 396
<211> LENGTH: 20
<212> TYPE: DNA
<213> ORGANISM: R. norvegicus
<220> FEATURE:

<400> SEQUENCE: 396
agacactggg tgtggatcgg                                                    20

<210> SEQ ID NO 397
<211> LENGTH: 20
<212> TYPE: DNA
<213> ORGANISM: R. norvegicus
<220> FEATURE:

<400> SEQUENCE: 397
ggatcggcca cccagtcctg                                                    20
```

```
<210> SEQ ID NO 398
<211> LENGTH: 20
<212> TYPE: DNA
<213> ORGANISM: R. norvegicus
<220> FEATURE:

<400> SEQUENCE: 398
gggcacctgc tctgccttcc                                               20

<210> SEQ ID NO 399
<211> LENGTH: 20
<212> TYPE: DNA
<213> ORGANISM: R. norvegicus
<220> FEATURE:

<400> SEQUENCE: 399
ctgccttcca ttttgtgaat                                               20

<210> SEQ ID NO 400
<211> LENGTH: 20
<212> TYPE: DNA
<213> ORGANISM: R. norvegicus
<220> FEATURE:

<400> SEQUENCE: 400
ccattttgtg aataccagca                                               20

<210> SEQ ID NO 401
<211> LENGTH: 20
<212> TYPE: DNA
<213> ORGANISM: R. norvegicus
<220> FEATURE:

<400> SEQUENCE: 401
tgtgaatacc agcacatacc                                               20

<210> SEQ ID NO 402
<211> LENGTH: 20
<212> TYPE: DNA
<213> ORGANISM: R. norvegicus
<220> FEATURE:

<400> SEQUENCE: 402
gaataccagc acatacctcc                                               20

<210> SEQ ID NO 403
<211> LENGTH: 20
<212> TYPE: DNA
<213> ORGANISM: R. norvegicus
<220> FEATURE:

<400> SEQUENCE: 403
accagcacat acctccttgt                                               20

<210> SEQ ID NO 404
<211> LENGTH: 20
<212> TYPE: DNA
<213> ORGANISM: R. norvegicus
<220> FEATURE:

<400> SEQUENCE: 404
cacatacctc cttgtgcctc                                               20
```

```
<210> SEQ ID NO 405
<211> LENGTH: 20
<212> TYPE: DNA
<213> ORGANISM: R. norvegicus
<220> FEATURE:

<400> SEQUENCE: 405
tacctccttg tgcctctgtt                                                   20

<210> SEQ ID NO 406
<211> LENGTH: 20
<212> TYPE: DNA
<213> ORGANISM: R. norvegicus
<220> FEATURE:

<400> SEQUENCE: 406
ctccttgtgc ctctgttgat                                                   20

<210> SEQ ID NO 407
<211> LENGTH: 20
<212> TYPE: DNA
<213> ORGANISM: R. norvegicus
<220> FEATURE:

<400> SEQUENCE: 407
cttgtgcctc tgttgatact                                                   20

<210> SEQ ID NO 408
<211> LENGTH: 20
<212> TYPE: DNA
<213> ORGANISM: R. norvegicus
<220> FEATURE:

<400> SEQUENCE: 408
tgttgatact gagctgctac                                                   20

<210> SEQ ID NO 409
<211> LENGTH: 20
<212> TYPE: DNA
<213> ORGANISM: R. norvegicus
<220> FEATURE:

<400> SEQUENCE: 409
tactgagctg ctactccagg                                                   20

<210> SEQ ID NO 410
<211> LENGTH: 20
<212> TYPE: DNA
<213> ORGANISM: R. norvegicus
<220> FEATURE:

<400> SEQUENCE: 410
ctgagctgct actccagggt                                                   20

<210> SEQ ID NO 411
<211> LENGTH: 20
<212> TYPE: DNA
<213> ORGANISM: R. norvegicus
<220> FEATURE:

<400> SEQUENCE: 411
gctactccag ggtaatgact                                                   20

<210> SEQ ID NO 412
<211> LENGTH: 20
```

<212> TYPE: DNA
<213> ORGANISM: R. norvegicus
<220> FEATURE:

<400> SEQUENCE: 412
tccagggtaa tgactctcac                                               20

<210> SEQ ID NO 413
<211> LENGTH: 20
<212> TYPE: DNA
<213> ORGANISM: R. norvegicus
<220> FEATURE:

<400> SEQUENCE: 413
gtaatgactc tcacctacac                                               20

<210> SEQ ID NO 414
<211> LENGTH: 20
<212> TYPE: DNA
<213> ORGANISM: R. norvegicus
<220> FEATURE:

<400> SEQUENCE: 414
gcgccagcga gtggacacag                                               20

<210> SEQ ID NO 415
<211> LENGTH: 20
<212> TYPE: DNA
<213> ORGANISM: R. norvegicus
<220> FEATURE:

<400> SEQUENCE: 415
agcgagtgga cacagaggag                                               20

<210> SEQ ID NO 416
<211> LENGTH: 20
<212> TYPE: DNA
<213> ORGANISM: R. norvegicus
<220> FEATURE:

<400> SEQUENCE: 416
gtctgtcgga atgatctggc                                               20

<210> SEQ ID NO 417
<211> LENGTH: 20
<212> TYPE: DNA
<213> ORGANISM: R. norvegicus
<220> FEATURE:

<400> SEQUENCE: 417
gtcggaatga tctggcaatt                                               20

<210> SEQ ID NO 418
<211> LENGTH: 20
<212> TYPE: DNA
<213> ORGANISM: R. norvegicus
<220> FEATURE:

<400> SEQUENCE: 418
atgatctggc aattctagcc                                               20

<210> SEQ ID NO 419
<211> LENGTH: 20
<212> TYPE: DNA
<213> ORGANISM: R. norvegicus

```
<220> FEATURE:

<400> SEQUENCE: 419
aacctctgga gcacacccac                                                    20

<210> SEQ ID NO 420
<211> LENGTH: 20
<212> TYPE: DNA
<213> ORGANISM: R. norvegicus
<220> FEATURE:

<400> SEQUENCE: 420
ccaccttacc ttaggttggg                                                    20

<210> SEQ ID NO 421
<211> LENGTH: 20
<212> TYPE: DNA
<213> ORGANISM: R. norvegicus
<220> FEATURE:

<400> SEQUENCE: 421
taccttaggt tggggtacct                                                    20

<210> SEQ ID NO 422
<211> LENGTH: 20
<212> TYPE: DNA
<213> ORGANISM: R. norvegicus
<220> FEATURE:

<400> SEQUENCE: 422
gggtacctgg gaaagccacc                                                    20

<210> SEQ ID NO 423
<211> LENGTH: 20
<212> TYPE: DNA
<213> ORGANISM: R. norvegicus
<220> FEATURE:

<400> SEQUENCE: 423
gtacctggga agccaccct                                                     20

<210> SEQ ID NO 424
<211> LENGTH: 20
<212> TYPE: DNA
<213> ORGANISM: R. norvegicus
<220> FEATURE:

<400> SEQUENCE: 424
gccacccttt acttctttcc                                                    20

<210> SEQ ID NO 425
<211> LENGTH: 20
<212> TYPE: DNA
<213> ORGANISM: R. norvegicus
<220> FEATURE:

<400> SEQUENCE: 425
tccctgagag gaaataaaag                                                    20

<210> SEQ ID NO 426
<211> LENGTH: 20
<212> TYPE: DNA
<213> ORGANISM: R. norvegicus
<220> FEATURE:
```

```
<400> SEQUENCE: 426
taaaagccac atttacccta                                              20

<210> SEQ ID NO 427
<211> LENGTH: 20
<212> TYPE: DNA
<213> ORGANISM: R. norvegicus
<220> FEATURE:

<400> SEQUENCE: 427
acagccgggc cctgtctgaa                                              20

<210> SEQ ID NO 428
<211> LENGTH: 603
<212> TYPE: DNA
<213> ORGANISM: R. spretus
<220> FEATURE:
<221> NAME/KEY: CDS
<222> LOCATION: (2)...(139)

<400> SEQUENCE: 428 g gac ttg cca acc att cca ggg gtc act agc cct acc agc gat gag cct    49
  Asp Leu Pro Thr Ile Pro Gly Val Thr Ser Pro Thr Ser Asp Glu Pro
   1               5                  10                  15 ccc atg cag gcc agc cag agc cat ctg cac agc agc ccg gaa gat aag      97
Pro Met Gln Ala Ser Gln Ser His Leu His Ser Ser Pro Glu Asp Lys
            20                  25                  30 cgg gca ggt ggt gaa gag tca cag ttt gag atg gac att taa              139
Arg Ala Gly Gly Glu Glu Ser Gln Phe Glu Met Asp Ile  *
        35                  40                  45 gggaccagcc ataggacgca gtgatgcttc tgggcccctg gggcccttgg gaggagagcc   199
acagcagtca ggccttgtac ccggcagaca ctgggtgtgg atcggccacc cagtcctgct   259
cctcactcag ggcacctgct ctgccttcca ttttgtgaat accagcacat acctccttgt   319
gcctctgttg atactgagct gctactccag gggaatgact ctcacctaca ccctccctgc   379
atcaagcgcc agcgagtgga cacagaggag tctgtcggaa tgatctggca attctagccc   439
caacctctgg agcacaccca ccttacctta ggttggggta cctgggaaag ccacccttta   499
cttctttccc tgagaggaaa taaaagccac atttacccta ggcccacagc cgggccctgt   559
ctgaactgtt tccaagttga tatgatgaca ccgtttactc tctg                   603

<210> SEQ ID NO 429
<211> LENGTH: 20
<212> TYPE: DNA
<213> ORGANISM: Artificial Sequence
<220> FEATURE:
<223> OTHER INFORMATION: Antisense Compound

<400> SEQUENCE: 429
agtaaacggt gtcatcatat                                              20

<210> SEQ ID NO 430
<211> LENGTH: 20
<212> TYPE: DNA
<213> ORGANISM: R. norvegicus
<220> FEATURE:

<400> SEQUENCE: 430
atatgatgac accgtttact                                              20

<210> SEQ ID NO 431
```

```
<211> LENGTH: 20
<212> TYPE: DNA
<213> ORGANISM: R. norvegicus
<220> FEATURE:

<400> SEQUENCE: 431
aattcctgat ggagtgtcgg                                                   20

<210> SEQ ID NO 432
<211> LENGTH: 21
<212> TYPE: DNA
<213> ORGANISM: Artificial Sequence
<220> FEATURE:
<223> OTHER INFORMATION: PCR Primer

<400> SEQUENCE: 432
catcgtgtgg agcactacca a                                                 21

<210> SEQ ID NO 433
<211> LENGTH: 23
<212> TYPE: DNA
<213> ORGANISM: Artificial Sequence
<220> FEATURE:
<223> OTHER INFORMATION: PCR Primer

<400> SEQUENCE: 433
cctgcccagt atgatcactt tca                                               23

<210> SEQ ID NO 434
<211> LENGTH: 23
<212> TYPE: DNA
<213> ORGANISM: Artificial Sequence
<220> FEATURE:
<223> OTHER INFORMATION: PCR Probe

<400> SEQUENCE: 434
cagggccttc ctgggaggag tcc                                               23

<210> SEQ ID NO 435
<211> LENGTH: 20
<212> TYPE: DNA
<213> ORGANISM: Artificial Sequence
<220> FEATURE:
<223> OTHER INFORMATION: Antisense Compound

<400> SEQUENCE: 435
gttcattcta aagtggtcac                                                   20

<210> SEQ ID NO 436
<211> LENGTH: 18001
<212> TYPE: DNA
<213> ORGANISM: M. musculus
<220> FEATURE:
<221> NAME/KEY: misc_feature
<222> LOCATION: 17923-17801
<223> OTHER INFORMATION: n = A,T,C or G

<400> SEQUENCE: 436
gatgttggac tttataaaca ggcccttccc tgaaatcgta gttccaggaa atctggggcc       60
tctagaacaa ccaaacaagg caaaaagcaa aacccctttc aacatgcttc tcccaaaggg      120
aggaaggtgg cccagtgtgt tctctcaggc cagcccggac aacagtgaga acagggttct      180
ggccctccct cggctgtcaa cttgggatcc tcctagggct tcagcctcct cacggtcggg      240
attataggca tttcctacca tatggagatt gattgacaca gacactgtaa ccgattggac      300
```

```
atgcattttc ccttccctcc ctagtgacta ccagacaaag tgctggagtg gaacccagtc    360
caagtactat gcggatcttt gaccggttaa ctctaatcct cccagcccac agtacgcaga    420
gcttcgatcc tgcccattcc tcatcagatt tatattcggt tcctagctgg ctggctaggt    480
ccctcttact cttccactac tccttccaag tccaggaatg tgcgctgtgc agccgctgct    540
ctgactccta aaaactgtaa aactgtaaaa gctgtagaaa cgttaagaat ggcgaaggat    600
cagcccaccc tttcttctct gaggatcggc ctgggatcga gaggtcacat cctaatatag    660
aaagcaggcg gtctggtgcg ctgagacgct gccaccaaat cggagagttc tgccaccgtc    720
atccctacct agatcttccc agagtctcgg ggaggaacca gggaacccaa ggggcccaca    780
ctggggttcc tgcactggag aggacagaag ctgcctaggt cagcagctgg ggaaccactt    840
gcaggcagcg ggctggggct gggtggggcc gggcggaccg caagtctcag ggggcgtgga    900
gcccaggcgg aaggggcggg ccgggcacga aagggctgg gccgaggtgc cgcggggttg    960
ctggagggtc gtgggcggcg tgcaggagac atgtcggcgg gcagcagctg cagccagact   1020
cccagccggg ccatccccac tcgccgcgta gccctcggcg atggcgtgca gctcccgccc   1080
ggggactaca gcaccactcc gggcggcacg ctcttcagca ccaccccggg aggtaggcgc   1140
tggccggggt cacgggcgac ctcggggggc tggaggatac gtcggatcc ggagtctcac    1200
gtgcgacggg gagggcggca ttcgagggt tcggtagctg ccagaacgg acgaggggcg    1260
tcgggaaagc agaagggtca ccgtctcggt tgctcgcctt ctgggtgtgg tggagcgtgg   1320
tctggaaccc ggctgcaaac tgcctgcatt attagccttt tcctgggaga tacggcagag   1380
tgccctgagc atacagatag gcactctgcc aggaccacca tgtgcttaag ggcgacctct   1440
gtgggtgtca gggcagtttg gggtgggaca agatcaggga aagaggctgg cctggagatt   1500
aagtttagtt gatctccctt ggaataagtg acgcctgcac acttttttt ttttaacct     1560
ttccggaggc agccctcttt gctttggaca ctcgctcatt aatggaggct ggacgctgag   1620
ggtgcttctc tgccacctgt ggcttgtgtt aagagagaga ttcctgcagg ggcggcgtct   1680
ggtgtagtgc agaacaacac gttcctcggg cctgggggc agggcacagc gttgaactgg    1740
cccaagtggc ggaggatgag gaagaggaag ctgagttggc gcgggtgggg gccggcctcc   1800
gggaaccagg cattcccagc ttgccctgga gccccagtat agacgctgat gaaacctacc   1860
cgcctgtttg catgatgaaa tcctcgtggc tcactacttc cctcccaatc ctcgcgccgc   1920
tcccacccac ttttgcgctt ctccccctccc cggtctcctc cccaactac tcctcttaca   1980
actcaaaaac aagaggaatc ctggcgcggt gatgaacctt gggctactgc tggcgcagcc   2040
gggccacatg cctatttcct cgggcagctg tccctgcacc agggagcaca gccagatccc   2100
agaaccaagg caccgatgaa gggatcttgg agctcagtca gtgtccactg ggttctgtga   2160
tcttcaggac acagcaccaa ggcctcgctg cttgagcacg tgtctgttgt gcatcgtcat   2220
gctgagttcc tacactcagc aagaagtagc aagcagggca gggggagaaa gccggctccc   2280
tcttattaga aacggcccaa aggaaaagtt ttctgcaggc ttctggcctc ccgttactgg   2340
agttcttcaa ccccgctggc cacttttag ttcacgctgt tgccccttg tcttttcgca     2400
gaactttgtg ttgagcacaa agtttcacag agagttgagt cctttaggc gaggtgtgaa    2460
tcagggtgta tttttatttt tatttttta taggcaccga tacagaccta aaggctctgg   2520
gaaacgttta ttttctctct tgcccgtccc tttctggatg aacaggttag ctgggtagca   2580
atagccagta ctgtttgtaa tgcactctga tccacttctc actgtggtct gcgaagtgtc   2640
cgttggcaga ccaggtagtt cccgttgtct ttgaaggaga aggggtttcc ttagagtgta   2700
```

```
gcatttgctt cttaactgaa agaaagcagt gtcaggtccc caaagccagc tggcccttgt   2760 cagattttg  ttgctgttgt tgttgtttgt gtgtcacaca gtccatagct cgaggaaaga   2820
cttgcttgtt tctgccaaag ccagttaatt taaggagtgg gatcttttcc caaaggccat   2880
tcattccagg tcgcctctgc taaagggcag aagcttgacc catttgctcc agaatgtttc   2940
tcatcactta gcacccccaac gagatacgga atccgagtgc agaggtctac agggtgagtt   3000
acgggagagc cagggctaca cagagatcct cctgcctcac cttactgagt gttggtaatt   3060
ccggggttaa cagctgttga ataccctttg ggctatttct cttgctctc atctattctc    3120 tgcaaatcca tctaactttt gaattttctt acttgtatca ggggccagct gggagttcaa   3180
ggtcaagtga atcaccctga ggtctatctc tgtcctctgg catctatggg cgtataaagc   3240
ccatgagctt gaattcagga ctgagatcac tctgcctaac cattatatgc ttgattggct   3300
cacattccat tttgagtact caggagttac aagggaaagg gataaacaac acacaaacaa   3360
agcccataca cgcacacaca cacacacaca cacacacaca catatacaca tatatgtata   3420
cacacacaca cacacatata tacacatata tgtatacaca cacacacaca tatatacaca   3480
tatatgtata cacacacaca cacacacaca cacatatata cacatatatg tatacacaca   3540
cacacacaca cacacacaca cacacacaca cggctttttt ccttgccttt ccagatcttt   3600
aggagtctgg caaagtagat ctcatatcca ggcataaagt caggtttctt gaacttaagc   3660
ttcctatact ccttggcatg tgacttgacc tgtaagggc tgcaagctct acatgaagaa    3720
atactacagg aagctacttc agctgagaat ggctttgaag cagctgcctc tggagaccag   3780
ggcacaacag gtggcctgaa ccatctccat tcctgggact ctggtcagtg gtcattaagc   3840
ctttggtaac ctaggacatt tctgaaggga gtgtcccaca agaagatttg aacctgggag   3900
tctttaagat tgctagcaat gtcataaaca ggatctagtg aacacccacc aaggatggat   3960
gtttgacttc taaacctaca gaagttgttt gggtggtcat acctcatagt acctgggtaa   4020
ggttaattaa taatcaggca ggcaggtagg tagggtggca ggtgtaaatg acactgtttt   4080
gtaaggggta aagttgaatg taatggtgca gagacaggag aatctttgtg agtttgaagc   4140
cagcctggtc tacagtctac ataataagtt ccaggtcagt cagacctaca tagcgagacc   4200
ctatcagaga aattaaaaaa aaagtctctg tctgggaagc tgaccttgag gtggctgcca   4260
agtgtttaac tccgtcagtg ctgggaagag gggaggtggg ctggacgctg atgccggtga   4320
cttgatgtcc cgaggtctta gtcacacaga ggggagaagt tacagctgag gatattatta   4380
agggccgaat gagagagctt ggatatcgag gtggcaagga gataatggtc cccgtctgac   4440
atgcacccga gcttccattt aaagtgtttg aaacaatata tagtaggttc caggacatac   4500
gactgaattg gaagggggtt gggtagagca ctccaagcta cctttgcagc ctcttggttt   4560
ttatttaagg catgccctgc aactaggaag atagtgtgac ttggaaggat gggattcagg   4620
tgacgataca gctgacggtg ggatacaagc atgggctta  agagatggtt ccgaggttaa   4680
aacatgcttg ctagccaggc gtggtagtgc aaaacaaaaa accaaaacag caaaaaaaaa   4740
gtgcttgctg cacttgggaaa ggtctgttct ttagccctg gacctctgtc cgtcatcatt    4800
ccaccatcat tctagctgaa ggggtggcct ttccttgctt ccacaggaac ctctccctaa   4860
attaaaataa aagcctagag gctcggaggg ggaagctcag tgaaggggaa ctctgcaaga   4920
ggatctgaca tcacaaagga gggggaggag ggcggaggc  tggagggtga ctttcaggtg   4980
taagagagag tggctatgtt gggagttagg ggactagagg tttggcacag actttcagtt   5040
```

```
atgagagggg taaattccag gggtgtactc atcagtggct ataattaact ctgcagtgtt    5100
tactagaaat cagctcaggg caactgtagc catatccttc cgtacacagg cagacatccg    5160
agagacgtag gctggttgct ctaattgtgg gatttatttt acatttccta gtgtgacagc    5220
agatcatcac attctgtgta ctccgactag gtgcttctgc ctccttttct ctctctctat    5280
gtctccctct cctttccttt ttctctcttc ctcctcttct ttaagatagg atcttactgt    5340
atatagcccc ggctagcctc aatactggtg atctcctgtc tcagcctcct gagggctggg    5400
ataataggca tgtggcatct tgcttaagtg cgtaagattt ttatttgcca gttttactta    5460
atagttcagt gatgctgagg ggagacatga ttctaagaac caggggcaca tctatagaat    5520
gcagcgattc catagacacc ccctgcccct cagttctata acccatagtg atttttttttt   5580 taaagtttta tttaattata tgagtacact gttgctgtct tcagacacat cagaaaaggg    5640
cgtcagatcc cattacacag atgattgtga gccaccatgt ggttgtggga tttgaactca    5700
ggacctctgg aagagcagcc agtactctta accactgagc catctctcca gcctcatcca    5760
tagtgatttc cctttgtggt tttgtacgtg ggccccaggg ccacagaact tgtccccatg    5820
atccatggca gtctgaggac gtgatcctct agattttggt ggccttcaga ggttgccttt    5880
ttctttccag catcccccca aagtggcagg tagtcattat ttacaaggtg agctggattc    5940
tcacccacca ctatcagcaa aagtcattac cgactcaggt gaagggaggc agagagcatg    6000
gtgctgattt catttcactt agtggtacaa aacactgaag cattttttcca aatgagcctt    6060 tatttgatgt tcacgaaaac gagttagaag ggagtagcaa tattgaaaat gaggattgct    6120
taacgcgacc atttttttttt gttttttttt tctcccctcc ccttagcgat catttctgtg    6180
tatggatccc catatgttca ggcaaacaaa caaaaacatc cattactttc tggcccgagc    6240
gagtcttacc tcagctgtct ttctccgtgg tgaatcatag ccacgagtct gttggcgtgc    6300
ttgtttctcg ggttagacag gatgttcttc cagagcagtc gttgtgaccc caggacctaa    6360
ggccaggtcc ggtgttcaga aggtgacgag tcatgctgcg tgtggcttag tggcacagtg    6420
ccctgctagc atgtgggatg ccctgggctg attttttagca ctagggagga gatgaagatg    6480 aaggggggcct acaaggaacc cagagtgaag catcctctta ggatatgtag gttccttcct    6540
gaggcctggg tctcccctga gaactccagg gtggagatgg ttgtaccagg ttgccactag    6600
cctttaacaa gccatcacca gacttgataa cgtaaacaac ggtttattgc tcacgtctgt    6660
cctttgctga ttttggcaga gttgactcaa ggctgcagct ggattgccct gggctgcaag    6720
gtccaaggtg gccttatcca cgtgtgagtc tatcacttgc tggcccctgg tgggaggctg    6780
ggaacgctcc cgtcttgggg ctcaaatcat ttagtttagc ttgaacttct ctgttagccc    6840
agggcagagg catgggagct tgccccatc actttaaaag tattcgtgtg ttcttagggg    6900
gcagtccagc tttaagtggg ggtgagagga agatggggtg gccttctttg ttttgagaca    6960
ggatctccaa acatttgagg atgaccttaa agtcctgatc aatctactga taacttctca    7020
agcgtatgaa ccactcactg gttttgttg ttgtttgttg tatgttttttt gttttgttttg   7080 atttttttttt tccctgcttc ttctgaacgg cagactttag ggccattgct ttgtagggct    7140
tatgcttact gtccaaacac acccctctta ttgtcacttg gaaggcctgg gttttctggg    7200
cactagcaat tggcttgagt caggtgtgcc cggcagccca gaatgtggat gagaaaagag    7260
gcacagtccg tttagagctt cgggggcaca tgtttatgat gtcagtaatc tgggaatgag    7320
gagttcgtca acaggaggat cagatgttca aggccaatgt gggtgctttg agaatggctc    7380
ccagagatgc atgcatttga atgctctgtc cccattcggt ggacctgttt gggaaggatt    7440
```

```
aggaggtgtg gccttgttgg aggaggtgtg gcattgggat gggctttgag gtttcaagaa   7500
aaggaaaaag gaaaatgtcc acaccattcc ctgttagctc tctctgtctc atacgtgtag   7560
atgaatatga aagctaacag ctatggctcc actcagcacc atgcctgcct accagatgcc   7620
atgcttcccg ctgcgatggt catggactct aagctccacg ttaaatgctt cattttgtaa   7680
gttgtcttat cacaacaata gagaagtaac cgagacagcc ttagctacat attgcatttg   7740
agggtggacc gggcaggctc agctcacatg aaaccttgtc acaaaacact ccaagaaatg   7800
atcagagcgg tcgtcctact tgaagagaat gtgtgtttgg actggagttg tcgctcagtg   7860
gaggaacaag tgtgtttgga acctgggttt aatcccaagc accagaaaag gaaaacccg   7920 gccagtctat cttagtgtgc tacagctgcc atatgaaaat actgctttaa tcctagctta   7980
agcggcaaaa cttattttct tactgtttgg taactggaag tttaagacca gagtgaggtt   8040
ggttctttct gaggcctctc ttcctagctt gcctatcttc tctcttgtca gcttatggtc   8100
ctcctcctcc tcctcctcct cttaatagta tagaatagag tttattcagg gcatggggag   8160
ggtagtagag acagagaaag gcagagaggg agagagtaga tgccgccatg agcatgtgga   8220
gcgagagggg ggagggggaat ggggagagag ggggaggggt gagaggacag aaccagagca   8280
agaaggcaag agagccagct tatggtcttt cgtctgtggg tctatgcatg catttcctct   8340
tctgaggatg ctctggtgac gccagatcag gatccagtct aaagggttca tattgacctt   8400
ctctataaag acaccatatt gtgaggtgct ggggtttagg cttcaacacc tgagtttgaa   8460
ggaacacagt acagtccata acagctccca cccactccct ctggactagc ccttgctgtg   8520 tttttgggaga cacctggaga gcttgtggca ctcacactct gcactggtgc attctgaagc   8580
atttggggag aggtctgcaa aggggggagac gctgggccag ccttagaaag atttcagcca   8640
ttttgttcta aagtctctgt aaaaagcctt gctcttgtca gagcctctta gggaagaagg   8700
gtggcttgtt gcccccgaca gattgcccac agttggtgtc tggtagcttc ataggacccc   8760
cgagagaggt aggtgtgcat caccgtgcct ctcttcctat tccttcataa aagtcttctt   8820
tctgataagt ttactctgct tgcttgagac tggacatcta tctatccatc catccatcta   8880
tatatcatct gtgtgtgtgc ttgtgtctat ttgtctgtct gtctgtctgt ctgtctgtct   8940
ctatctatct atctatctat ctatccatcc atccatccat ccatccaacc ttccatcctt   9000
gtgtctacta tctctatgtc tgtctactta tgaaacggtg tctctacata gtcctggctg   9060
tctcagaact cactctgtag gggactggcc ttgaacttac agagatccaa ttggctctat   9120
ctacggagca cttgtattag agaggcatat accaccatgg ctggcttatg tttgtttatt   9180
tattttagat ttatttatta tgtgtaagta cactgtagct gtcctcagat attccagaag   9240
agtgcatcag atttcattac ggatggttgt gagtcaccat gtggttgctg ggatttgaac   9300
tcgggacctt cggaagagca gttggcgctc ttaaccactg agccatctcg ccagccccat   9360
ttatttattt tttgatcccc aaacccttgt gcatgtaatg taaggaagat gttcttccat   9420
ggaatgataa ctctagcctc gggaacattg gtatgtgtta tttatttagt cttttttttt   9480
tttttttttg agacagggtt tctctgtgta gccttagctg tcctggagac caggctggcc   9540
tagaactcag aaatccgcct gcctctgcct cccaagtgct gggattaaag gtgtgcgcca   9600
ccacgccggg cttatttatt tagtcttgat gatactcctt tggggtgtga gtcttttctt   9660
accttcttcg tgtggctcag aaagagctgg gaccagaaaa ttgagttttc taggtaggtg   9720
attcccggtt tgagtccagg acttgtgcac aaagtcccat gtggtttgca cattaaggat   9780
```

```
cctaaaaata ggtggtgatg gccagtgctt taaatatagt gtccgtgagc ccagggtgac   9840
acccttggtt ggcaggtgag aaaactagat ccttggggga atgtgtcctc actagtgtgt   9900
ccaggaaaac tggcacgagt gttaaaccac gccttcctgg ggagtaagca ctgatctata   9960
cttcgtgcat tccaggaatt aaaagttcca aaggctacca ggcatacctc aattcatgat  10020
ggttcccata ttctgtgtgt ctgagagaga tggaggacgc ccgtttccgc accccaagtc  10080
tctttcttgg ttgcttacct tccttctgaa gagtccccac tttgggtcct tggaattggg  10140
tcctgctgtg ggtgggactg agcaactggt ggcagctggt caccttaaac cttgatggga  10200
cagaataatt gttagcgttt gtgcaggggt cccttgggag ggccacagtt ctttttttt  10260 tttttttaaa ggatttattt atttattata tgtaagtaca ctgtagctgt cctcagctac  10320
tccagaagag ggcatcagat ttcgttatgg atggttgtga gccaccatgt ggttgctgag  10380
atttgaactc aggaccttcg gaagagcagt cagtgctctt aactgctgag ccatctcgcc  10440
agcccagggc cacagttctg atgcacacca gaggttgatg aagttgccat gataataaat  10500
gagcaggccc attttgaggc cttggagagg ccactgaggc acaggtagag gaagtagtac  10560
cttgtccata gagtagagct ggcaaatgag acaattgtct gtcgagagtc agcgagaaag  10620
aacgttggtc cacaggcagt tcaaatctga acttggaact ttcaccttag cacccagtag  10680
gctctcgatt ccagctccac aactgatctg tgattcacgg tgtgtgtgtg tttactacct  10740
acctcaacat tatttatatg tttatttatt ttgtaccttc ttttctccac tgcgaccgga  10800
tccctgacgg ggaaacttga aggcggaata tttattttgg ctcctgactt ctcagttcag  10860
tccagtcagt tgattcattg ctcgatcaga acatcatggc ggcaggagct tgtgttagag  10920
atgggtcttg actttagggt gggcaggaag cagagagaag ggagatgctg gcgcctggct  10980
ggcttctaaa cagtgagatg gtgctacctg catggaacat ggtctatcct tagttaatcc  11040
tccctgcaaa tgacctcagg cactccacag ctgcaccttc ccagggtcct acatattttt  11100
ttggaaatag cgcctctctt atttagcccc gtctattctg gaaattgcca tgtagaccat  11160
gctggcctcg aactcagatc ctcctgcctt tgcctcctga gtgctgggta gtggcaccac  11220
acctggccag caggacctct taaacctttt ttgttgacct cttctatcta gcatgagttt  11280
ttatataacc caaggtatgt aggtatataa agtaggtatg catatcaaac attcactgat  11340
aaagttgtaa atttatttta aaaaaaacca ttttttgggg ggcatacata taatttgact  11400
gtctattaac tgacaaaagc cagtttgcat actaagatga ccttcttgtt tacgaagaat  11460
agtgtcccgg ctgaaagtct cgaaccatag gacacagggc atattcgttt ttcagttggt  11520
tggcgttttg tttttataac aatctgtgat gtgcattatg ttggtaaatt gtattgcgct  11580
gtttgggatg actgataagc tggctgtatg cacagagtta ccgccccgcc tctcgcttca  11640
gacccaagtg tgtttatctc agtgtctgcc ccctgtgtga ccagagggaa gagagcgggc  11700
ataacgacag ggtgaaaatg cccttgagaa cagctggggg gggaaccact gacaaccagg  11760
gtccttattg tttgtgccac gctatggaag tgccttagtt ggaaacttga tctacatggc  11820
aagctccaga tagaaagacc ctgcgtagga ccctgggaag gcacaacaca gctgtgggag  11880
tgcctaaggt catttgcagc gcaggttagc tgaggataga ccctcgctca gtcgggctc  11940 cagctgcctg cctcggtttc ccttactcag attctgccgg atgctgtgga cctacagctg  12000
aatgacgttc gtttccggtt ggctaggctc acctgtttga agccttgccc cgaggggacc  12060
attgactcca gctggctgcc ttagagtcct tctctgctga atgtttggct ggtttaatac  12120
tgtttgtctg acctgtctgc ctacccatct ctcgctagct atctattctt ttaattcggc  12180
```

```
tttactatgc acttatttac aatggaaagt tttcgtaggt catcctccca ggtggtacaa   12240
aaccatcatc agcaccagga aaagccgttc gtttaaataa ataagtagaa gacagtgaca   12300
gtgacatttc agaagctgtc agcaattctg tcctaatccc aagacttact tatttattta   12360
tttttatttg agacagggtt tctctgtata gccctgtctg tcctggactc attctgtaga   12420
ccaggctggc cttgaactca gaaatcctcc atcctcctgc ctctgcctcc caagtgctgg   12480
gattaaaggt gtgctccacc atcacccggc tgattcattt ttaaaacatg tatttatata   12540
cttattgaga gggagggaga aggagtgggg gaagagagag agagagagag aaagagagaa   12600
tatatgaata agagtaggta taggtgtggg ggcatgcatg ccacatcttg catatggtgg   12660
ccagaaggca tcttgtgaga actgattctc gcctaccatg caggtttccg gttgtgaact   12720
cagggcccca ggcttggtgg caggtaggtg cctttgccag ccgagccatc tagccagccc   12780
ttaatttatt ttcagtacgc gtggtataga acattatata atacgtagct aatgctgtat   12840
agtctctcta taaaaaaaga aactgccgtt gtgtttgaga aaccagagtt atttgtcatc   12900
tgcaaaggga tagctataaa tagaaaggca aaggcggttt taaaattcca gctggctgcc   12960
attgtctgct ggaggcttgg ggcctaacta aggcttgagg tttgttggga agaaagcctt   13020
cagtaagtgc tagtgagggg ttaaaaatag atcatcagtg ctgcactgtg ttcgaggccc   13080
cggggtgggg gacctgcgga taagctcatc tgctcactgt cacctgatgg gtctccctcg   13140
acgttcctgc tccctcctta cattgggaat cgctcccttta tatggtggtg ttcaggcggc   13200
tgtcagggtg gagggtcctg agtgtggttt actgctggag aagaggtcac tgagtctgac   13260
cctcaccctg ggcataagat gaacatggtg taggaggtca ggaggaatgg gactggcgtt   13320
catttcatgc cagcccttaa agggtgatgc aggcagaccg atgtagtgag gtttggagaa   13380
aggctcagcc taagtccttt ttggattgga tagaacgttt cctgtttcgg cgaagacccg   13440
gcaggaagaa agtctcctct gcagagaggg acccactgtc tttctgttgt gtagatggtc   13500
gacctaccgg agttctgtag gatgggatga tgcggtgaca gggtgaccac cttttctgtg   13560
tgccgtgctt gtccctgtgt aattgacaag gagaactgag ggatgagagg ttgagggact   13620
atagcatagg gtgttcagag ctccgagaaa acaaagatgc atcttagtgg gcaacaaaca   13680
cctccatggg ggaggggggct ccccacgtgg tgttgggggt taggcagtgg agcagggatg   13740
tggtcaggtt ggccaggtcc ctcggtcagc ctaatccccc tttggtctag attctataaa   13800
ggaccctgct gcatcggttg tggccactcc ttcacaggaa gtgggaaaca caacaggctt   13860
ggggttccag gaagtcttac cggctccctt attcaccctt ccccaccagg aaccaggatt   13920
atctatgacc ggaaatttct gatggagtgt cggaactcac ctgtggccaa acaccccca   13980 aaggacctgc cagccattcc tggggtcact agccctacca gcgatgagcc tcccatgcaa   14040
gccagccaga gccaactgcc cagcagcccg gaagataagc gggcaggcgg tgagtcctgt   14100
ccaggtcctg aactggaagg aggattgtct gttctcagga attccacatt tcagggagag   14160
ggtgatggtg gctgtccacc ttttgaggag cagctgtaga gagacaagag ggtgggggc   14220 gggtgggaag tgggactctc tttggtggag ggtctacaag ctccaaggaa ctcaaagatc   14280
tcatgcatca ggtaattagg aggagatcta aaatgacagt ggctttctcc agcaccttcc   14340
atcggcccct ctccctgtat catcgctcac aaagtaccac tcttagaacc cagcagctat   14400
ccctgagttc ttgatgcaag gagacaattt atcagatatc atgcggtgta cttccttccc   14460
ctctaggaaa ttacatgtct gcaagataaa aacaataaac ctgggtacct cctggcacgt   14520
```

```
ttactggtca ttaaatggat tgtggatgga gacaggcaga caatggctcc tattgtcacg    14580
gaagctttga catttatatc taggtctttc ctggtttccc ctcctcccaa aaacaatcaa    14640
aacagccacc ctgccaggca gtgggagcga gttgtagtgg cagaacacct gagctctcca    14700
ctgtgggact gggttgcaca agcatgttca catcctcttg gtctggggc cacctctgac    14760 tctccaccct gaaggcagag ctcaagtctc agacagggag ctgatgacac ccccatggc    14820 cctgtaggtt gtgattcctg tagctgtctt cagacactcc agaagagggc ctcagatctc    14880
attactaatg gttgtgagcc accatgtgtt tgctgggatt tgaagtcagg aacttcagaa    14940
gagcagtcag tgatcttaac cgctgagcca tctctccagc ccctgggatt tctaattacc    15000
ccaggagttc agcagcccaa gacaaacaat atttattctg ttagactgag atggacatgg    15060
ggaaagtgaa tagcaataag aaggcagatt tgactgcctg cagagagcga tgtgacaagc    15120
ggttgccaag ctacacgtgt gggtccctgc agtgtcttca agggtggagg gattccccag    15180
tctttgcaca gaactctcac ctttaccttc ccacctcaaa ccaaagatga tagaggatgg    15240
agttgtgacc gctaactgaa ggctgtcatt taccccttgct ggcacactga cgacagctcc    15300
tagattctga tggtatttta gctctcaacc ctcaagagtg gcttggttgc cccatagagt    15360
taggtggtgg tagtggtgtt ggtgtgggtg tacttttaaa tttccttaac tggacacagg    15420
acacaaagct ccaccccttg gaccacgtat taaaaatcgg attcatggga aattgagcag    15480
tgtcactgcc ctcctgagga agctgattcc taagcccagt caacttctct tgtttctctt    15540
cctcagcatg ctctttccag ttgacctgtg agaataacaa agatgacac ctctctctgg    15600 actcctaaga ctggagcggt tccatttgcc acttgtttat tggctgtctg tctcctctct    15660
ccacaggtga agagtcacaa tttgagatgg acatttaagg gaccagccgt aggacgcaat    15720
gatgcttcta tgtcccccaa ggcccttggg aggagagctg cacagcattc aggcctcata    15780
ccaggcagac actgggtgtg ggtcggccac ccagtcctgc tcctcactca gggtgccagc    15840
tctgccttga atttttgtaa caccagcaca tacctccttg tgcctctgtc tataccgagc    15900
tgctactgca ggggaatgac tctcactcac accctccctg catggagctc cagcgagtgg    15960
actcagagga gtctatcaga atgatctggc aatcctagcc ccagcctccg gagcacaccc    16020
atctttcctt aggctgggtt acctgggaaa gccacacttt tacttctttc cctgacagga    16080
aataaaagcc acatttaccc taggcccgcc cacagctggg ccctgtctga actgttttcc    16140
actcgaaatg acgacatgat tactattctc tgtccagtgt ttatggtgtg atttccctgt    16200
acaatatttt ttaaaaagat ttattttatg tatatgagta atctatctat ctgtctgcct    16260
gtctgtctgt ctatcatctt tctatcatct atttatctat ctatctatct atctatctat    16320
ctgtctttct atcatctgtc tgtctgtcta tctatctatc tatctatcta tctatctatc    16380
tatctatcta tctatcatct gtctctatct atctatctat ctatctatct atctatctat    16440
ctatctatct atctatctat ctatctatct atctatcaat catctgtctt gtctgtctgt    16500
ctgtctatct atctatctat ctatctatct atctatctat ctatctatct atctatctat    16560
catctgtctt gtctgtctgt ctgtctgtct atctatctat ctatctatct atctatctat    16620
ctatctatct atctatctat ctatctatct atctatctac tatctatcta tatagatggt    16680
agtgagccat catgtggttg ctgggaactg acctcaggac ctctgctcgc tccgaaaatt    16740
tatttattat tatatgttag gtagactgta gctgtcttca gatgcaccag aagagggcat    16800
caggtcccat tacagatggt tgtgagccac tttgtggttg ctgggatttg tactcagaac    16860
cttcagaaga gcagtcagtg ctcttaactg ttgagccatc tctccagccc cctttacatt    16920
```

```
atcatatgtg cttgttatac cagcactctg ggtcagcaga gcatgcctta ctgtcaattt   16980
acagctgaga ggtctggctg aagctagccc tctatgggcc tggaccagaa cgctgcaggt   17040
ctgtaattat ttttagtagc agcaagtgtt acctttgtcc agtgagatgg tcaccttttcc  17100 tctgagcctg ggccagtgta gagccttcgg tccacatcag aacagtatgt caatcatctc   17160
tgtgtgtgct gctgtggggg gtgcagagga gataatagat aataggattt tactgaggta   17220
taccatgtac ccattaaaaa aggtagcatg aagtcaattg cataggattg gttcccagtg   17280
gtccatgtgt ggtgagttgg gggggaagag ggtggagctt gggggaaatg gtttagctag   17340
gaatgagagg aggcagacac ccagtgttac aaaagtcaga ttgtcttgtg gagccaaggt   17400
gagtaaggtt ggggtgtctc agatcccttt agggacacca caggtacttt tgtgtgtgaa   17460
tgtgacttac aattgttaaa gaaagagagc cactttatg agtcttgcct gcggactga    17520 gtctggtgtg gcaggtgtct catgacagga cctgctgagg ggtgggtccc ctggatccag   17580
agacagtggc tgatcaggag gcagtgccct ttgtaggttt gggatgatag tgtttcatta   17640
gcttgccatt ggaggagtgg caggcctcag cggccagatc tttcacttgc cttctccaca   17700
gcccttgcca aaggaagcag agtccatgtg gaaatacagg aaaggatgta gcactttgct   17760
gtgttggctg catacacaca gcctatcctc ctctgagtgt gagattagga gtctgttgag   17820
gggataccac cgcaggaaaa tttcatctag gttaaatgag agattaagtc aacatttcca   17880
gtcagcttct caatgaaagc atctccttgc cctgtcatct cannnnnnnn nnnnnnnnnn   17940
nnnnnnnnnn nnnnnnnnnn nnnnnnnnnn nnnnnnnnnn nnnnnnnnnn nnnnnnnnnn   18000 n                                                                  18001

<210> SEQ ID NO 437
<211> LENGTH: 15
<212> TYPE: DNA
<213> ORGANISM: Artificial Sequence
<220> FEATURE:
<223> OTHER INFORMATION: PCR Primer

<400> SEQUENCE: 437
cgggcaggcg gtgaa                                                    15

<210> SEQ ID NO 438
<211> LENGTH: 20
<212> TYPE: DNA
<213> ORGANISM: Artificial Sequence
<220> FEATURE:
<223> OTHER INFORMATION: PCR Primer

<400> SEQUENCE: 438
tcctacggct ggtcccttaa                                               20

<210> SEQ ID NO 439
<211> LENGTH: 21
<212> TYPE: DNA
<213> ORGANISM: Artificial Sequence
<220> FEATURE:
<223> OTHER INFORMATION: PCR Probe

<400> SEQUENCE: 439
agtcacaatt tgagatggac a                                             21

<210> SEQ ID NO 440
<211> LENGTH: 20
<212> TYPE: DNA
```

```
<213> ORGANISM: Artificial Sequence
<220> FEATURE:
<223> OTHER INFORMATION: Antisense Compound

<400> SEQUENCE: 440
gccacccctt cagctagaat                                            20

<210> SEQ ID NO 441
<211> LENGTH: 20
<212> TYPE: DNA
<213> ORGANISM: Artificial Sequence
<220> FEATURE:
<223> OTHER INFORMATION: Antisense Compound

<400> SEQUENCE: 441
cggcagaatc tgagtaaggg                                            20

<210> SEQ ID NO 442
<211> LENGTH: 20
<212> TYPE: DNA
<213> ORGANISM: Artificial Sequence
<220> FEATURE:
<223> OTHER INFORMATION: Antisense Compound

<400> SEQUENCE: 442
taatcctggt tcctggtggg                                            20

<210> SEQ ID NO 443
<211> LENGTH: 20
<212> TYPE: DNA
<213> ORGANISM: Artificial Sequence
<220> FEATURE:
<223> OTHER INFORMATION: Antisense Compound

<400> SEQUENCE: 443
cttccgtgac aataggagcc                                            20

<210> SEQ ID NO 444
<211> LENGTH: 20
<212> TYPE: DNA
<213> ORGANISM: Artificial Sequence
<220> FEATURE:
<223> OTHER INFORMATION: Antisense Compound

<400> SEQUENCE: 444
actcttcacc tgtggagaga                                            20

<210> SEQ ID NO 445
<211> LENGTH: 20
<212> TYPE: DNA
<213> ORGANISM: Artificial Sequence
<220> FEATURE:
<223> OTHER INFORMATION: Antisense Compound

<400> SEQUENCE: 445
tgcccgccga catgtctcct                                            20

<210> SEQ ID NO 446
<211> LENGTH: 20
<212> TYPE: DNA
<213> ORGANISM: Artificial Sequence
<220> FEATURE:
<223> OTHER INFORMATION: Antisense Compound

<400> SEQUENCE: 446
ttccggtcat agataatcct                                            20
```

<210> SEQ ID NO 447
<211> LENGTH: 20
<212> TYPE: DNA
<213> ORGANISM: Artificial Sequence
<220> FEATURE:
<223> OTHER INFORMATION: Antisense Compound

<400> SEQUENCE: 447
gaaatttccg gtcatagata                                           20

<210> SEQ ID NO 448
<211> LENGTH: 20
<212> TYPE: DNA
<213> ORGANISM: Artificial Sequence
<220> FEATURE:
<223> OTHER INFORMATION: Antisense Compound

<400> SEQUENCE: 448
catcagaaat ttccggtcat                                           20

<210> SEQ ID NO 449
<211> LENGTH: 20
<212> TYPE: DNA
<213> ORGANISM: Artificial Sequence
<220> FEATURE:
<223> OTHER INFORMATION: Antisense Compound

<400> SEQUENCE: 449
ttccgacact ccatcagaaa                                           20

<210> SEQ ID NO 450
<211> LENGTH: 20
<212> TYPE: DNA
<213> ORGANISM: Artificial Sequence
<220> FEATURE:
<223> OTHER INFORMATION: Antisense Compound

<400> SEQUENCE: 450
ttggccacag gtgagttccg                                           20

<210> SEQ ID NO 451
<211> LENGTH: 20
<212> TYPE: DNA
<213> ORGANISM: Artificial Sequence
<220> FEATURE:
<223> OTHER INFORMATION: Antisense Compound

<400> SEQUENCE: 451
tggctggcag gtcctttggg                                           20

<210> SEQ ID NO 452
<211> LENGTH: 20
<212> TYPE: DNA
<213> ORGANISM: Artificial Sequence
<220> FEATURE:
<223> OTHER INFORMATION: Antisense Compound

<400> SEQUENCE: 452
cccaggaatg gctggcaggt                                           20

<210> SEQ ID NO 453
<211> LENGTH: 20
<212> TYPE: DNA
<213> ORGANISM: Artificial Sequence
<220> FEATURE:

<223> OTHER INFORMATION: Antisense Compound

<400> SEQUENCE: 453
agtgacccca ggaatggctg                                        20

<210> SEQ ID NO 454
<211> LENGTH: 20
<212> TYPE: DNA
<213> ORGANISM: Artificial Sequence
<220> FEATURE:
<223> OTHER INFORMATION: Antisense Compound

<400> SEQUENCE: 454
tggcttgcat gggaggctca                                        20

<210> SEQ ID NO 455
<211> LENGTH: 20
<212> TYPE: DNA
<213> ORGANISM: Artificial Sequence
<220> FEATURE:
<223> OTHER INFORMATION: Antisense Compound

<400> SEQUENCE: 455
ctggttggct tgcatgggag                                        20

<210> SEQ ID NO 456
<211> LENGTH: 20
<212> TYPE: DNA
<213> ORGANISM: Artificial Sequence
<220> FEATURE:
<223> OTHER INFORMATION: Antisense Compound

<400> SEQUENCE: 456
ttggctctgg ttggcttgca                                        20

<210> SEQ ID NO 457
<211> LENGTH: 20
<212> TYPE: DNA
<213> ORGANISM: Artificial Sequence
<220> FEATURE:
<223> OTHER INFORMATION: Antisense Compound

<400> SEQUENCE: 457
gctgctgggc agttggctct                                        20

<210> SEQ ID NO 458
<211> LENGTH: 20
<212> TYPE: DNA
<213> ORGANISM: Artificial Sequence
<220> FEATURE:
<223> OTHER INFORMATION: Antisense Compound

<400> SEQUENCE: 458
gtgactcttc accgcctgcc                                        20

<210> SEQ ID NO 459
<211> LENGTH: 20
<212> TYPE: DNA
<213> ORGANISM: Artificial Sequence
<220> FEATURE:
<223> OTHER INFORMATION: Antisense Compound

<400> SEQUENCE: 459
atctcaaatt gtgactcttc                                        20

```
<210> SEQ ID NO 460
<211> LENGTH: 20
<212> TYPE: DNA
<213> ORGANISM: Artificial Sequence
<220> FEATURE:
<223> OTHER INFORMATION: Antisense Compound

<400> SEQUENCE: 460
atgtccatct caaattgtga                                                   20

<210> SEQ ID NO 461
<211> LENGTH: 20
<212> TYPE: DNA
<213> ORGANISM: Artificial Sequence
<220> FEATURE:
<223> OTHER INFORMATION: Antisense Compound

<400> SEQUENCE: 461
gaagcatcat tgcgtcctac                                                   20

<210> SEQ ID NO 462
<211> LENGTH: 20
<212> TYPE: DNA
<213> ORGANISM: Artificial Sequence
<220> FEATURE:
<223> OTHER INFORMATION: Antisense Compound

<400> SEQUENCE: 462
gtggccgacc cacacccagt                                                   20

<210> SEQ ID NO 463
<211> LENGTH: 20
<212> TYPE: DNA
<213> ORGANISM: Artificial Sequence
<220> FEATURE:
<223> OTHER INFORMATION: Antisense Compound

<400> SEQUENCE: 463
actgggtggc cgacccacac                                                   20

<210> SEQ ID NO 464
<211> LENGTH: 20
<212> TYPE: DNA
<213> ORGANISM: Artificial Sequence
<220> FEATURE:
<223> OTHER INFORMATION: Antisense Compound

<400> SEQUENCE: 464
gcaggactgg gtggccgacc                                                   20

<210> SEQ ID NO 465
<211> LENGTH: 20
<212> TYPE: DNA
<213> ORGANISM: Artificial Sequence
<220> FEATURE:
<223> OTHER INFORMATION: Antisense Compound

<400> SEQUENCE: 465
tcaaggcaga gctggcaccc                                                   20

<210> SEQ ID NO 466
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 466
tgctggtgtt cacaaaattc                                            20

<210> SEQ ID NO 467
<211> LENGTH: 20
<212> TYPE: DNA
<213> ORGANISM: Artificial Sequence
<220> FEATURE:
<223> OTHER INFORMATION: Antisense Compound

<400> SEQUENCE: 467
tcggtataga cagaggcaca                                            20

<210> SEQ ID NO 468
<211> LENGTH: 20
<212> TYPE: DNA
<213> ORGANISM: Artificial Sequence
<220> FEATURE:
<223> OTHER INFORMATION: Antisense Compound

<400> SEQUENCE: 468
gcagtagcag ctcggtatag                                            20

<210> SEQ ID NO 469
<211> LENGTH: 20
<212> TYPE: DNA
<213> ORGANISM: Artificial Sequence
<220> FEATURE:
<223> OTHER INFORMATION: Antisense Compound

<400> SEQUENCE: 469
gagtcattcc cctgcagtag                                            20

<210> SEQ ID NO 470
<211> LENGTH: 20
<212> TYPE: DNA
<213> ORGANISM: Artificial Sequence
<220> FEATURE:
<223> OTHER INFORMATION: Antisense Compound

<400> SEQUENCE: 470
ctggagctcc atgcagggag                                            20

<210> SEQ ID NO 471
<211> LENGTH: 20
<212> TYPE: DNA
<213> ORGANISM: Artificial Sequence
<220> FEATURE:
<223> OTHER INFORMATION: Antisense Compound

<400> SEQUENCE: 471
ctctgagtcc actcgctgga                                            20

<210> SEQ ID NO 472
<211> LENGTH: 20
<212> TYPE: DNA
<213> ORGANISM: Artificial Sequence
<220> FEATURE:
<223> OTHER INFORMATION: Antisense Compound

<400> SEQUENCE: 472
attctgatag actcctctga                                            20

<210> SEQ ID NO 473
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 473
ctaggattgc cagatcattc                                               20

<210> SEQ ID NO 474
<211> LENGTH: 20
<212> TYPE: DNA
<213> ORGANISM: Artificial Sequence
<220> FEATURE:
<223> OTHER INFORMATION: Antisense Compound

<400> SEQUENCE: 474
aaggaaagat gggtgtgctc                                               20

<210> SEQ ID NO 475
<211> LENGTH: 20
<212> TYPE: DNA
<213> ORGANISM: Artificial Sequence
<220> FEATURE:
<223> OTHER INFORMATION: Antisense Compound

<400> SEQUENCE: 475
gggtaaatgt ggcttttatt                                               20

<210> SEQ ID NO 476
<211> LENGTH: 20
<212> TYPE: DNA
<213> ORGANISM: Artificial Sequence
<220> FEATURE:
<223> OTHER INFORMATION: Antisense Compound

<400> SEQUENCE: 476
gcctagggta aatgtggctt                                               20

<210> SEQ ID NO 477
<211> LENGTH: 20
<212> TYPE: DNA
<213> ORGANISM: Artificial Sequence
<220> FEATURE:
<223> OTHER INFORMATION: Antisense Compound

<400> SEQUENCE: 477
tggaaaacag ttcagacagg                                               20

<210> SEQ ID NO 478
<211> LENGTH: 20
<212> TYPE: DNA
<213> ORGANISM: Artificial Sequence
<220> FEATURE:
<223> OTHER INFORMATION: Antisense Compound

<400> SEQUENCE: 478
gtacagggaa atcacaccat                                               20

<210> SEQ ID NO 479
<211> LENGTH: 20
<212> TYPE: DNA
<213> ORGANISM: Artificial Sequence
<220> FEATURE:
<223> OTHER INFORMATION: Antisense Compound

<400> SEQUENCE: 479
```
tgatggctca ctaccatcta                                               20

<210> SEQ ID NO 480
<211> LENGTH: 20
<212> TYPE: DNA
<213> ORGANISM: Artificial Sequence
<220> FEATURE:
<223> OTHER INFORMATION: Antisense Compound

<400> SEQUENCE: 480
agtctaccta acatataata                                               20

<210> SEQ ID NO 481
<211> LENGTH: 20
<212> TYPE: DNA
<213> ORGANISM: Artificial Sequence
<220> FEATURE:
<223> OTHER INFORMATION: Antisense Compound

<400> SEQUENCE: 481
caagcacata tgataatgta                                               20

<210> SEQ ID NO 482
<211> LENGTH: 20
<212> TYPE: DNA
<213> ORGANISM: Artificial Sequence
<220> FEATURE:
<223> OTHER INFORMATION: Antisense Compound

<400> SEQUENCE: 482
ctggtataac aagcacatat                                               20

<210> SEQ ID NO 483
<211> LENGTH: 20
<212> TYPE: DNA
<213> ORGANISM: Artificial Sequence
<220> FEATURE:
<223> OTHER INFORMATION: Antisense Compound

<400> SEQUENCE: 483
tgctctgctg acccagagtg                                               20

<210> SEQ ID NO 484
<211> LENGTH: 20
<212> TYPE: DNA
<213> ORGANISM: Artificial Sequence
<220> FEATURE:
<223> OTHER INFORMATION: Antisense Compound

<400> SEQUENCE: 484
cagctgtaaa ttgacagtaa                                               20

<210> SEQ ID NO 485
<211> LENGTH: 20
<212> TYPE: DNA
<213> ORGANISM: Artificial Sequence
<220> FEATURE:
<223> OTHER INFORMATION: Antisense Compound

<400> SEQUENCE: 485
agagggctag cttcagccag                                               20

<210> SEQ ID NO 486
<211> LENGTH: 20
<212> TYPE: DNA
<213> ORGANISM: Artificial Sequence
<220> FEATURE:
<223> OTHER INFORMATION: Antisense Compound

<400> SEQUENCE: 486
gtccaggccc atagagggct                                              20

<210> SEQ ID NO 487
<211> LENGTH: 20
<212> TYPE: DNA
<213> ORGANISM: Artificial Sequence
<220> FEATURE:
<223> OTHER INFORMATION: Antisense Compound

<400> SEQUENCE: 487
ctgctactaa aaataattac                                              20

<210> SEQ ID NO 488
<211> LENGTH: 20
<212> TYPE: DNA
<213> ORGANISM: Artificial Sequence
<220> FEATURE:
<223> OTHER INFORMATION: Antisense Compound

<400> SEQUENCE: 488
ggtaacactt gctgctacta                                              20

<210> SEQ ID NO 489
<211> LENGTH: 20
<212> TYPE: DNA
<213> ORGANISM: Artificial Sequence
<220> FEATURE:
<223> OTHER INFORMATION: Antisense Compound

<400> SEQUENCE: 489
acaaaggtaa cacttgctgc                                              20

<210> SEQ ID NO 490
<211> LENGTH: 20
<212> TYPE: DNA
<213> ORGANISM: Artificial Sequence
<220> FEATURE:
<223> OTHER INFORMATION: Antisense Compound

<400> SEQUENCE: 490
aaaggtgacc atctcactgg                                              20

<210> SEQ ID NO 491
<211> LENGTH: 20
<212> TYPE: DNA
<213> ORGANISM: Artificial Sequence
<220> FEATURE:
<223> OTHER INFORMATION: Antisense Compound

<400> SEQUENCE: 491
atgtggaccg aaggctctac                                              20

<210> SEQ ID NO 492
<211> LENGTH: 20
<212> TYPE: DNA
<213> ORGANISM: Artificial Sequence
<220> FEATURE:
<223> OTHER INFORMATION: Antisense Compound

<400> SEQUENCE: 492
gcagcacaca cagagatgat                                              20

```
<210> SEQ ID NO 493
<211> LENGTH: 20
<212> TYPE: DNA
<213> ORGANISM: Artificial Sequence
<220> FEATURE:
<223> OTHER INFORMATION: Antisense Compound

<400> SEQUENCE: 493
acctcagtaa aatcctatta                                               20

<210> SEQ ID NO 494
<211> LENGTH: 20
<212> TYPE: DNA
<213> ORGANISM: M. musculus

<400> SEQUENCE: 494
tgatggagtg tcggaactca                                               20

<210> SEQ ID NO 495
<211> LENGTH: 20
<212> TYPE: DNA
<213> ORGANISM: M. musculus

<400> SEQUENCE: 495
atggagtgtc ggaactcacc                                               20

<210> SEQ ID NO 496
<211> LENGTH: 20
<212> TYPE: DNA
<213> ORGANISM: M. musculus

<400> SEQUENCE: 496
cagtcctgct cctcactcag                                               20

<210> SEQ ID NO 497
<211> LENGTH: 20
<212> TYPE: DNA
<213> ORGANISM: M. musculus

<400> SEQUENCE: 497
attctagctg aagggdtggc                                               20

<210> SEQ ID NO 498
<211> LENGTH: 20
<212> TYPE: DNA
<213> ORGANISM: M. musculus

<400> SEQUENCE: 498
cccttactca gattctgccg                                               20

<210> SEQ ID NO 499
<211> LENGTH: 20
<212> TYPE: DNA
<213> ORGANISM: M. musculus

<400> SEQUENCE: 499
cccaccagga accaggatta                                               20

<210> SEQ ID NO 500
<211> LENGTH: 20
<212> TYPE: DNA
<213> ORGANISM: M. musculus

<400> SEQUENCE: 500
```
ggctcctatt gtcacggaag                                            20

<210> SEQ ID NO 501
<211> LENGTH: 20
<212> TYPE: DNA
<213> ORGANISM: M. musculus

<400> SEQUENCE: 501
tctctccaca ggtgaagagt                                            20

<210> SEQ ID NO 502
<211> LENGTH: 20
<212> TYPE: DNA
<213> ORGANISM: M. musculus

<400> SEQUENCE: 502
aggattatct atgaccggaa                                            20

<210> SEQ ID NO 503
<211> LENGTH: 20
<212> TYPE: DNA
<213> ORGANISM: M. musculus

<400> SEQUENCE: 503
atgaccggaa atttctgatg                                            20

<210> SEQ ID NO 504
<211> LENGTH: 20
<212> TYPE: DNA
<213> ORGANISM: M. musculus

<400> SEQUENCE: 504
tttctgatgg agtgtcggaa                                            20

<210> SEQ ID NO 505
<211> LENGTH: 20
<212> TYPE: DNA
<213> ORGANISM: M. musculus

<400> SEQUENCE: 505
cggaactcac ctgtggccaa                                            20

<210> SEQ ID NO 506
<211> LENGTH: 20
<212> TYPE: DNA
<213> ORGANISM: M. musculus

<400> SEQUENCE: 506
cccaaaggac ctgccagcca                                            20

<210> SEQ ID NO 507
<211> LENGTH: 20
<212> TYPE: DNA
<213> ORGANISM: M. musculus

<400> SEQUENCE: 507
acctgccagc cattcctggg                                            20

<210> SEQ ID NO 508
<211> LENGTH: 20
<212> TYPE: DNA
<213> ORGANISM: M. musculus

```
<400> SEQUENCE: 508
cagccattcc tggggtcact                                              20

<210> SEQ ID NO 509
<211> LENGTH: 20
<212> TYPE: DNA
<213> ORGANISM: M. musculus

<400> SEQUENCE: 509
tgagcctccc atgcaagcca                                              20

<210> SEQ ID NO 510
<211> LENGTH: 20
<212> TYPE: DNA
<213> ORGANISM: M. musculus

<400> SEQUENCE: 510
tgcaagccaa ccagagccaa                                              20

<210> SEQ ID NO 511
<211> LENGTH: 20
<212> TYPE: DNA
<213> ORGANISM: M. musculus

<400> SEQUENCE: 511
agagccaact gcccagcagc                                              20

<210> SEQ ID NO 512
<211> LENGTH: 20
<212> TYPE: DNA
<213> ORGANISM: M. musculus

<400> SEQUENCE: 512
ggcaggcggt gaagagtcac                                              20

<210> SEQ ID NO 513
<211> LENGTH: 20
<212> TYPE: DNA
<213> ORGANISM: M. musculus

<400> SEQUENCE: 513
gaagagtcac aatttgagat                                              20

<210> SEQ ID NO 514
<211> LENGTH: 20
<212> TYPE: DNA
<213> ORGANISM: M. musculus

<400> SEQUENCE: 514
tcacaatttg agatggacat                                              20

<210> SEQ ID NO 515
<211> LENGTH: 20
<212> TYPE: DNA
<213> ORGANISM: M. musculus

<400> SEQUENCE: 515
gtaggacgca atgatgcttc                                              20

<210> SEQ ID NO 516
<211> LENGTH: 20
<212> TYPE: DNA
<213> ORGANISM: M. musculus
```

<400> SEQUENCE: 516
actgggtgtg ggtcggccac                                                  20

<210> SEQ ID NO 517
<211> LENGTH: 20
<212> TYPE: DNA
<213> ORGANISM: M. musculus

<400> SEQUENCE: 517
gtgtgggtcg gccacccagt                                                  20

<210> SEQ ID NO 518
<211> LENGTH: 20
<212> TYPE: DNA
<213> ORGANISM: M. musculus

<400> SEQUENCE: 518
ggtcggccac ccagtcctgc                                                  20

<210> SEQ ID NO 519
<211> LENGTH: 20
<212> TYPE: DNA
<213> ORGANISM: M. musculus

<400> SEQUENCE: 519
gggtgccagc tctgccttga                                                  20

<210> SEQ ID NO 520
<211> LENGTH: 20
<212> TYPE: DNA
<213> ORGANISM: M. musculus

<400> SEQUENCE: 520
gaattttgtg aacaccagca                                                  20

<210> SEQ ID NO 521
<211> LENGTH: 20
<212> TYPE: DNA
<213> ORGANISM: M. musculus

<400> SEQUENCE: 521
tgtgcctctg tctataccga                                                  20

<210> SEQ ID NO 522
<211> LENGTH: 20
<212> TYPE: DNA
<213> ORGANISM: M. musculus

<400> SEQUENCE: 522
ctataccgag ctgctactgc                                                  20

<210> SEQ ID NO 523
<211> LENGTH: 20
<212> TYPE: DNA
<213> ORGANISM: M. musculus

<400> SEQUENCE: 523
ctactgcagg ggaatgactc                                                  20

<210> SEQ ID NO 524
<211> LENGTH: 20
<212> TYPE: DNA

```
<213> ORGANISM: M. musculus

<400> SEQUENCE: 524
tccagcgagt ggactcagag                                           20

<210> SEQ ID NO 525
<211> LENGTH: 20
<212> TYPE: DNA
<213> ORGANISM: M. musculus

<400> SEQUENCE: 525
tcagaggagt ctatcagaat                                           20

<210> SEQ ID NO 526
<211> LENGTH: 20
<212> TYPE: DNA
<213> ORGANISM: M. musculus

<400> SEQUENCE: 526
gaatgatctg gcaatcctag                                           20

<210> SEQ ID NO 527
<211> LENGTH: 20
<212> TYPE: DNA
<213> ORGANISM: M. musculus

<400> SEQUENCE: 527
gagcacaccc atctttcctt                                           20

<210> SEQ ID NO 528
<211> LENGTH: 20
<212> TYPE: DNA
<213> ORGANISM: M. musculus

<400> SEQUENCE: 528
aataaaagcc acatttaccc                                           20

<210> SEQ ID NO 529
<211> LENGTH: 20
<212> TYPE: DNA
<213> ORGANISM: M. musculus

<400> SEQUENCE: 529
aagccacatt taccctaggc                                           20

<210> SEQ ID NO 530
<211> LENGTH: 20
<212> TYPE: DNA
<213> ORGANISM: M. musculus

<400> SEQUENCE: 530
cctgtctgaa ctgttttcca                                           20

<210> SEQ ID NO 531
<211> LENGTH: 20
<212> TYPE: DNA
<213> ORGANISM: M. musculus

<400> SEQUENCE: 531
atggtgtgat ttccctgtac                                           20

<210> SEQ ID NO 532
<211> LENGTH: 20
```

```
<212> TYPE: DNA
<213> ORGANISM: M. musculus

<400> SEQUENCE: 532
tattatatgt taggtagact                                           20

<210> SEQ ID NO 533
<211> LENGTH: 20
<212> TYPE: DNA
<213> ORGANISM: M. musculus

<400> SEQUENCE: 533
tacattatca tatgtgcttg                                           20

<210> SEQ ID NO 534
<211> LENGTH: 20
<212> TYPE: DNA
<213> ORGANISM: M. musculus

<400> SEQUENCE: 534
atatgtgctt gttataccag                                           20

<210> SEQ ID NO 535
<211> LENGTH: 20
<212> TYPE: DNA
<213> ORGANISM: M. musculus

<400> SEQUENCE: 535
cactctgggt cagcagagca                                           20

<210> SEQ ID NO 536
<211> LENGTH: 20
<212> TYPE: DNA
<213> ORGANISM: M. musculus

<400> SEQUENCE: 536
ttactgtcaa tttacagctg                                           20

<210> SEQ ID NO 537
<211> LENGTH: 20
<212> TYPE: DNA
<213> ORGANISM: M. musculus

<400> SEQUENCE: 537
ctggctgaag ctagccctct                                           20

<210> SEQ ID NO 538
<211> LENGTH: 20
<212> TYPE: DNA
<213> ORGANISM: M. musculus

<400> SEQUENCE: 538
tagtagcagc aagtgttacc                                           20

<210> SEQ ID NO 539
<211> LENGTH: 20
<212> TYPE: DNA
<213> ORGANISM: M. musculus

<400> SEQUENCE: 539
gcagcaagtg ttacctttgt                                           20

<210> SEQ ID NO 540
```

```
<211> LENGTH: 20
<212> TYPE: DNA
<213> ORGANISM: M. musculus

<400> SEQUENCE: 540
ccagtgagat ggtcaccttt                                              20

<210> SEQ ID NO 541
<211> LENGTH: 20
<212> TYPE: DNA
<213> ORGANISM: M. musculus

<400> SEQUENCE: 541
gtagagcctt cggtccacat                                              20

<210> SEQ ID NO 542
<211> LENGTH: 20
<212> TYPE: DNA
<213> ORGANISM: M. musculus

<400> SEQUENCE: 542
atcatctctg tgtgtgctgc                                              20

<210> SEQ ID NO 543
<211> LENGTH: 20
<212> TYPE: DNA
<213> ORGANISM: M. musculus

<400> SEQUENCE: 543
taataggatt ttactgaggt                                              20

<210> SEQ ID NO 544
<211> LENGTH: 20
<212> TYPE: DNA
<213> ORGANISM: Artificial Sequence
<220> FEATURE:
<223> OTHER INFORMATION: Antisense Compound

<400> SEQUENCE: 544
ctgctagcct ctggatttga                                              20
```

MODULATION OF EIF4E-BP1 EXPRESSION

CROSS REFERENCE TO RELATED APPLICATIONS

This application claims priority to U.S. patent application Ser. No. 60/538,751, filed Jan. 22, 2004, the entire contents of which are herein incorporated by reference.

FIELD OF THE INVENTION

The present invention provides compositions and methods for modulating the expression of eIF4E-BP1. In particular, this invention relates to antisense compounds, particularly oligonucleotide compounds, which, in preferred embodiments, hybridize with nucleic acid molecules encoding eIF4E-BP1. Such compounds are shown herein to modulate the expression of eIF4E-BP1.

BACKGROUND OF THE INVENTION

Eukaryotic gene expression must be regulated such that cells can rapidly respond to a wide range of different conditions. The process of mRNA translation is one step at which gene expression is highly regulated. In response to hormones, growth factors, cytokines and nutrients, animal cells generally activate translation in preparation for the proliferative response. The rate of protein synthesis typically decreases under stressful conditions, such as oxidative or osmotic stress, DNA damage or nutrient withdrawal. Activation or suppression of mRNA translation occurs within minutes and control over this process is thought to be exerted at the initiation phase of protein synthesis (Rosenwald et al., *Oncogene*, 1999, 18, 2507-2517; Strudwick and Borden, *Differentiation*, 2002, 70, 10-22).

Translation initiation necessitates the coordinated activities of several eukaryotic initiation factors (eIFs), proteins which are classically defined by their cytoplasmic location and ability to regulate the initiation phase of protein synthesis. One of these factors, eukaryotic initiation factor 4E (eIF4E), is present in limiting amounts relative to other initiation factors and is one component of the eIF4F initiation complex, which is also comprised of the scaffold protein eIF4G and the RNA helicase eIF4A. In the cytoplasm, eIF4E catalyzes the rate-limiting step of cap-dependent protein synthesis by specifically binding to the 5' terminal 7-methyl GpppX cap structure present on nearly all mature cellular mRNAs, which serves to deliver the mRNAs to the eIF4F complex. Once bound, the eIF4F complex scans from the 5' to the 3' end of the cap, permitting the RNA helicase activity of eIF4A to resolve any secondary structure present in the 5' untranslated region (UTR), thus revealing the translation initiation codon and facilitating ribosome loading onto the mRNA (Graff and Zimmer, *Clin. Exp. Metastasis*, 2003, 20, 265-273; Strudwick and Borden, *Differentiation*, 2002, 70, 10-22).

eIF4E availability for incorporation into the eIF4E complex is regulated through phosphorylation as well as through the binding of inhibitory proteins. eIF4E is a phosphoprotein that is phosphorylated on serine 209 by the mitogen-activated protein kinase-interacting kinase Mnk1, as well as by protein kinase C (Flynn and Proud, *J. Biol. Chem.*, 1995, 270, 21684-21688; Wang et al., *J. Biol. Chem.*, 1998, 273, 9373-9377; Waskiewicz et al., *Embo J.*, 1997, 16, 1909-1920). The inhibitory eIF4E-binding proteins 1 and 2 (eIF4E-BP1 and eIF4E-BP2) act as effective inhibitors of translation by competing with eIF4G for binding to the dorsal surface of eIF4E (Ptushkina et al., *Embo J.*, 1999, 18, 4068-4075). When complexed with eIF4E-BP1, eIF4E is not a substrate for phosphorylation by protein kinase C or Mnk1, indicating that dissociation of eIF4E-BP1 from eIF4E is a prerequisite for eIF4E phosphorylation (Wang et al., *J. Biol. Chem.*, 1998, 273, 9373-9377; Whalen et al., *J Biol Chem*, 1996, 271, 11831-11837). Phosphorylation of eIF4E increases its affinity for mRNA caps, thus elevating translation rates (Waskiewicz et al., *Mol. Cell Biol.*, 1999, 19, 1871-1880).

Fifteen years prior to the cloning of its cDNA, the eIF4E-BP1 protein was identified as a protein phosphorylated in response to insulin and was proposed to be important in insulin action. In addition to insulin, insulin-like growth factor, platelet-derived growth factor, interleukin-2 and angiotensin II also promote the dissociation of eIF4E-BP1 from eIF4E (Lawrence and Abraham, *Trends Biochem Sci*, 1997, 22, 345-349). eIF4E-BP1 was independently cloned by two strategies, one using amino acid sequence information obtained following purification of the protein, and the other using eIF4E protein to probe a cDNA expression library (Hu et al., *Proc Natl Acad Sci USA*, 1994, 91, 3730-3734; Pause et al., *Nature*, 1994, 371, 762-767). eIF4E-BP1 is also known as phosphorylated heat- and acid-stable protein regulated by insulin (PHAS-I). eIF4E-BP1 is expressed in most human tissues, including heart, brain, placenta, lung, liver, kidney and spleen, and is most highly expressed in adipose tissue and skeletal muscle, the major insulin-responsive tissues (Hu et al., *Proc Natl Acad Sci USA*, 1994, 91, 3730-3734; Tsukiyama-Kohara et al., *Genomics*, 1996, 38, 353-363). The human gene maps to chromosome 8p12 (Tsukiyama-Kohara et al., *Genomics*, 1996, 38, 353-363). The mouse eIF4E-BP1 gene consists of three exons, spans approximately 16 kb and maps to mouse chromosome 8 (Tsukiyama-Kohara et al., *Genomics*, 1996, 38, 353-363).

Rather than preventing the binding of eIF4E to mRNA caps, eIF4E-BP1 prohibits the binding of eIF4E to eIF4G, thereby preventing formation of a complex that is necessary for efficient binding and proper positioning of the 40S ribosomal subunit on the target mRNA. The region to which eIF4E binds is a common motif shared by eIF4G and eIF4E-BP1, and point mutations in this region of eIF4E-BP1 abolish binding to eIF4E (Mader et al., *Mol Cell Biol*, 1995, 15, 4990-4997). eIF4E-BP1 exists in a 1:1 ratio with eIF4E, and eIF4E-BP1 and eIF4G bind to eIF4E in a mutually exclusive manner (Rau et al., *J Biol Chem*, 1996, 271, 8983-8990).

Phosphorylation of bp 1 results in the release of eIF4E, allowing the formation of the eIF4F complex and eIF4F-dependent translation (Lin et al., *Science*, 1994, 266, 653-656; Pause et al., *Nature*, 1994, 371, 762-767). Two motifs are required for the efficient phosphorylation of eIF4E-BP1; the RAIP motif, which is found in the NH2-terminal region of EIF4E-BP1 and the TOS motif, which is formed by the last five amino acids of eIF4E-BP1 (Schalm and Blenis, *Curr Biol*, 2002, 12, 632-639; Tee and Proud, *Mol Cell Biol*, 2002, 22, 1674-1683). Mitogen-activated protein kinase, the major insulin-stimulated kinase in rat adipocytes, can phosphorylate recombinant eIF4E-BP1 in vitro (Lin et al., *Science*, 1994, 266, 653-656). However, MAP kinase did not readily phosphorylate eIF4E-BP1 when complexed with eIF4E. Moreover, the immunosuppressant rapamycin, which blocks activation of the kinase p70s6K by insulin without affecting the activation of MAP kinase, attenuated the stimulation of eIF4E-BP1 phosphorylation by insulin and significantly inhibited the dissociation of eIF4E-BP1 from eIF4E, without affecting MAP kinase activity. Furthermore, a MAP kinase kinase inhibitor markedly decreased insulin-stimulated MAP kinase activity without affecting eIF4E-BP1 phosphorylation or association with eIF4E (Lin et al., *J Biol Chem*, 1995, 270, 18531-18538). The inhibitory target of rapamycin, FRAP/mRAFT/mTOR, is an upstream element of the p70 signaling pathway, thus inhibition of eIF4E-BP1 phosphorylation by rapamycin is mediated by the mTOR signaling pathway, independently of MAP kinase (von Manteuffel et al., *Proc Natl Acad Sci USA*, 1996, 93, 4076-4080). The phosphorylation of eIF4E-BP1 by mTOR on threonine-36 and threonine-45 in vitro prevented the binding of eIF4E-BP1 to eIF4E (Brunn et al., *Science*, 1997, 277, 99-101; Burnett et al., *Proc Natl Acad Sci USA*, 1998, 95, 1432-1437). mTOR activity is required for the phosphorylation of eIF4E-BP1 in insulin-stimulated human embryonic kidney cells, and threonine-45 appears to be the major regulator of the in vivo interaction between eIF4E-BP1 and eIF4E (Brunn et al., *Science*, 1997, 277, 99-101; Burnett et al., *Proc Natl Acad Sci USA*, 1998, 95, 1432-1437).

Intracellular nutrients, as well as extracellular growth factors, also utilize eIF4E-BP1 as an effector of a signaling network. With respect to the availability of nutrients, the responsiveness of eIF4E-BP1 to insulin requires only the presence of amino acids, unlike other translational regulators which also require glucose (Campbell et al., *Biochem J*, 1999, 344 Pt 2, 433-441). The addition of leucine to isolated rat adipocytes significantly stimulated eIF4E-BP1 phosphorylation and leptin secretion in a rapamycin-sensitive and actinomycin D-resistant manner, indicating that leucine activates translation of leptin mRNA through the mTOR/bp pathway (Roh et al., *Am J Physiol Endocrinol Metab*, 2003, 284, E322-330). Leptin is produced mainly by adipose cells and regulates food intake and whole body energy balance, and because insulin levels respond to the nutritional status of the body, insulin has been suggested as a potential mediator between food intake and leptin production. The finding that leucine stimulates mTOR/eIF4E-BP1-mediated leptin production provides a possible connection between nutrient intake and circulating leptin levels (Roh et al., *Am J Physiol Endocrinol Metab*, 2003, 284, E322-330). An additional example of a link between nutritional status and translation is seen in skeletal muscle, a tissue where eIF4E-BP1 is abundantly expressed. In muscle from fasted rats, the amount of eIF4E associated with eIF4E-BP1 (and thus inhibited) is increased 5-fold as compared to muscle from freely fed animals. One hour following refeeding of a nutritionally complete diet, eIF4E-BP1 phosphorylation is increased, and the amount of eIF4E-BP1 bound to eIF4E is lowered to freely fed control values (Yoshizawa et al., *Biochem Biophys Res Commun*, 1997, 240, 825-831).

Systemic disruption of mouse eIF4E-BP1 does not lead to any abnormalities in the development or reproductive behavior of female mice, but does cause a 10% reduction in the body weight of male mice. The expression of eIF4E-BP1 and eIF4E in these mice does not appear to be altered (Blackshear et al., *J Biol Chem*, 1997, 272, 31510-31514). Surprisingly, a subsequent systemic gene disruption in a different mouse strain demonstrated that the interaction between bp1 and eIF4E impacts body weight, and fat and glucose metabolism. The bp1-deficient mice display reductions in fat tissue growth and weight gain, and also exhibit decrease circulating leptin levels. Furthermore, the eIF4E-BP1-deficient mice are hypoglycemic, suggesting that eIF4E-BP1 gene disruption can modulate insulin signaling. The mice bearing the eIF4E-BP1 disruption have a higher metabolic rate, which could be associated with the replacement of white fat tissue with brown fat tissue, which contains an uncoupling protein that generates heat by circumventing the mitochondrial proton battery. These results demonstrate that cap-dependent translation, in which eIF4E-BP1 functions as an important modulator, significantly regulates energy homeostasis and glucose and fat metabolism (Tsukiyama-Kohara et al., 2001, *Nature Med*. 7, 1128-1132; Sonenberg et al., 2003).

In some instances, the association of eIF4E-BP1 with eIF4E is stimulated. Agents that raise cyclicAMP levels increase the amount of eIF4E bound to eIF4E-BP1 and attenuate the effects of insulin on eIF4E-BP1 (Lin and Lawrence, *J Biol Chem*, 1996, 271, 30199-30204). Certain viruses, such as encephalomyocarditis virus and polio virus, promote the association of eIF4E-BP1 with eIF4E, thereby inhibiting translation of the capped mRNA of the host cell while allowing viral protein synthesis (Gingras et al., *Proc Natl Acad Sci USA*, 1996, 93, 5578-5583).

Induction of cellular differentiation and reduction of cellular proliferation are concomitant with a reduction in translation rates, as is observed during human myeloid cell differentiation. When induced to differentiate into monocytes/macrophages, cells from the HL-60 promyelocytic leukemia cell or U-937 monoblastic cell lines exhibit a decrease in the phosphorylation of eIF4E-BP1. In contrast, when HL-60 cells are stimulated to differentiate into granulocytic cells, the amount of eIF4E-BP1 is decreased, whereas phosphorylation of eIF4E-BP1 is not affected. Conversely, bp2 levels are markedly increased. These findings suggest that translation machinery is differentially regulated during human myeloid cell differentiation (Grolleau et al., *Leukemia*, 2000, 14, 1909-1914).

The disregulation of signaling networks that promote cell proliferation is often observed in association with cancer (Lawrence and Abraham, *Trends Biochem Sci*, 1997, 22, 345-349). Expression of excess eIF4E-BP1 in cells transformed by eIF4E or v-src results in significant reversion of the transformed phenotype, demonstrating that eIF4E-BP1 can function as an inhibitor of cell growth (Rousseau et al., *Oncogene*, 1996, 13, 2415-2420). US Patent Application Publication US 2003/0144190 A1 (Sonenberg et al) describes methods of immortalizing an oncogene-induced transformed cell which comprise increasing the amount of eIF4F pre-initiation complex by desequestration and/or inhibition of the sequestration of eIF4E in a complex with an eIF4E sequestering agent that comprises an antisense RNA complementary to the nucleotide sequence encoding for 4E-BP1.

Given the link between eIF4E-BP1-regulated translation initiation and food intake, and the importance of bp1 in regulating energy homeostasis, glucose metabolism and fat metabolism, it is of value to identify specific inhibitors of eIF4E-BP1. Currently, there are no known therapeutic agents that target eIF4E-BP1. Consequently, there remains a long felt need for agents capable of effectively inhibiting eIF4E-BP1. Antisense technology is an effective means of reducing the expression of specific gene products and therefore is uniquely useful in a number of therapeutic, diagnostic and research applications for the modulation of eIF4E-BP1 expression.

The U.S. Pat. No. 6,410,715 describes a purified human nucleic acid sequence encoding a cellular component that binds to eIF4E comprising a coding sequence for the protein eIF4E-BP1, and discloses a method for screening a non-hormone agent potentially useful to treat a hormone disorder (Sonenberg et al., 2000).

The US pre-grant publication 2003/0041341 (Sonenberg et al., 2003) discloses a method of decreasing fat tissue growth and/or weight gain, comprising administering an agent which desequesters eIF4E from a sequestering agent, wherein said sequestration of eIF4E is through its interaction with eIF4E-BP1, and wherein said desequestration or inhibition of sequestration is effected by an inhibition of the synthesis of eIF4E-BP1, comprising an agent which inhibits the synthesis of eIF4E-BP1, wherein said agent comprises an antisense RNA complementary to the nucleotide sequence encoding for eIF4E-BP1. Described therein are also methods of treating obesity and diabetes, comprising administering an agent which increases the amount of eIF4E available for a formation of eIF4F preinitiation complex, wherein said agent is an agent which desequesters eIF4E from eIF4E-BP1. Disclosed in this application is an antisense oligonucleotide primer targeting mouse eIF4E-BP1, and generally disclosed are oligonucleotide primers at least 12 nucleotides in length, preferably between 15 and 24 nucleotides.

The present invention provides compositions and methods for inhibiting eIF4E-BP1 expression.

SUMMARY OF THE INVENTION

The present invention is directed to antisense compounds, especially nucleic acid and nucleic acid-like oligomers, which are targeted to a nucleic acid encoding eIF4E-BP1, and which modulate the expression of eIF4E-BP1. Pharmaceutical and other compositions comprising the compounds of the invention are also provided. Further provided are methods of screening for modulators of eIF4E-BP1 and methods of modulating the expression of eIF4E-BP1 in cells, tissues or animals comprising contacting said cells, tissues or animals with one or more of the compounds or compositions of the invention. Methods of treating an animal, particularly a human, suspected of having or being prone to a disease or condition associated with expression of eIF4E-BP1, thereby in some instances delaying onset of said disease or condition, are also set forth herein. Such human patient populations include, but are not limited to, humans having diabetes or other metabolic disorders. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs antisense compounds, preferably oligonucleotides and similar species for use in modulating the function or effect of nucleic acid molecules encoding eIF4E-BP1. This is accomplished by providing oligonucleotides which specifically hybridize with one or more nucleic acid molecules encoding eIF4E-BP1. As used herein, the terms "target nucleic acid" and "nucleic acid molecule encoding eIF4E-BP1" have been used for convenience to encompass DNA encoding eIF4E-BP1, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of eIF4E-BP1. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison, Wis.), using default settings, which uses the algorithm of Smith and Waterman (Adv. Appl. Math., 1981, 2, 482-489). In some preferred embodiments, homology, sequence identity or complementarity, between the oligomeric and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%.

B. Compounds of the Invention

According to the present invention, antisense compounds include antisense oligomeric compounds, antisense oligonucleotides, siRNAs, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell,* 1995, 81, 611-620).

Montgomery et al. have shown that the primary interference effects of dsRNA are posttranscriptional (Montgomery et al., *Proc. Natl. Acad. Sci. USA,* 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature,* 1998, 391, 806-811). Recently, it has been shown that it is, in fact, the single-stranded RNA oligomers of antisense polarity of the dsRNAs which are the potent inducers of RNAi (Tijsterman et al., *Science,* 2002, 295, 694-697).

The antisense compounds of the present invention also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound. These compounds are then tested using the methods described herein to determine their ability to inhibit expression of eIF4E-BP1 mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the antisense compounds of this invention, the present invention comprehends other families of antisense compounds as well, including but not limited to oligonucleotide analogs and mimetics such as those described herein.

The antisense compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the antisense compounds of the invention are 13 to 50 nucleobases in length. One having ordinary skill in the art will appreciate that this embodies compounds of 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the antisense compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 13 to about 50 nucleobases, even more preferably those comprising from about 15 to about 30 nucleobases.

While oligonucleotides are one form of antisense compound, the present invention comprehends other oligomeric antisense compounds, including but not limited to oligonucleotide mimetics such as are described below. The compounds in accordance with this invention can comprise from about 8 to about 80 nucleobases. In another embodiment, the oligonucleotide is about 10 to 50 nucleotides in length. In yet another embodiment, the oligonucleotide is 12 to 30 nucleotides in length. In yet another embodiment, the oligonucleotide is 12 to 24 nucleotides in length. In yet another embodiment, the oligonucleotide is 19 to 23 nucleotides in length. Some embodiments comprise at least an 8-nucleobase portion of a sequence of an oligomeric compound which inhibits expression of eIF4E-BP1. dsRNA or siRNA molecules directed to eIF4E-BP1, and their use in inhibiting eIF4E-BP1 mRNA expression, are also embodiments within the scope of the present invention.

The oligonucleotides of the present invention also include variants in which a different base is present at one or more of the nucleotide positions in the oligonucleotide. For example, if the first nucleotide is an adenosine, variants may be produced which contain thymidine (or uridine if RNA), guanosine or cytidine at this position. This may be done at any of the positions of the oligonucleotide. These oligonucleotides are then tested using the methods described herein to determine their ability to inhibit expression of eIF4E-BP1 mRNA.

Antisense compounds 13-80 nucleobases in length comprising a stretch of at least thirteen (13) consecutive nucleobases selected from within the illustrative antisense compounds are considered to be suitable antisense compounds as well.

Exemplary preferred antisense compounds include oligonucleotide sequences that comprise at least the 13 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 13 to about 80 nucleobases). Similarly preferred antisense compounds are represented by oligonucleotide sequences that comprise at least the 13 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 13 to about 80 nucleobases). It is also understood that preferred antisense compounds may be represented by oligonucleotide sequences that comprise at least 13 consecutive nucleobases from an internal portion of the sequence of an illustrative preferred antisense compound, and may extend in either or both directions until the oligonucleotide contains about 13 to about 80 nucleobases.

One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes eIF4E-BP1.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding eIF4E-BP1, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). It is also understood that preferred antisense target segments may be represented by DNA or RNA sequences that comprise at least 8 consecutive nucleobases from an internal portion of the sequence of an illustrative preferred target segment, and may extend in either or both directions until the oligonucleotide contains about 8 to about 80 nucleobases. One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric antisense compounds may also be targeted to regions of the target nucleobase sequence comprising nucleobases 1-80, 81-160, 161-240, 241-320, 321-400, 401-480, 481-560, 561-640, 641-720, 721-800, 801-880, 881-895, or any combination thereof.

In one embodiment, the antisense compounds are targeted to a nucleic acid molecule encoding human eIF4E-BP1, for example, to nucleotides 43-62 in the 5' UTR, nucleotides 45-79 in the start codon region, nucleotides 68-198, 223-330, 336-413 in the coding region, nucleotides 411-430 in the stop codon region or nucleotides 423-786 in the 3' UTR, all of SEQ ID NO: 4; nucleotides 19263-19282 or 25252-25271 or nucleotides 29235-29254 of SEQ ID NO: 26.

In another embodiment, the antisense compounds are targeted to a nucleic acid molecule encoding mouse eIF4E-BP1, for example, to nucleotides 11-20 in the start codon region, nucleotides 151-335 in the coding region, nucleotides 352-371 in the stop codon region, or nucleotides 367-749 in the 3' UTR, all of SEQ ID NO: 11; nucleotides 43-62 in the start codon region or nucleotides 351-341 in the coding region, both of SEQ ID NO: 25.

In a further embodiment, the antisense compound is targeted to a nucleic acid molecule encoding rat eIF4E-BP1, for example to nucleotides 37-72 in the start codon region, nucleotides 63-365 or 368-387 in the coding region; nucleotides 389-413 in the stop codon region and nucleotides 411-524, 536-831 in the 3' UTR, all of SEQ ID NO: 18; or nucleotides 579-598 in the stop codon region of SEQ ID NO: 428, wherein said compound inhibits the expression of rat eIF4E-BP1 mRNA.

D. Screening and Target Validation

In a further embodiment, the "preferred target segments" identified herein may be employed in a screen for additional compounds that modulate the expression of eIF4E-BP1. "Modulators" are those compounds that decrease or increase the expression of a nucleic acid molecule encoding eIF4E-BP1 and which comprise at least an 8-nucleobase portion which is complementary to a preferred target segment. The screening method comprises the steps of contacting a preferred target segment of a nucleic acid molecule encoding eIF4E-BP1 with one or more candidate modulators, and selecting for one or more candidate modulators which decrease or increase the expression of a nucleic acid molecule encoding eIF4E-BP1. Once it is shown that the candidate modulator or modulators are capable of modulating (e.g. either decreasing or increasing) the expression of a nucleic acid molecule encoding eIF4E-BP1, the modulator may then be employed in further investigative studies of the function of eIF4E-BP1, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processsing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The antisense compounds of the present invention can also be applied in the areas of drug discovery and target validation. The present invention comprehends the use of the compounds and preferred target segments identified herein in drug discovery efforts to elucidate relationships that exist between eIF4E-BP1 and a disease state, phenotype, or condition. These methods include detecting or modulating eIF4E-BP1 comprising contacting a sample, tissue, cell, or organism with the compounds of the present invention, measuring the nucleic acid or protein level of eIF4E-BP1 and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The antisense compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al, *Drug Discov. Today* 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The antisense compounds of the invention are useful for research and diagnostics, because these compounds hybridize to nucleic acids encoding eIF4E-BP1. For example, oligonucleotides that are shown to hybridize with such efficiency and under such conditions as disclosed herein as to be effective eIF4E-BP1 inhibitors will also be effective primers or probes under conditions favoring gene amplification or detection, respectively. These primers and probes are useful in methods requiring the specific detection of nucleic acid molecules encoding eIF4E-BP1 and in the amplification of said nucleic acid molecules for detection or for use in further studies of eIF4E-BP1. Hybridization of the antisense oligonucleotides, particularly the primers and probes, of the invention with a nucleic acid encoding eIF4E-BP1 can be detected by means known in the art. Such means may include conjugation of an enzyme to the oligonucleotide, radiolabelling of the oligonucleotide or any other suitable detection means. Kits using such detection means for detecting the level of eIF4E-BP1 in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of eIF4E-BP1 is treated by administering antisense compounds in accordance with this invention. For example, in one non-limiting embodiment, the methods comprise the step of administering to the animal in need of treatment, a therapeutically effective amount of a eIF4E-BP1 inhibitor. The eIF4E-BP1 inhibitors of the present invention effectively inhibit the activity of the eIF4E-BP1 protein or inhibit the expression of the eIF4E-BP1 protein. In one embodiment, the activity or expression of eIF4E-BP1 in an animal is inhibited by about 10%. Preferably, the activity or expression of eIF4E-BP1 in an animal is inhibited by about 30%. More preferably, the activity or expression of eIF4E-BP1 in an animal is inhibited by 50% or more. Thus, the oligomeric antisense compounds modulate expression of eIF4E-BP1 mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of eIF4E-BP1 may be measured in serum, adipose tissue, liver or any other body fluid, tissue or organ of the animal. Preferably, the cells contained within said fluids, tissues or organs being analyzed contain a nucleic acid molecule encoding eIF4E-BP1 protein and/or the eIF4E-BP1 protein itself.

The antisense compounds of the invention can be utilized in pharmaceutical compositions by adding an effective amount of a compound to a suitable pharmaceutically acceptable diluent or carrier. Use of the compounds and methods of the invention may also be useful prophylactically.

The compounds of the present inventions are inhibitors of eIF4E-BP1 expression. Thus, the compounds of the present invention are believed to be useful for treating metabolic diseases and conditions, particularly diabetes, obesity, hyperlipidemia or metabolic syndrome X. The compounds of the invention are also believed to be useful for preventing or delaying the onset of metabolic diseases and conditions, particularly diabetes, obesity, hyperlipidemia or metabolic syndrome X. Metabolic syndrome, metabolic syndrome X or simply Syndrome X refers to a cluster of risk factors that include obesity, dyslipidemia, particularly high blood triglycerides, glucose intolerance, high blood sugar and high blood pressure. Scott, C. L., Am J Cardiol. Jul. 3, 2003; 92(1A):35i-42i. The compounds of the invention have surprisingly been found to be effective for lowering blood glucose, including plasma glucose, and for lowering blood lipids, including serum lipids, particularly serum cholesterol and serum triglycerides. The compounds of the invention are therefore particularly useful for the treatment, prevention and delay of onset of type 2 diabetes, high blood glucose and hyperlipidemia.

F. Modifications

As is known in the art, a nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound; however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriaminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863;

4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred antisense compounds, e.g., oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified antisense compounds may also contain one or more substituted sugar moieties. Preferred are antisense compounds, preferably antisense oligonucleotides, comprising one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Antisense compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. No. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750, 692, which is commonly owned with the instant application and also herein incorporated by reference.

Conjugates

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. Chimeric antisense oligonucleotides are thus a form of antisense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety. For oligonucleotides, presently preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. Sodium salts are presently believed to be more preferred.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosourea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same. Each of the references, GenBank® accession numbers, and the like recited in the present application is incorporated herein by reference in its entirety.

EXAMPLES

Example 1

Design and Screening of Duplexed Antisense Compounds Targeting eIF4E-BP1

In accordance with the present invention, a series of nucleic acid duplexes comprising the antisense compounds of the present invention and their complements can be designed to target eIF4E-BP1. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. Overhangs can range from 2 to 6 nucleobases and these nucleobases may or may not be complementary to the target nucleic acid. In another embodiment, the duplexes may have an overhang on only one terminus.

For example, a duplex comprising an antisense strand having the sequence CGAGAGGCGGACGGGACCG and having a two-nucleobase overhang of deoxythymidine (dT) would have the following structure:

  Antisense Strand

Complement

In another embodiment, a duplex comprising an antisense strand having the same sequence CGAGAGGCGGACGG-GACCG may be prepared with blunt ends (no single stranded overhang) as shown:

  Antisense Strand

Complement

The RNA duplex can be unimolecular or bimolecular; i.e., the two strands can be part of a single molecule or may be separate molecules.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate eIF4E-BP1 expression.

When cells reached 80% confluency, they are treated with duplexed antisense compounds of the invention. For cells grown in 96-well plates, wells are washed once with 200 μL OPTI-MEM™-1 reduced-serum medium (Invitrogen Life Technologies, Carlsbad, Calif.) and then treated with 130 μL of OPTI-MEM™-1 containing 12 μg/mL LIPOFECTIN™ (Invitrogen Life Technologies, Carlsbad, Calif.) per 200 nM of the desired duplex antisense compound. After 5 hours of treatment, the medium is replaced with fresh medium. Cells are harvested 16 hours after treatment, at which time RNA is isolated and target reduction measured by real-time PCR.

Example 2

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 3

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 4

Oligonucleotide Analysis

96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 5

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or real-time PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Life Technologies, Carlsbad, Calif.) supplemented with 10% fetal bovine serum (Invitrogen Life Technologies, Carlsbad, Calif.), penicillin 100 units per mL, and streptomycin 100 micrograms per mL (Invitrogen Life Technologies, Carlsbad, Calif.). Cells were routinely passaged by trypsinization and dilution when they reached 90% confluence. Cells were seeded into 96-well plates (e.g., Falcon-Primaria #3872, BD Biosciences, Bedford, Mass.) at a density of approximately 7000 cells/well for use in oligonucleotide transfection experiments and real-time PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Life Technologies, Carlsbad, Calif.) supplemented with 10% fetal bovine serum (Invitrogen Life Technologies, Carlsbad, Calif.), penicillin 100 units per mL, and streptomycin 100 micrograms per mL (Invitrogen Life Technologies, Carlsbad, Calif.). Cells were routinely passaged by trypsinization and dilution when they reached 90% confluence. Cells were seeded onto 96-well plates (e.g., Falcon-Primaria #353872, BD Biosciences, Bedford, Mass.) at a density of approximately 5000 cells per well for use in oligonucleotide transfection experiments and real-time PCR analysis.

NHDF Cells:

Human neonatal dermal fibroblast (NF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

b.END Cells:

The mouse brain endothelial cell line b.END was obtained from Dr. Werner Risau at the Max Plank Instititute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached 90% confluence. Cells were seeded into 96-well plates (e.g., Falcon-Primaria #353872, BD Biosciences, Bedford, Mass.) at a density of approximately 3000 cells/well for use in oligonucleotide transfection experiments and real-time PCR analysis.

For Northern blotting or other analyses, cells may be seeded onto 100 mm or other standard tissue culture plates and treated similarly, using appropriate volumes of medium and oligonucleotide.

A10 Cells:

The rat aortic smooth muscle cell line A10 was obtained from the American Type Culture Collection (Manassas, Va.). A10 cells were routinely cultured in DMEM, high glucose (American Type Culture Collection, Manassas, Va.) supplemented with 10% fetal bovine serum (Invitrogen Life Technologies, Carlsbad, Calif.). Cells were routinely passaged by trypsinization and dilution when they reached 80% confluence. Cells were seeded into 96-well plates (e.g., Falcon-Primaria #353872, BD Biosciences, Bedford, Mass.) at a density of approximately 2500 cells/well for use oligonucleotide transfection experiments and real-time PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 65-75% confluency, they were treated with oligonucleotide. Oligonucleotide was mixed with LIPO-FECTIN™ (Invitrogen Life Technologies, Carlsbad, Calif.) in OPTI-MEM™-1 reduced-serum medium (Invitrogen Life Technologies, Carlsbad, Calif.) to achieve the desired concentration of oligonucleotide and a concentration of 2.5 to 3 ug/mL LIPOFECTIN™ per 100 nM oligonucleotide. For cells grown in 96-well plates, wells were washed once with 100 μL OPTI-MEM™-1 reduced-serum medium and then treated with 130 μL of the LIPOFECTIN™/oligonucleotide mixture. Cells are treated and data are obtained in duplicate or triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 6

Analysis of Oligonucleotide Inhibition of eIF4E-BP1 Expression

Antisense modulation of eIF4E-BP1 expression can be assayed in a variety of ways known in the art. For example, eIF4E-BP1 mRNA levels can be quantitated by, e.g., Northern blot analysis, competitive polymerase chain reaction (PCR), or real-time PCR. Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of eIF4E-BP1 can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to eIF4E-BP1 can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 7

Design of Phenotypic Assays for the Use of eIF4E-BP1 Inhibitors

Once eIF4E-BP1 inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of eIF4E-BP1 in health and disease. Representative phenotypic assays, which can be purchased from any one of several commercial vendors, include those for determining cell viability, cytotoxicity, proliferation or cell survivals (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with eIF4E-BP1 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the eIF4E-BP1 inhibitors. Hallmark genes, or those genes suspected to be associated with a specific disease state, condition, or phenotype, are measured in both treated and untreated cells.

Example 8

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine, Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIA-VAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia, Calif.). Essentially, after lysing of the cells on the culture plate, the plate is transferred to the robot deck where the pipetting, DNase treatment and elution steps are carried out.

Example 9

Real-Time Quantitative PCR Analysis of eIF4E-BP1 mRNA Levels

Quantitation of eIF4E-BP1 mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

Isolated RNA is subjected to a reverse transcriptase (RT) reaction, for the purpose of generating complementary DNA (cDNA), which is the substrate for the real-time PCR. Reverse transcriptase and real-time PCR reagents were obtained from Invitrogen Life Technologies, (Carlsbad, Calif.). The RT reaction and real-time PCR were carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time PCR are normalized using either the expression level of GAPDH, a gene whose expression is constant, or by quantifying total RNA using RiboGreen™ (Molecular Probes, Inc. Eugene, Oreg.). GAPDH expression is quantified by real time real-time PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and primers to human eIF4E-BP1 were designed to hybridize to a human eIF4E-BP1 sequence, using published sequence information (GenBank® accession number NM_004095.2, incorporated herein as SEQ ID NO: 4). For human eIF4E-BP1 the PCR primers were: forward primer: CCAGCCCTTCCAGTGATGAG (SEQ ID NO: 5) reverse primer: ATCTTCTGGGCTATTGCGCA (SEQ ID NO: 6) and the PCR probe was: FAM-CCCATGGAAGCCAGCCA-GAGCC-TAMRA (SEQ ID NO: 7) where FAM is the fluorescent dye and TAMRA is the quencher dye. For human GAPDH the PCR primers were:
forward primer: GAAGGTGAAGGTCGGAGTC (SEQ ID NO: 8)
reverse primer: GAAGATGGTGATGGGATTTC (SEQ ID NO: 9) and the PCR probe was: 5' JOE-CAAGCTTC-CCGTTCTCAGCC-TAMRA 3' (SEQ ID NO: 10) where JOE is the fluorescent reporter dye and TAMRA is the quencher dye.

Probes and primers to mouse eIF4E-BP1 were designed to hybridize to a mouse eIF4E-BP1 sequence, using published sequence information (GenBank® accession number NM_007918.2, incorporated herein as SEQ ID NO: 11). For mouse eIF4E-BP1 the PCR primers were:

forward primer: CCAGCAGCCCGGAAGATAA (SEQ ID NO: 12)
reverse primer: GGTCCCTTAAATGTCCATCTCAA (SEQ ID NO: 13) and the PCR probe was: FAM-CGGGCAG-GCGGTGAAGAGTCA-TAMRA (SEQ ID NO: 14) where FAM is the fluorescent reporter dye and TAMRA is the quencher dye. For mouse GAPDH the PCR primers were:
forward primer: GGCAAATTCAACGGCACAGT (SEQ ID NO: 15)
reverse primer: GGGTCTCGCTCCTGGAAGAT (SEQ ID NO: 16) and the PCR probe was: 5' JOE-AAGGC-CGAGAATGGGAAGCTTGTCATC-TAMRA 3' (SEQ ID NO: 17) where JOE is the fluorescent reporter dye and TAMRA is the quencher dye.

Probes and primers to rat eIF4E-BP1 were designed to hybridize to a rat eIF4E-BP1 sequence, using published sequence information (GenBank® accession number NM_053857.1, incorporated herein as SEQ ID NO: 18). For rat eIF4E-BP1 the PCR primers were:
forward primer: CCTACACCCTCCCTGCATCA (SEQ ID NO: 19)
reverse primer: TGCCAGATCATTCCGACAGA (SEQ ID NO: 20) and the PCR probe was: FAM-CGCCAGC-GAGTGGACACAGAGG-TAMRA (SEQ ID NO: 21) where FAM is the fluorescent reporter dye and TAMRA is the quencher dye. For rat GAPDH the PCR primers were:
forward primer: TGTTCTAGAGACAGCCGCATCTT (SEQ ID NO: 22)
reverse primer: CACCGACCTTCACCATCTTGT (SEQ ID NO: 23) and the PCR probe was: 5' JOE-TTGTGCAGT-GCCAGCCTCGTCTCA-TAMRA 3' (SEQ ID NO: 24) where JOE is the fluorescent reporter dye and TAMRA is the quencher dye.

Example 10

Northern Blot Analysis of eIF4E-BP1 mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AM-RESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human eIF4E-BP1, a human eIF4E-BP1 specific probe was prepared by PCR using the forward primer CCAGCCCTTCCAGTGATGAG (SEQ ID NO: 5) and the reverse primer ATCTTCTGGGCTATTGCGCA (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse eIF4E-BP1, a mouse eIF4E-BP1 specific probe was prepared by PCR using the forward primer CCAG- CAGCCCGGAAGATAA (SEQ ID NO: 12) and the reverse primer GGTCCCTTAAATGTCCATCTCAA (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

To detect rat eIF4E-BP1, a rat eIF4E-BP1 specific probe was prepared by PCR using the forward primer CCTACAC-CCTCCCTGCATCA (SEQ ID NO: 19) and the reverse primer TGCCAGATCATTCCGACAGA (SEQ ID NO: 20). To normalize for variations in loading and transfer efficiency membranes were stripped and probed for rat glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 11

Antisense Inhibition of Human eIF4E-BP1 Expression by Chimeric Phosphorothioate Oligonucleotides Having 2'-MOE Wings and a Deoxy Gap In accordance with the present invention, a series of antisense compounds was designed to target different regions of the human eIF4E-BP1 RNA, using published sequences (GenBank® accession number NM_004095.2, incorporated herein as SEQ ID NO: 4 and the complement of nucleotides 78114 to 108765 of the sequence with GenBank® accession number NT_078038.1, incorporated herein as SEQ ID NO: 26). The compounds are shown in Tables 1 and 2. "Target site" indicates the first (5'-most) nucleotide number on the particular target sequence to which the compound binds. All compounds in Tables 1 and 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytosine residues are 5-methylcytosines.

The compounds in Table 1 were analyzed for their effect on human eIF4E-BP1 mRNA levels by quantitative real-time PCR as described in other examples herein. Data, shown in Table 1, are averages from two experiments in which T-24 cells were treated with 100 nM of the antisense oligonucleotides of the present invention. SEQ ID NO: 2 was used as the control oligonucleotide in this assay. If present, "N.D." indicates "no data".

TABLE 1

Inhibition of human eIF4E-BP1 mRNA levels in T-24 cells by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 178716 | Coding | 4 | 338 | aggtggctctggctggcttc | 34 | 27 |
| 178719 | Coding | 4 | 309 | ctcatcactggaagggctgg | 65 | 28 |
| 178721 | Coding | 4 | 237 | gttccgacactccatcagga | 73 | 29 |
| 178723 | Coding | 4 | 293 | ctggtgacccccggaatggt | 54 | 30 |
| 178726 | Coding | 4 | 350 | gggctattgcgcaggtggct | 30 | 31 |
| 178728 | Coding | 4 | 345 | attgcgcaggtggctctggc | 72 | 32 |
| 178730 | Coding | 4 | 308 | tcatcactggaagggctggt | 0 | 33 |
| 178733 | Coding | 4 | 156 | ggtcgtgctgtagtcccgg | 27 | 34 |
| 178735 | Coding | 4 | 355 | cttctgggctattgcgcagg | 0 | 35 |
| 178738 | Coding | 4 | 363 | ccgcttatcttctgggctat | 1 | 36 |
| 178740 | Coding | 4 | 69 | gctgcagctgctgccccgg | 28 | 37 |
| 178742 | Coding | 4 | 396 | gtccatctcaaactgtgact | 71 | 38 |
| 178745 | Coding | 4 | 365 | gcccgcttatcttctgggct | 23 | 39 |
| 178747 | Coding | 4 | 70 | ggctgcagctgctgccccg | 21 | 40 |
| 178749 | Coding | 4 | 367 | ccgcccgcttatcttctggg | 0 | 41 |
| 178752 | Coding | 4 | 253 | ttttggtcacaggtgagttc | 0 | 42 |
| 178754 | Coding | 4 | 289 | tgaccccggaatggtgggc | 0 | 43 |
| 178756 | Coding | 4 | 223 | tcaggaatttccggtcatag | 57 | 44 |
| 178759 | Coding | 4 | 288 | gaccccggaatggtgggca | 32 | 45 |
| 178761 | Coding | 4 | 354 | ttctgggctattgcgcaggt | 0 | 46 |
| 178763 | Coding | 4 | 76 | gggtctggctgcagctgctg | 54 | 47 |
| 178766 | Coding | 4 | 301 | tggaagggctggtgacccc | 35 | 48 |
| 178768 | Coding | 4 | 226 | ccatcaggaatttccggtca | 54 | 49 |
| 178771 | Coding | 4 | 232 | gacactccatcaggaatttc | 11 | 50 |
| 178773 | Coding | 4 | 234 | ccgacactccatcaggaatt | 6 | 51 |
| 178775 | Coding | 4 | 240 | tgagttccgacactccatca | 31 | 52 |
| 178777 | Coding | 4 | 242 | ggtgagttccgacactccat | 0 | 53 |
| 178780 | Start Codon | 4 | 65 | cagctgctgccccggacat | 26 | 54 |
| 178782 | Coding | 4 | 71 | tggctgcagctgctgccccc | 5 | 55 |
| 178784 | Coding | 4 | 311 | ggctcatcactggaagggct | 39 | 56 |
| 178787 | Coding | 4 | 282 | cggaatggtgggcagatccc | 12 | 57 |
| 178789 | Coding | 4 | 366 | cgcccgcttatcttctgggc | 0 | 58 |
| 178791 | Coding | 4 | 341 | cgcaggtggctctggctggc | 80 | 59 |
| 178794 | Coding | 4 | 395 | tccatctcaaactgtgactc | 1 | 60 |
| 178796 | Coding | 4 | 114 | gagcaccaccggcgagtgg | 48 | 61 |

TABLE 1-continued

Inhibition of human eIF4E-BP1 mRNA levels in T-24 cells by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 178800 | Coding | 4 | 340 | gcaggtggctctggctggct | 69 | 62 |
| 178802 | Coding | 4 | 154 | tcgtgctgtagtccccgggc | 78 | 63 |

As shown in Table 1, SEQ ID NOs 27, 28, 29, 30, 32, 38, 44, 45, 47, 48, 49, 56, 59, 61, 62 and 63 demonstrated at least 32% inhibition of human eIF4E-BP1 expression in this assay and are therefore preferred. The target regions to which these preferred sequences are complementary are herein referred to as "preferred target segments" and are therefore preferred for targeting by compounds of the present invention. These preferred target segments are shown in Table 5. These sequences are shown to contain thymine (T) but one of skill in the art will appreciate that thymine (T) is generally replaced by uracil (U) in RNA sequences. The sequences represent the reverse complement of the preferred antisense compounds disclosed herein. "Target site" indicates the first (5'-most) nucleotide number on the particular target nucleic acid to which the oligonucleotide binds. Also shown in Table 5 is the species in which each of the preferred target segments was found.

SEQ ID NOs 52 and 53 are cross species antisense oligonucleotides which are also complementary to the mouse eIF4E-BP1 nucleic acid target.

In accordance with the present invention, a second series of antisense compounds was designed to target different regions of the mouse eIF4E-BP1 RNA, using published sequences (GenBank® accession number NM_004095.2, incorporated herein as SEQ ID NO: 4 and the complement of nucleotides 78114 to 108765 of the sequence with GenBank® accession number NT_078038.1, incorporated herein as SEQ ID NO: 26). The compounds are shown in Tables 1 and 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on mouse eIF4E-BP1 mRNA levels by quantitative real-time PCR as described in other examples herein. Data, shown in Table 2, are averages from two experiments in which b.END cells were treated with 150 nM of the antisense oligonucleotides of the present invention. SEQ ID NO: 2 was used as the control oligonucleotide in this assay. If present "N.D." indicates "no data".

TABLE 2

Inhibition of human eIF4E-BP1 mRNA levels in A549 cells by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 322838 | Coding | 4 | 152 | gtgctgtagtccccgggcgg | 62 | 64 |
| 322839 | Coding | 4 | 179 | gtgctgaagagcgtgccgcc | 64 | 65 |
| 322841 | Coding | 4 | 219 | gaatttccggtcatagatga | 0 | 66 |
| 322842 | Coding | 4 | 224 | atcaggaatttccggtcata | 32 | 67 |
| 322843 | Coding | 4 | 229 | actccatcaggaatttccgg | 73 | 68 |
| 347619 | 5'UTR | 4 | 43 | tctcctgtgcgctgcacccg | 67 | 69 |
| 347620 | Start Codon | 4 | 45 | ggtctcctgtgcgctgcacc | 75 | 70 |
| 347621 | Start Codon | 4 | 50 | gacatggtctcctgtgcgct | 72 | 71 |
| 347622 | Start Codon | 4 | 55 | ccccggacatggtctcctgt | 89 | 72 |
| 347623 | Start Codon | 4 | 57 | gccccggacatggtctcct | 86 | 73 |
| 347624 | Start Codon | 4 | 60 | gctgccccggacatggtct | 83 | 74 |
| 347625 | Coding | 4 | 68 | ctgcagctgctgcccccgga | 35 | 75 |
| 347626 | Coding | 4 | 73 | tctggctgcagctgctgccc | 48 | 76 |
| 347627 | Coding | 4 | 157 | gggtcgtgctgtagtccccg | 74 | 77 |
| 347628 | Coding | 4 | 231 | acactccatcaggaatttcc | 45 | 78 |
| 347629 | Coding | 4 | 236 | ttccgacactccatcaggaa | 80 | 79 |
| 347630 | Coding | 4 | 238 | agttccgacactccatcagg | 76 | 80 |
| 347631 | Coding | 4 | 244 | caggtgagttccgacactcc | 80 | 81 |
| 347632 | Coding | 4 | 251 | ttggtcacaggtgagttccg | 83 | 82 |
| 347633 | Coding | 4 | 258 | gggtgttttggtcacaggtg | 55 | 83 |
| 347634 | Coding | 4 | 279 | aatggtgggcagatcccttg | 43 | 84 |
| 347635 | Coding | 4 | 284 | cccggaatggtgggcagatc | 52 | 85 |
| 347636 | Coding | 4 | 290 | gtgaccccggaatggtggg | 15 | 86 |
| 347637 | Coding | 4 | 295 | ggctggtgaccccggaatg | 78 | 87 |
| 347638 | Coding | 4 | 296 | gggctggtgaccccggaat | 0 | 88 |
| 347639 | Coding | 4 | 304 | cactgaagggctggtgacc | 42 | 89 |
| 347640 | Coding | 4 | 306 | atcactggaagggctggtga | 60 | 90 |
| 347641 | Coding | 4 | 336 | gtggctctggctggcttcca | 81 | 91 |
| 347642 | Coding | 4 | 346 | tattgcgcaggtggctctgg | 26 | 92 |
| 347643 | Coding | 4 | 351 | tgggctattgcgcaggtggc | 63 | 93 |
| 347644 | Coding | 4 | 358 | tatcttctgggctattgcgc | 63 | 94 |
| 347645 | Coding | 4 | 359 | ttatcttctgggctattgcg | 67 | 95 |
| 347646 | Coding | 4 | 368 | cccgcccgcttatcttctgg | 59 | 96 |

TABLE 2-continued

Inhibition of human eIF4E-BP1 mRNA levels in A549 cells by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 347647 | Coding | 4 | 383 | tgtgactcttcaccgcccgc | 81 | 97 |
| 347648 | Coding | 4 | 389 | tcaaactgtgactcttcacc | 69 | 98 |
| 347649 | Coding | 4 | 392 | atctcaaactgtgactcttc | 57 | 99 |
| 347650 | Coding | 4 | 394 | ccatctcaaactgtgactct | 60 | 100 |
| 347651 | Stop Codon | 4 | 411 | gctggtgctttaaatgtcca | 69 | 101 |
| 347652 | 3'UTR | 4 | 423 | ctccacacgatggctggtgc | 91 | 102 |
| 347653 | 3'UTR | 4 | 428 | tagtgctccacacgatggct | 92 | 103 |
| 347654 | 3'UTR | 4 | 436 | cccccttggtagtgctccaca | 90 | 104 |
| 347655 | 3'UTR | 4 | 438 | ggccccttggtagtgctcca | 76 | 105 |
| 347656 | 3'UTR | 4 | 459 | cctcccaggaaggccctgag | 72 | 106 |
| 347657 | 3'UTR | 4 | 466 | tgggactcctcccaggaagg | 76 | 107 |
| 347658 | 3'UTR | 4 | 470 | ctggtgggactcctcccagg | 87 | 108 |
| 347659 | 3'UTR | 4 | 476 | gcctggctggtgggactcct | 96 | 109 |
| 347660 | 3'UTR | 4 | 481 | ataaggcctggctggtggga | 33 | 110 |
| 347661 | 3'UTR | 4 | 484 | ttcataaggcctggctggtg | 91 | 111 |
| 347662 | 3'UTR | 4 | 494 | tatgatcactttcataaggc | 86 | 112 |
| 347663 | 3'UTR | 4 | 499 | cccagtatgatcactttcat | 79 | 113 |
| 347664 | 3'UTR | 4 | 506 | acgcctgcccagtatgatca | 76 | 114 |
| 347665 | 3'UTR | 4 | 525 | ggtgtccgaccccacgccaa | 89 | 115 |
| 347666 | 3'UTR | 4 | 550 | ccctgagtgagggagaaagg | 70 | 116 |
| 347667 | 3'UTR | 4 | 587 | gtatctgctggtgttcacga | 95 | 117 |
| 347668 | 3'UTR | 4 | 593 | aaggaggtatctgctggtgt | 82 | 118 |
| 347669 | 3'UTR | 4 | 599 | aggcacaaggaggtatctgc | 86 | 119 |
| 347670 | 3'UTR | 4 | 611 | ctgcatcagtggaggcacaa | 79 | 120 |
| 347671 | 3'UTR | 4 | 616 | agctcctgcatcagtggagg | 82 | 121 |
| 347672 | 3'UTR | 4 | 618 | gcagctcctgcatcagtgga | 77 | 122 |
| 347673 | 3'UTR | 4 | 666 | ggcccttggctgcagggtgt | 70 | 123 |
| 347674 | 3'UTR | 4 | 672 | cttcctggcccttggctgca | 67 | 124 |
| 347675 | 3'UTR | 4 | 676 | tccacttcctggcccttggc | 87 | 125 |
| 347676 | 3'UTR | 4 | 678 | tgtccacttcctggcccttg | 92 | 126 |
| 347677 | 3'UTR | 4 | 680 | cttgtccacttcctggccct | 89 | 127 |
| 347678 | 3'UTR | 4 | 687 | gttcgttcttgtccacttcc | 93 | 128 |
| 347679 | 3'UTR | 4 | 693 | ggaagggttcgttcttgtcc | 75 | 129 |
| 347680 | 3'UTR | 4 | 697 | ggaaggaagggttcgttctt | 68 | 130 |
| 347681 | 3'UTR | 4 | 705 | gatcattcggaaggaagggt | 69 | 131 |
| 347682 | 3'UTR | 4 | 709 | tgctgatcattcggaaggaa | 87 | 132 |
| 347683 | 3'UTR | 4 | 742 | gtggttgcgccccagcagc | 80 | 133 |
| 347684 | 3'UTR | 4 | 767 | ccaagcacatcaacctaagg | 77 | 134 |
| 347685 | Intron | 26 | 14746 | tacaactccccacgcaggag | 23 | 135 |
| 347686 | Intron | 26 | 19263 | acatcattgtgaaattcaca | 70 | 136 |
| 347687 | Intron | 26 | 25252 | cagctgagattcatttctta | 53 | 137 |
| 347688 | Intron 1: exon 2 junction | 26 | 26963 | cctggtacctagaagggaac | 0 | 138 |
| 347689 | Intron | 26 | 29235 | caaagcgggagcaggcatgt | 55 | 139 |

As shown in Table 2, SEQ ID NOs 64, 65, 67, 68, 69, 70, 71, 72, 73, 74, 75, 76, 77, 78, 79, 80, 81, 82, 83, 84, 85, 87, 89, 90, 91, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 136, 137 and 139 demonstrated at least 32% inhibition of human eIF4E-BP1 expression in this assay and are therefore preferred. The target regions to which these preferred sequences are complementary are herein referred to as "preferred target segments" and are therefore preferred for targeting by compounds of the present invention. These preferred target segments are shown in Table 5. These sequences are shown to contain thymine (T) but one of skill in the art will appreciate that thymine (T) is generally replaced by uracil (U) in RNA sequences. The sequences represent the reverse complement of the preferred antisense compounds disclosed herein. "Target site" indicates the first (5'-most) nucleotide number on the particular target nucleic acid to which the oligonucleotide binds. Also shown in Table 5 is the species in which each of the preferred target segments was found.

SEQ ID NOs 51, 64, 65, 66, 67 and 68 are cross species antisense oligonucleotides which are also complementary to the rat eIF4E-BP1 nucleic acid target.

SEQ ID NOs 64, 65, 76 and 81 are cross species antisense oligonucleotides which are also complementary to the mouse eIF4E-BP1 nucleic acid target.

Example 12

Antisense Inhibition of Mouse eIF4E-BP1 Expression by Chimeric Phosphorothioate Oligonucleotides having 2'-MOE Wings and a Deoxy Gap In accordance with the present invention, a second series of antisense compounds was designed to target different regions of the mouse eIF4E-BP1 RNA, using published sequences (GenBank® accession number NM_007918.2, incorporated herein as SEQ ID NO: 11 and GenBank® accession number NM_007918.1, incorporated herein as SEQ ID NO: 25). The compounds are shown in Table 3. "Target site" indicates the first (5'-most) nucleotide number on the particular target nucleic acid to which the compound binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytosine residues are 5-methylcytosines. The compounds were analyzed for their effect on mouse eIF4E-BP1 mRNA levels by quantitative real-time PCR as described in other examples herein. Data, shown in Table 3, are averages from two experiments in which b.END cells were treated with 100 nM of the antisense oligonucleotides of the present invention. SEQ ID NO: 2 was used as the control oligonucleotide in this assay. If present, "N.D." indicates "no data".

TABLE 3

Inhibition of mouse eIF4E-BP1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 229661 | Start Codon | 25 | 43 | gcccgccgacatgtctcctg | 84 | 140 |
| 229662 | Stop Codon | 11 | 352 | gctggtcccttaaatgtcca | 94 | 141 |
| 229663 | 3'UTR | 11 | 489 | cagagctggcaccctgagtg | 81 | 142 |
| 229664 | 3'UTR | 11 | 731 | tttatttcctgtcagggaaa | 6 | 143 |
| 229665 | 3'UTR | 11 | 573 | gagtgagagtcattccctg | 88 | 144 |
| 229666 | 3'UTR | 11 | 606 | tccactcgctggagctccat | 89 | 145 |
| 229667 | 3'UTR | 11 | 478 | ccctgagtgaggagcaggac | 78 | 146 |
| 229668 | 3'UTR | 11 | 609 | gagtccactcgctggagctc | 79 | 147 |
| 229669 | 3'UTR | 11 | 427 | ggtatgaggcctgaatgctg | 84 | 148 |
| 229670 | 3'UTR | 11 | 379 | gacatagaagcatcattgcg | 86 | 149 |
| 229671 | 3'UTR | 11 | 685 | aacccagcctaaggaaagat | 64 | 150 |
| 229672 | 3'UTR | 11 | 367 | tcattgcgtcctacggctgg | 88 | 151 |
| 229673 | 3'UTR | 11 | 608 | agtccactcgctggagctcc | 82 | 152 |
| 229674 | 3'UTR | 11 | 416 | tgaatgctgtgcagctctcc | 87 | 153 |
| 229675 | Coding | 11 | 242 | tggtagggctagtgacccca | 86 | 154 |
| 229676 | Coding | 11 | 316 | ttcaccgcctgcccgcttat | 76 | 155 |
| 229677 | 3'UTR | 11 | 730 | ttatttcctgtcagggaaag | 77 | 156 |
| 229678 | Coding | 25 | 322 | cagttggctctggctggctt | 86 | 157 |
| 229679 | 3'UTR | 11 | 632 | agatcattctgatagactcc | 82 | 158 |
| 229680 | Coding | 11 | 198 | ggtgttttggccacaggtga | 83 | 159 |
| 229681 | 3'UTR | 11 | 605 | ccactcgctggagctccatg | 88 | 160 |
| 229682 | 3'UTR | 11 | 575 | gtgagtgagagtcattcccc | 91 | 161 |
| 229683 | Coding | 11 | 264 | gcttgcatgggaggctcatc | 89 | 162 |
| 229684 | Coding | 11 | 180 | gagttccgacactccatcag | 77 | 163 |
| 229685 | 3'UTR | 11 | 607 | gtccactcgctggagctcca | 90 | 164 |
| 229686 | 3'UTR | 11 | 622 | gatagactcctctgagtcca | 81 | 165 |
| 229687 | Start Codon | 11 | 11 | tgcagctgctgcccgccgac | 78 | 166 |
| 229688 | 3'UTR | 11 | 709 | agtaaaagtgtggctttccc | 89 | 167 |
| 229690 | Coding | 25 | 315 | ctctggctggcttgcatggg | 71 | 168 |
| 229692 | 3'UTR | 11 | 688 | ggtaacccagcctaaggaaa | 64 | 169 |
| 229694 | Coding | 11 | 100 | cggagtggtgctgtagtccc | 55 | 170 |
| 229696 | Coding | 11 | 174 | cgacactccatcagaaattt | 84 | 171 |
| 229698 | 3'UTR | 11 | 528 | gcacaaggaggtatgtgctg | 70 | 172 |
| 229700 | Coding | 11 | 168 | tccatcagaaatttccggtc | 88 | 173 |
| 229702 | Coding | 11 | 151 | gtcatagataatcctggttc | 72 | 174 |
| 229704 | Coding | 11 | 148 | atagataatcctggttcctc | 0 | 175 |
| 229706 | 3'UTR | 11 | 483 | tggcaccctgagtgaggagc | 76 | 176 |

As shown in Table 3, SEQ ID NOs 140, 141, 142, 144, 145, 146, 147, 148, 149, 150, 151, 152, 153, 154, 155, 156, 157, 158, 159, 160, 161, 162, 163, 164, 165, 166, 167, 168, 169, 171, 172, 173, 174 and 176 demonstrated at least 61% inhibition of mouse eIF4E-BP1 expression in this experiment and are therefore preferred. The target regions to which these preferred sequences are complementary are herein referred to as "preferred target segments" and are therefore preferred for targeting by compounds of the present invention. These preferred target segments are shown in Table 5. These sequences are shown to contain thymine (T) but one of skill in the art will appreciate that thymine (T) is generally replaced by uracil (U) in RNA sequences. The sequences represent the reverse complement of the preferred antisense compounds disclosed herein. "Target site" indicates the first (5'-most) nucleotide number on the particular target nucleic acid to which the oligonucleotide binds. Also shown in Table 5 described in is the species in which each of the preferred target segments was found.

SEQ ID NO: 77 is a cross species antisense oligonucleotide which is also complementary to the rat eIF4E-BP1 nucleic acid target.

Example 13

Antisense Inhibition of Rat eIF4E-BP1 Expression by Chimeric Phosphorothioate Oligonucleotides Having 2'-MOE Wings and a Deoxy Gap In accordance with the present invention, a third series of antisense compounds was designed to target different regions of the rat eIF4E-BP1 RNA, using published sequences (GenBank® accession number NM_053857.1, incorporated herein as SEQ ID NO: 18). An additional antisense compound was designed to target eIF4E-BP1 from the *R. spretus* species of rat, using published sequences (the complement of the sequence with GenBank® accession number AI178828.1, incorporated herein as SEQ ID NO: 428). The compounds are shown in Table 4. "Target site" indicates the first (5'-most) nucleotide number on the particular target nucleic acid to which the compound binds. All compounds in Table 4 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytosine residues are 5-methylcytosines. The compounds were analyzed for their effect on rat eIF4E-BP1 mRNA levels by quantitative real-time PCR as described in other examples herein. Data, shown in Table 4, are averages from two experiments in which A10 cells were treated with the antisense oligonucleotides of the present invention. SEQ ID NO: 2 was used as the control oligonucleotide in this assay. If present, "N.D." indicates "no data".

TABLE 4

Inhibition of rat eIF4E-BP1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 178773 | Coding | 18 | 219 | ggtcgtgctgtagtccccgg | 86 | 51 |
| 229684 | Coding | 18 | 224 | gagttccgacactccatcag | 82 | 163 |
| 322831 | Start Codon | 18 | 37 | acatgtctcctgcacgccgc | 82 | 177 |
| 322832 | Start Codon | 18 | 42 | cgccgacatgtctcctgcac | 81 | 178 |
| 322833 | Start Codon | 18 | 48 | gctgcccgccgacatgtctc | 84 | 179 |
| 322834 | Start Codon | 18 | 53 | caactgctgcccgccgacat | 67 | 180 |
| 322835 | Coding | 18 | 63 | agtctggctgcaactgctgc | 84 | 181 |
| 322836 | Coding | 18 | 71 | cggctgggagtctggctgca | 79 | 182 |
| 322837 | Coding | 18 | 77 | atagcccggctgggagtctg | 81 | 183 |
| 322838 | Coding | 18 | 137 | gtgctgtagtccccggcgg | 75 | 64 |
| 322839 | Coding | 18 | 164 | gtgctgaagagcgtgccgcc | 78 | 65 |
| 322840 | Coding | 18 | 199 | tccggtcatagatgattctg | 78 | 184 |
| 322841 | Coding | 18 | 204 | gtggctctggctggcttcca | 44 | 91 |
| 322842 | Coding | 18 | 209 | tattgcgcaggtggctctgg | 64 | 92 |
| 322843 | Coding | 18 | 214 | tgggctattgcgcaggtggc | 72 | 93 |
| 322844 | Coding | 18 | 231 | cacaggcgagttccgacact | 75 | 185 |
| 322845 | Coding | 18 | 240 | tgttttggccacaggcgagt | 74 | 186 |
| 322846 | Coding | 18 | 272 | accctggaatggttggcag | 62 | 187 |
| 322847 | Coding | 18 | 277 | tagtgaccccctggaatggtt | 80 | 188 |
| 322848 | Coding | 18 | 282 | agggctagtgaccccctggaa | 71 | 189 |
| 322849 | Coding | 18 | 287 | ctggtagggctagtgacccc | 70 | 190 |
| 322850 | Coding | 18 | 292 | catcgctggtagggctagtg | 61 | 191 |
| 322851 | Coding | 18 | 297 | aggctcatcgctggtagggc | 84 | 192 |
| 322852 | Coding | 18 | 302 | atgggaggctcatcgctggt | 76 | 193 |
| 322853 | Coding | 18 | 308 | gcctgcatgggaggctcatc | 47 | 194 |
| 322854 | Coding | 18 | 316 | tctggctggcctgcatggga | 0 | 195 |
| 322855 | Coding | 18 | 322 | gatggctctggctggcctgc | 68 | 196 |
| 322856 | Coding | 18 | 340 | cttccgggctgctgtgcaga | 75 | 197 |
| 322857 | Coding | 18 | 346 | gcttatcttccgggctgctg | 76 | 198 |
| 322858 | Coding | 18 | 351 | tgcccgcttatcttccgggc | 40 | 199 |
| 322859 | Coding | 18 | 360 | ttcaccacctgcccgcttat | 25 | 200 |
| 322860 | Coding | 18 | 368 | tgtgactcttcaccacctgc | 69 | 201 |
| 322861 | Stop Codon | 18 | 389 | ccttaaatgtccatctcaaa | 65 | 202 |
| 322862 | Stop Codon | 18 | 394 | tggtcccttaaatgtccatc | 83 | 203 |
| 322863 | 3'UTR | 18 | 411 | tcactgcgtcctatggctgg | 93 | 204 |
| 322864 | 3'UTR | 18 | 419 | cagaagcatcactgcgtcct | 89 | 205 |
| 322865 | 3'UTR | 18 | 452 | gctgtggctctcctcccaag | 92 | 206 |
| 322866 | 3'UTR | 18 | 463 | aaggcctgactgctgtggct | 81 | 207 |
| 322867 | 3'UTR | 18 | 474 | ctgccgggtacaaggcctga | 81 | 208 |
| 322868 | 3'UTR | 18 | 481 | ccagtgtctgccgggtacaa | 90 | 209 |
| 322869 | 3'UTR | 18 | 492 | ccgatccacacccagtgtct | 82 | 210 |
| 322870 | 3'UTR | 18 | 499 | tgggtggccgatccacaccc | 54 | 211 |
| 322871 | 3'UTR | 18 | 505 | caggactgggtggccgatcc | 63 | 212 |
| 322872 | 3'UTR | 18 | 517 | ctgagtgaggagcaggactg | 50 | 213 |
| 322873 | 3'UTR | 18 | 522 | gtgccctgagtgaggagcag | 48 | 214 |
| 322874 | 3'UTR | 18 | 536 | ggaaggcagagcaggtgccc | 76 | 215 |
| 322875 | 3'UTR | 18 | 542 | caaaatgcgaaggcagagcag | 44 | 216 |
| 322876 | 3'UTR | 18 | 547 | attcacaaaatgcgaaggcag | 69 | 217 |
| 322877 | 3'UTR | 18 | 554 | tgctggtattcacaaaatgg | 84 | 218 |
| 322878 | 3'UTR | 18 | 560 | ggtatgtgctggtattcaca | 83 | 219 |
| 322879 | 3'UTR | 18 | 563 | ggaggtatgtgctggtattc | 76 | 220 |

TABLE 4-continued

Inhibition of rat eIF4E-BP1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 322880 | 3'UTR | 18 | 567 | acaaggaggtatgtgctggt | 88 | 221 |
| 322881 | 3'UTR | 18 | 572 | gaggcacaaggaggtatgtg | 66 | 222 |
| 322882 | 3'UTR | 18 | 576 | aacagaggcacaaggaggta | 74 | 223 |
| 322883 | 3'UTR | 18 | 579 | atcaacagaggcacaaggag | 79 | 224 |
| 322884 | 3'UTR | 18 | 582 | agtatcaacagaggcacaag | 66 | 225 |
| 322885 | 3'UTR | 18 | 592 | gtagcagctcagtatcaaca | 84 | 226 |
| 322886 | 3'UTR | 18 | 598 | cctggagtagcagctcagta | 84 | 227 |
| 322887 | 3'UTR | 18 | 600 | accctggagtagcagctcag | 85 | 228 |
| 322888 | 3'UTR | 18 | 607 | agtcattaccctggagtagc | 88 | 229 |
| 322889 | 3'UTR | 18 | 612 | gtgagagtcattaccctgga | 89 | 230 |
| 322890 | 3'UTR | 18 | 618 | gtgtaggtgagagtcattac | 73 | 231 |
| 322891 | 3'UTR | 18 | 652 | ctgtgtccactcgctggcgc | 95 | 232 |
| 322892 | 3'UTR | 18 | 657 | ctcctctgtgtccactcgct | 95 | 233 |
| 322893 | 3'UTR | 18 | 676 | gccagatcattccgacagac | 97 | 234 |
| 322894 | 3'UTR | 18 | 680 | aattgccagatcattccgac | 85 | 235 |
| 322895 | 3'UTR | 18 | 686 | ggctagaattgccagatcat | 82 | 236 |
| 322896 | 3'UTR | 18 | 708 | gtgggtgtgctccagaggtt | 81 | 237 |
| 322897 | 3'UTR | 18 | 717 | taaggtaaggtgggtgtgct | 51 | 238 |
| 322898 | 3'UTR | 18 | 724 | cccaacctaaggtaaggtgg | 69 | 239 |
| 322899 | 3'UTR | 18 | 730 | aggtaccccaacctaaggta | 73 | 240 |
| 322900 | 3'UTR | 18 | 742 | ggtggctttcccaggtaccc | 88 | 241 |
| 322901 | 3'UTR | 18 | 744 | agggtggctttcccaggtac | 87 | 242 |
| 322902 | 3'UTR | 18 | 756 | ggaaagaagtaaagggtggc | 61 | 243 |
| 322903 | 3'UTR | 18 | 773 | cttttatttcctctcaggga | 86 | 244 |
| 322904 | 3'UTR | 18 | 787 | tagggtaaatgtggcttta | 68 | 245 |
| 322905 | 3'UTR | 18 | 812 | ttcagacagggcccggctgt | 60 | 246 |
| 322906 | Stop Codon | 428 | 579 | agtaaacggtgtcatcatat | 69 | 429 |

As shown in Table 4, SEQ ID NOs 51, 64, 65, 92, 93, 163, 177, 178, 179, 180, 181, 182, 183, 184, 185, 186, 187, 188, 189, 190, 191, 192, 193, 196, 197, 198, 201, 202, 203, 204, 205, 206, 207, 208, 209, 210, 212, 215, 217, 218, 219, 220, 221, 222, 223, 224, 225, 226, 227, 228, 229, 230, 231, 232, 233, 234, 235, 236, 237, 239, 240, 241, 242, 243, 244, 245, 246 and 429 demonstrated at least 55% inhibition of rat eIF4E-BP1 expression in this experiment and are therefore preferred. These preferred target segments are shown in Table 5. The target regions to which these preferred sequences are complementary are herein referred to as "preferred target segments" and are therefore preferred for targeting by compounds of the present invention. These sequences are shown to contain thymine (T) but one of skill in the art will appreciate that thymine (T) is generally replaced by uracil (U) in RNA sequences. The sequences represent the reverse complement of the preferred antisense compounds disclosed herein. "Target site" indicates the first (5'-most) nucleotide number on the particular target nucleic acid to which the compound binds. Also shown in Table 5 is the species in which each of the preferred target segments was found.

SEQ ID NOs 177, 179, 182, 190, 191, 192, 193, 198, 199, 202, 203, 213, 221, 222, 245 are cross species antisense oligonucleotides which are also complementary to the mouse eIF4E-BP1 nucleic acid target.

TABLE 5

Sequence and position of preferred target segments identified in eIF4E-BP1

| SITE ID | TARGET SEQ ID NO | TARGET SITE | SEQUENCE | REV COMP OF SEQ ID | ACTIVE IN | SEQ ID NO |
|---|---|---|---|---|---|---|
| 93684 | 4 | 274 | gaagccagccagagccacct | 27 | H. sapiens | 247 |
| 81708 | 4 | 245 | ccagcccttccagtgatgag | 28 | H. sapiens | 248 |
| 93685 | 4 | 173 | tcctgatggagtgtcggaac | 29 | H. sapiens | 249 |
| 93686 | 4 | 229 | accattccgggggtcaccag | 30 | H. sapiens | 250 |
| 93688 | 4 | 281 | gccagagccacctgcgcaat | 32 | H. sapiens | 251 |
| 93694 | 4 | 332 | agtcacagtttgagatggac | 38 | H. sapiens | 252 |
| 93700 | 4 | 159 | ctatgaccggaaattcctga | 44 | H. sapiens | 253 |

TABLE 5-continued

Sequence and position of preferred target segments identified in eIF4E-BP1

| SITE ID | TARGET SEQ ID NO | TARGET SITE | SEQUENCE | REV COMP OF SEQ ID | ACTIVE IN | SEQ ID NO |
|---|---|---|---|---|---|---|
| 93701 | 4 | 224 | tgcccaccattccgggggtc | 45 | H. sapiens | 254 |
| 93703 | 4 | 12 | cagcagctgcagccagaccc | 47 | H. sapiens | 255 |
| 93704 | 4 | 237 | gggggtcaccagcccttcca | 48 | H. sapiens | 256 |
| 93705 | 4 | 162 | tgaccggaaattcctgatgg | 49 | H. sapiens | 257 |
| 93712 | 4 | 247 | agcccttccagtgatgagcc | 56 | H. sapiens | 258 |
| 93715 | 4 | 277 | gccagccagagccacctgcg | 59 | H. sapiens | 259 |
| 93717 | 4 | 50 | ccactcgccgggtggtgctc | 61 | H. sapiens | 260 |
| 93718 | 4 | 276 | agccagccagagccacctgc | 62 | H. sapiens | 261 |
| 93719 | 4 | 90 | gcccggggactacagcacga | 63 | H. sapiens | 262 |
| 238985 | 4 | 152 | ccgcccggggactacagcac | 64 | H. sapiens | 263 |
| 238986 | 4 | 179 | ggcggcacgctcttcagcac | 65 | H. sapiens | 264 |
| 238989 | 4 | 224 | tatgaccggaaattcctgat | 67 | H. sapiens | 265 |
| 238990 | 4 | 229 | ccggaaattcctgatggagt | 68 | H. sapiens | 266 |
| 260811 | 4 | 43 | cgggtgcagcgcacaggaga | 69 | H. sapiens | 267 |
| 260812 | 4 | 45 | ggtgcagcgcacaggagacc | 70 | H. sapiens | 268 |
| 260813 | 4 | 50 | agcgcacaggagaccatgtc | 71 | H. sapiens | 269 |
| 260814 | 4 | 55 | acaggagaccatgtccgggg | 72 | H. sapiens | 270 |
| 260815 | 4 | 57 | aggagaccatgtccggggggc | 73 | H. sapiens | 271 |
| 260816 | 4 | 60 | agaccatgtccgggggcagc | 74 | H. sapiens | 272 |
| 260817 | 4 | 68 | tccgggggcagcagctgcag | 75 | H. sapiens | 273 |
| 260818 | 4 | 73 | gggcagcagctgcagccaga | 76 | H. sapiens | 274 |
| 260819 | 4 | 157 | cggggactacagcacgaccc | 77 | H. sapiens | 275 |
| 260820 | 4 | 231 | ggaaattcctgatggagtgt | 78 | H. sapiens | 276 |
| 260821 | 4 | 236 | ttcctgatggagtgtcggaa | 79 | H. sapiens | 277 |
| 260822 | 4 | 238 | cctgatggagtgtcggaact | 80 | H. sapiens | 278 |
| 260823 | 4 | 244 | ggagtgtcggaactcacctg | 81 | H. sapiens | 279 |
| 260824 | 4 | 251 | cggaactcacctgtgaccaa | 82 | H. sapiens | 280 |
| 260825 | 4 | 258 | cacctgtgaccaaaacaccc | 83 | H. sapiens | 281 |
| 260826 | 4 | 279 | caagggatctgcccaccatt | 84 | H. sapiens | 282 |
| 260827 | 4 | 284 | gatctgcccaccattccggg | 85 | H. sapiens | 283 |
| 260829 | 4 | 295 | cattccgggggtcaccagcc | 87 | H. sapiens | 284 |
| 260831 | 4 | 304 | ggtcaccagcccttccagtg | 89 | H. sapiens | 285 |
| 260832 | 4 | 306 | tcaccagcccttccagtgat | 90 | H. sapiens | 286 |
| 260833 | 4 | 336 | tggaagccagccagagccac | 91 | H. sapiens | 287 |
| 260835 | 4 | 351 | gccacctgcgcaatagccca | 93 | H. sapiens | 288 |
| 260836 | 4 | 358 | gcgcaatagcccagaagata | 94 | H. sapiens | 289 |

TABLE 5-continued

Sequence and position of preferred target segments identified in eIF4E-BP1

| SITE ID | TARGET SEQ ID NO | TARGET SITE | SEQUENCE | REV COMP OF SEQ ID | ACTIVE IN | SEQ ID NO |
|---|---|---|---|---|---|---|
| 260837 | 4 | 359 | cgcaatagcccagaagataa | 95 | H. sapiens | 290 |
| 260838 | 4 | 368 | ccagaagataagcgggcggg | 96 | H. sapiens | 291 |
| 260839 | 4 | 383 | gcgggcggtgaagagtcaca | 97 | H. sapiens | 292 |
| 260840 | 4 | 389 | ggtgaagagtcacagtttga | 98 | H. sapiens | 293 |
| 260841 | 4 | 392 | gaagagtcacagtttgagat | 99 | H. sapiens | 294 |
| 260842 | 4 | 394 | agagtcacagtttgagatgg | 100 | H. sapiens | 295 |
| 260843 | 4 | 411 | tggacatttaaagcaccagc | 101 | H. sapiens | 296 |
| 260844 | 4 | 423 | gcaccagccatcgtgtggag | 102 | H. sapiens | 297 |
| 260845 | 4 | 428 | agccatcgtgtggagcacta | 103 | H. sapiens | 298 |
| 260846 | 4 | 436 | tgtggagcactaccaagggg | 104 | H. sapiens | 299 |
| 260847 | 4 | 438 | tggagcactaccaaggggcc | 105 | H. sapiens | 300 |
| 260848 | 4 | 459 | ctcagggccttcctgggagg | 106 | H. sapiens | 301 |
| 260849 | 4 | 466 | ccttcctgggaggagtccca | 107 | H. sapiens | 302 |
| 260850 | 4 | 470 | cctgggaggagtcccaccag | 108 | H. sapiens | 303 |
| 260851 | 4 | 476 | aggagtcccaccagccaggc | 109 | H. sapiens | 304 |
| 260852 | 4 | 481 | tcccaccagccaggccttat | 110 | H. sapiens | 305 |
| 260853 | 4 | 484 | caccagccaggccttatgaa | 111 | H. sapiens | 306 |
| 260854 | 4 | 494 | gccttatgaaagtgatcata | 112 | H. sapiens | 307 |
| 260855 | 4 | 499 | atgaaagtgatcatactggg | 113 | H. sapiens | 308 |
| 260856 | 4 | 506 | tgatcatactgggcaggcgt | 114 | H. sapiens | 309 |
| 260857 | 4 | 525 | ttggcgtggggtcggacacc | 115 | H. sapiens | 310 |
| 260858 | 4 | 550 | cctttctccctcactcaggg | 116 | H. sapiens | 311 |
| 260859 | 4 | 587 | tcgtgaacaccagcagatac | 117 | H. sapiens | 312 |
| 260860 | 4 | 593 | acaccagcagatacctcctt | 118 | H. sapiens | 313 |
| 260861 | 4 | 599 | gcagatacctccttgtgcct | 119 | H. sapiens | 314 |
| 260862 | 4 | 611 | ttgtgcctccactgatgcag | 120 | H. sapiens | 315 |
| 260863 | 4 | 616 | cctccactgatgcaggagct | 121 | H. sapiens | 316 |
| 260864 | 4 | 618 | tccactgatgcaggagctgc | 122 | H. sapiens | 317 |
| 260865 | 4 | 666 | acaccctgcagccaagggcc | 123 | H. sapiens | 318 |
| 260866 | 4 | 672 | tgcagccaagggccaggaag | 124 | H. sapiens | 319 |
| 260867 | 4 | 676 | gccaagggccaggaagtgga | 125 | H. sapiens | 320 |
| 260868 | 4 | 678 | caagggccaggaagtggaca | 126 | H. sapiens | 321 |
| 260869 | 4 | 680 | agggccaggaagtggacaag | 127 | H. sapiens | 322 |
| 260870 | 4 | 687 | ggaagtggacaagaacgaac | 128 | H. sapiens | 323 |
| 260871 | 4 | 693 | ggacaagaacgaacccttcc | 129 | H. sapiens | 324 |
| 260872 | 4 | 697 | aagaacgaacccttccttcc | 130 | H. sapiens | 325 |

TABLE 5-continued

Sequence and position of preferred target segments identified in eIF4E-BP1

| SITE ID | TARGET SEQ ID NO | TARGET SITE | SEQUENCE | REV COMP OF SEQ ID | ACTIVE IN | SEQ ID NO |
|---|---|---|---|---|---|---|
| 260873 | 4 | 705 | acccttccttccgaatgatc | 131 | H. sapiens | 326 |
| 260874 | 4 | 709 | ttccttccgaatgatcagca | 132 | H. sapiens | 327 |
| 260875 | 4 | 742 | gctgctggggcgcaaccac | 133 | H. sapiens | 328 |
| 260876 | 4 | 767 | ccttaggttgatgtgcttgg | 134 | H. sapiens | 329 |
| 260878 | 26 | 19263 | tgtgaatttcacaatgatgt | 136 | H. sapiens | 330 |
| 260879 | 26 | 25252 | taagaaatgaatctcagctg | 137 | H. sapiens | 331 |
| 260881 | 26 | 29235 | acatgcctgctcccgctttg | 139 | H. sapiens | 332 |
| 146222 | 25 | 43 | caggagacatgtcggcgggc | 140 | M. musculus | 333 |
| 146223 | 11 | 352 | tggacatttaagggaccagc | 141 | M. musculus | 334 |
| 146224 | 11 | 489 | cactcagggtgccagctctg | 142 | M. musculus | 335 |
| 146226 | 11 | 615 | caggggaatgactctcactc | 144 | M. musculus | 336 |
| 146227 | 11 | 648 | atggagctccagcgagtgga | 145 | M. musculus | 337 |
| 146228 | 11 | 520 | gtcctgctcctcactcaggg | 146 | M. musculus | 338 |
| 146229 | 11 | 609 | gagctccagcgagtggactc | 147 | M. musculus | 339 |
| 146230 | 11 | 427 | cagcattcaggcctcatacc | 148 | M. musculus | 340 |
| 146231 | 11 | 379 | cgcaatgatgcttctatgtc | 149 | M. musculus | 341 |
| 146232 | 11 | 685 | atctttccttaggctgggtt | 150 | M. musculus | 342 |
| 146233 | 11 | 367 | ccagccgtaggacgcaatga | 151 | M. musculus | 343 |
| 146234 | 11 | 608 | ggagctccagcgagtggact | 152 | M. musculus | 344 |
| 146235 | 11 | 416 | ggagagctgcacagcattca | 153 | M. musculus | 345 |
| 146236 | 11 | 242 | tggggtcactagccctacca | 154 | M. musculus | 346 |
| 146237 | 11 | 316 | ataagcgggcaggcggtgaa | 155 | M. musculus | 347 |
| 146238 | 11 | 730 | ctttccctgacaggaaataa | 156 | M. musculus | 348 |
| 146239 | 25 | 322 | aagccagccagagccaactg | 157 | M. musculus | 349 |
| 146240 | 11 | 632 | ggagtctatcagaatgatct | 158 | M. musculus | 350 |
| 146241 | 11 | 198 | tcacctgtggccaaaacacc | 159 | M. musculus | 351 |
| 146242 | 11 | 605 | catggagctccagcgagtgg | 160 | M. musculus | 352 |
| 146243 | 11 | 575 | ggggaatgactctcactcac | 161 | M. musculus | 353 |
| 146244 | 11 | 264 | gatgagcctcccatgcaagc | 162 | M. musculus | 354 |
| 146245 | 11 | 180 | ctgatggagtgtcggaactc | 163 | M. musculus | 355 |
| 146246 | 11 | 607 | tggagctccagcgagtggac | 164 | M. musculus | 356 |
| 146247 | 11 | 622 | tggactcagaggagtctatc | 165 | M. musculus | 357 |
| 146248 | 11 | 11 | gtcggcgggcagcagctgca | 166 | M. musculus | 358 |
| 146249 | 11 | 709 | gggaaagccacactttact | 167 | M. musculus | 359 |
| 146250 | 25 | 315 | cccatgcaagccagccagag | 168 | M. musculus | 360 |
| 146251 | 11 | 688 | tttccttaggctgggttacc | 169 | M. musculus | 361 |

TABLE 5-continued

Sequence and position of preferred target segments identified in eIF4E-BP1

| SITE ID | TARGET SEQ ID NO | TARGET SITE | SEQUENCE | REV COMP OF SEQ ID | ACTIVE IN | SEQ ID NO |
|---|---|---|---|---|---|---|
| 146253 | 11 | 174 | aaatttctgatggagtgtcg | 171 | M. musculus | 362 |
| 146254 | 11 | 528 | cagcacatacctccttgtgc | 172 | M. musculus | 363 |
| 146255 | 11 | 168 | gaccggaaatttctgatgga | 173 | M. musculus | 364 |
| 146256 | 11 | 151 | gaaccaggattatctatgac | 174 | M. musculus | 365 |
| 146258 | 11 | 483 | gctcctcactcagggtgcca | 176 | M. musculus | 366 |
| 238978 | 18 | 37 | gcggcgtgcaggagacatgt | 177 | R. norvegicus | 367 |
| 238979 | 18 | 42 | gtgcaggagacatgtcggcg | 178 | R. norvegicus | 368 |
| 238980 | 18 | 48 | gagacatgtcggcgggcagc | 179 | R. norvegicus | 369 |
| 238981 | 18 | 53 | atgtcggcgggcagcagttg | 180 | R. norvegicus | 370 |
| 238982 | 18 | 63 | gcagcagttgcagccagact | 181 | R. norvegicus | 371 |
| 238983 | 18 | 71 | tgcagccagactcccagccg | 182 | R. norvegicus | 372 |
| 238984 | 18 | 77 | cagactcccagccgggctat | 183 | R. norvegicus | 373 |
| 238987 | 18 | 199 | cagaatcatctatgaccgga | 184 | R. norvegicus | 374 |
| 238991 | 18 | 231 | agtgtcggaactcgcctgtg | 185 | R. norvegicus | 375 |
| 238992 | 18 | 240 | actcgcctgtggccaaaaca | 186 | R. norvegicus | 376 |
| 238993 | 18 | 272 | ctgccaaccattccaggggt | 187 | R. norvegicus | 377 |
| 238994 | 18 | 277 | aaccattccaggggtcacta | 188 | R. norvegicus | 378 |
| 238995 | 18 | 282 | ttccaggggtcactagccct | 189 | R. norvegicus | 379 |
| 238996 | 18 | 287 | ggggtcactagccctaccag | 190 | R. norvegicus | 380 |
| 238997 | 18 | 292 | cactagccctaccagcgatg | 191 | R. norvegicus | 381 |
| 238998 | 18 | 297 | gccctaccagcgatgagcct | 192 | R. norvegicus | 382 |
| 238999 | 18 | 302 | accagcgatgagcctcccat | 193 | R. norvegicus | 383 |
| 239002 | 18 | 322 | gcaggccagccagagccatc | 196 | R. norvegicus | 384 |
| 239003 | 18 | 340 | tctgcacagcagcccggaag | 197 | R. norvegicus | 385 |
| 239004 | 18 | 346 | cagcagcccggaagataagc | 198 | R. norvegicus | 386 |
| 239007 | 18 | 368 | gcaggtggtgaagagtcaca | 201 | R. norvegicus | 387 |
| 239008 | 18 | 389 | tttgagatggacatttaagg | 202 | R. norvegicus | 388 |
| 239009 | 18 | 394 | gatggacatttaagggacca | 203 | R. norvegicus | 389 |
| 239010 | 18 | 411 | ccagccataggacgcagtga | 204 | R. norvegicus | 390 |
| 239011 | 18 | 419 | aggacgcagtgatgcttctg | 205 | R. norvegicus | 391 |
| 239012 | 18 | 452 | cttgggaggagagccacagc | 206 | R. norvegicus | 392 |
| 239013 | 18 | 463 | agccacagcagtcaggcctt | 207 | R. norvegicus | 393 |
| 239014 | 18 | 474 | tcaggccttgtacccggcag | 208 | R. norvegicus | 394 |
| 239015 | 18 | 481 | ttgtacccggcagacactgg | 209 | R. norvegicus | 395 |
| 239016 | 18 | 492 | agacactgggtgtggatcgg | 210 | R. norvegicus | 396 |
| 239018 | 18 | 505 | ggatcggccacccagtcctg | 212 | R. norvegicus | 397 |

TABLE 5-continued

Sequence and position of preferred target segments identified in eIF4E-BP1

| SITE ID | TARGET SEQ ID NO | TARGET SITE | SEQUENCE | REV COMP OF SEQ ID | ACTIVE IN | SEQ ID NO |
|---|---|---|---|---|---|---|
| 239021 | 18 | 536 | gggcacctgctctgccttcc | 215 | R. norvegicus | 398 |
| 239023 | 18 | 547 | ctgccttccatttgtgaat | 217 | R. norvegicus | 399 |
| 239024 | 18 | 554 | ccatttgtgaataccagca | 218 | R. norvegicus | 400 |
| 239025 | 18 | 560 | tgtgaataccagcacatacc | 219 | R. norvegicus | 401 |
| 239026 | 18 | 563 | gaataccagcacatacctcc | 220 | R. norvegicus | 402 |
| 239027 | 18 | 567 | accagcacatacctccttgt | 221 | R. norvegicus | 403 |
| 239028 | 18 | 572 | cacatacctccttgtgcctc | 222 | R. norvegicus | 404 |
| 239029 | 18 | 576 | tacctccttgtgcctctgtt | 223 | R. norvegicus | 405 |
| 239030 | 18 | 579 | ctccttgtgcctctgttgat | 224 | R. norvegicus | 406 |
| 239031 | 18 | 582 | cttgtgcctctgttgatact | 225 | R. norvegicus | 407 |
| 239032 | 18 | 592 | tgttgatactgagctgctac | 226 | R. norvegicus | 408 |
| 239033 | 18 | 598 | tactgagctgctactccagg | 227 | R. norvegicus | 409 |
| 239034 | 18 | 600 | ctgagctgctactccagggt | 228 | R. norvegicus | 410 |
| 239035 | 18 | 607 | gctactccagggtaatgact | 229 | R. norvegicus | 411 |
| 239036 | 18 | 612 | tccagggtaatgactctcac | 230 | R. norvegicus | 412 |
| 239037 | 18 | 618 | gtaatgactctcacctacac | 231 | R. norvegicus | 413 |
| 239038 | 18 | 652 | gcgccagcgagtggacacag | 232 | R. norvegicus | 414 |
| 239039 | 18 | 657 | agcgagtggacacagaggag | 233 | R. norvegicus | 415 |
| 239040 | 18 | 676 | gtctgtcggaatgatctggc | 234 | R. norvegicus | 416 |
| 239041 | 18 | 680 | gtcggaatgatctggcaatt | 235 | R. norvegicus | 417 |
| 239042 | 18 | 686 | atgatctggcaattctagcc | 236 | R. norvegicus | 418 |
| 239043 | 18 | 708 | aacctctggagcacacccac | 237 | R. norvegicus | 419 |
| 239045 | 18 | 724 | ccaccttaccttaggttggg | 239 | R. norvegicus | 420 |
| 239046 | 18 | 730 | taccttaggttggggtacct | 240 | R. norvegicus | 421 |
| 239047 | 18 | 742 | gggtacctgggaaagccacc | 241 | R. norvegicus | 422 |
| 239048 | 18 | 744 | gtacctgggaaagccaccct | 242 | R. norvegicus | 423 |
| 239049 | 18 | 756 | gccacccttacttctttcc | 243 | R. norvegicus | 424 |
| 239050 | 18 | 773 | tccctgagaggaaataaaag | 244 | R. norvegicus | 425 |
| 239051 | 18 | 787 | taaaagccacatttaccta | 245 | R. norvegicus | 426 |
| 239052 | 18 | 812 | acagccgggccctgtctgaa | 246 | R. norvegicus | 427 |
| 93690 | 428 | 579 | atatgatgacaccgtttact | 429 | R. norvegicus | 430 |
| 93707 | 18 | 219 | aattcctgatggagtgtcgg | 51 | R. norvegicus | 431 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of eIF4E-BP1.

According to the present invention, antisense compounds include antisense oligomeric compounds, antisense oligonucleotides, siRNAs, external guide sequence (EGS) oligonucleotides, alternate splicers, primers, probes, and other short oligomeric compounds which hybridize to at least a portion of the target nucleic acid.

Example 14

Western Blot Analysis of eIF4E-BP1 Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to eIF4E-BP1 is used, with a radiolabeled or fluorescently labeled secondary antibody directed against the primary antibody species. Bands are visualized using a PHOSPHORIMAGER™ (Molecular Dynamics, Sunnyvale, Calif.).

Example 15

Antisense Inhibition of Mouse eIF4E-BP1: Dose Response in b.END Cells

In a further embodiment of the invention, ISIS 229674, ISIS 229681, ISIS 229682, ISIS 229683, ISIS 229685 and ISIS 229688 were tested in a dose response experiment. ISIS 118920 (GTTCATTCTAAAGTGGTCAC, SEQ ID NO: 435) targets protein phosphatase catalytic subunit 2 alpha and was used as a control. b.END cells were plated in 24-well plates at a density of 40,000 cells per well. Cells were then treated with 1, 5, 10, 25, 50, 100 or 200 nM of antisense oligonucleotide, mixed with 3 μl of LIPOFECTIN™ (Invitrogen Life Technologies, Carlsbad, Calif.) per 100 nM oligonucleotide per 1 ml of media, as described by other examples herein. Expression of mouse eIF4E-BP1 was measured by real-time PCR as described by other examples herein. Data are expressed as percent inhibition of mouse eIF4E-BP1 mRNA, normalized to untreated control cells. The results are the average of three experiments and are shown in Table 6. A "+" preceding the numbers in the control oligonucleotide treated results indicates that gene expression increased.

Antisense inhibition of mouse eIF4E-BP1:
dose response in b.END cells

| | | % Inhibition of mouse eIF4E-BP1 Dose of oligonucleotide | | | | | | |
|---|---|---|---|---|---|---|---|---|
| ISIS # | SEQ ID NO | 1 nM | 5 nM | 10 nM | 25 nM | 50 nM | 100 nM | 200 nM |
| 229674 | 152 | 3 | 32 | 31 | 56 | 70 | 70 | 33 |
| 229681 | 160 | 9 | 25 | 40 | 65 | 84 | 82 | 81 |
| 229682 | 161 | 4 | 38 | 53 | 77 | 82 | 80 | 75 |

Antisense inhibition of mouse eIF4E-BP1:
dose response in b.END cells

| | | % Inhibition of mouse eIF4E-BP1 Dose of oligonucleotide | | | | | | |
|---|---|---|---|---|---|---|---|---|
| ISIS # | SEQ ID NO | 1 nM | 5 nM | 10 nM | 25 nM | 50 nM | 100 nM | 200 nM |
| 229683 | 162 | 3 | 31 | 41 | 54 | 73 | 58 | 58 |
| 229685 | 164 | 0 | 35 | 48 | 74 | 83 | 79 | 74 |
| 229688 | 167 | 19 | 35 | 43 | 58 | 75 | 75 | 65 |
| 118920 | 435 | +13 | 10 | 17 | 17 | 9 | +9 | +19 |

As demonstrated in Table 6, ISIS 229681, ISIS 229682, ISIS 229683, ISIS 229685 and ISIS 229688 inhibited mouse eIF4E-BP1 gene expression in a dose-dependent manner.

Example 16

Antisense Inhibition of Mouse eIF4E-BP1 Expression by Chimeric Phosphorothioate Oligonucleotides Having 2'-MOE Winds and a Deoxy Gap In accordance with the present invention, a second series of antisense compounds was designed to target different regions of the mouse eIF4E-BP1 RNA, using published sequences (GenBank® accession number NM_067918.2, incorporated herein as SEQ ID NO: 11; GenBank® accession number NM_007918.1, incorporated herein as SEQ ID NO: 25 and nucleotides 5645000 to 5663000 of the sequence with GenBank® accession number NT_039456.1, incorporated herein as SEQ ID NO: 436). The compounds are shown in Table 7. "Target site" indicates the first (5'-most) nucleotide number on the particular target nucleic acid to which the compound binds. All compounds in Table 7 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytosine residues are 5-methylcytosines. The compounds were analyzed for their effect on mouse eIF4E-BP1 mRNA levels by quantitative real-time PCR as described in other examples herein.

Additional probe and primers to mouse eIF4E-BP1 were designed to hybridize to a mouse eIF4E-BP1 sequence, using published sequence information (GenBank® accession number NM_007918.2, incorporated herein as SEQ ID NO: 11). For mouse eIF4E-BP1 the additional PCR primers were:
forward primer: CGGGCAGGCGGTGAA (SEQ ID NO: 437)
reverse primer: TCCTACGGCTGGTCCCTTAA (SEQ ID NO: 438) and the additional PCR probe was: FAM-AGT-CACAATTTGAGATGGACA-TAMRA (SEQ ID NO: 439) where FAM is the fluorescent reporter dye and TAMRA is the quencher dye.

Data, shown in Table 7, are averages from two experiments in which b.END cells were treated with 70 nM of the antisense oligonucleotides of the present invention. SEQ ID NO: 2 was used as the control oligonucleotide in this assay. If present, "N.D." indicates "no data".

TABLE 7

Antisense inhibition of mouse eIF4E-BP1 by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 178775 | Coding | 11 | 181 | tgagttccgacactccatca | 80 | 52 |
| 178777 | Coding | 11 | 183 | ggtgagttccgacactccat | 77 | 53 |
| 322831 | 5'UTR | 25 | 35 | acatgtctcctgcacgccgc | 89 | 177 |
| 322833 | Start Codon | 11 | 4 | gctgcccgccgacatgtctc | 72 | 179 |
| 322836 | Coding | 11 | 27 | cggctgggagtctggctgca | 73 | 182 |
| 322838 | Coding | 11 | 93 | gtgctgtagtccccgggcgg | 75 | 64 |
| 322839 | Coding | 11 | 120 | gtgctgaagagcgtgccgcc | 61 | 65 |
| 322849 | Coding | 11 | 243 | ctggtagggctagtgacccc | 71 | 190 |
| 322850 | Coding | 11 | 248 | catcgctggtagggctagtg | 73 | 191 |
| 322851 | Coding | 11 | 253 | aggctcatcgctggtagggc | 84 | 192 |
| 322852 | Coding | 11 | 258 | atgggaggctcatcgctggt | 80 | 193 |
| 322857 | Coding | 11 | 302 | gcttatcttccgggctgctg | 66 | 198 |
| 322858 | Coding | 11 | 307 | tgcccgcttatcttccgggc | 39 | 199 |
| 322861 | Stop Codon | 11 | 345 | ccttaaatgtccatctcaaa | 71 | 202 |
| 322862 | Stop Codon | 11 | 350 | tggtcccttaaatgtccatc | 84 | 203 |
| 322872 | 3'UTR | 11 | 476 | ctgagtgaggagcaggactg | 59 | 213 |
| 322880 | 3'UTR | 11 | 526 | acaaggaggtatgtgctggt | 75 | 221 |
| 322881 | 3'UTR | 11 | 531 | gaggcacaaggaggtatgtg | 72 | 222 |
| 322904 | 3'UTR | 11 | 747 | tagggtaaatgtggctttta | 86 | 245 |
| 347626 | 3'UTR | 11 | 17 | tctggctgcagctgctgccc | 68 | 76 |
| 347631 | 3'UTR | 11 | 185 | caggtgagttccgacactcc | 76 | 81 |
| 348647 | Intron 1 | 436 | 4809 | gccacccccttcagctagaat | 69 | 440 |
| 348648 | Intron 1 | 436 | 11960 | cggcagaatctgagtaaggg | 57 | 441 |
| 348649 | Intron 1: Exon 2 Junction | 436 | 13902 | taatcctggttcctggtggg | 57 | 442 |
| 348650 | Intron 2 | 436 | 14565 | cttccgtgacaataggagcc | 78 | 443 |
| 348651 | Intron 2: Exon 3 Junction | 436 | 15656 | actcttcacctgtggagaga | 82 | 444 |
| 348652 | Start Codon | 11 | 2 | tgcccgccgacatgtctcct | 5 | 445 |
| 348653 | Coding | 11 | 156 | ttccggtcatagataatcct | 72 | 446 |
| 348654 | Coding | 11 | 161 | gaaatttccggtcatagata | 52 | 447 |
| 348655 | Coding | 11 | 166 | catcagaaatttccggtcat | 70 | 448 |
| 348656 | Coding | 11 | 177 | ttccgacactccatcagaaa | 77 | 449 |
| 348657 | Coding | 11 | 192 | ttggccacaggtgagttccg | 81 | 450 |
| 348658 | Coding | 11 | 218 | tggctggcaggtcctttggg | 66 | 451 |
| 348659 | Coding | 11 | 226 | cccaggaatggctggcaggt | 75 | 452 |
| 348660 | Coding | 11 | 232 | agtgaccccaggaatggctg | 79 | 453 |
| 348661 | Coding | 11 | 266 | tggcttgcatgggaggctca | 83 | 454 |

TABLE 7-continued

Antisense inhibition of mouse eIF4E-BP1 by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 348662 | Coding | 11 | 271 | ctggttggcttgcatgggag | 41 | 455 |
| 348663 | Coding | 11 | 277 | ttggctctggttggcttgca | 65 | 456 |
| 348664 | Coding | 11 | 289 | gctgctgggcagttggctct | 67 | 457 |
| 348665 | Coding | 11 | 323 | gtgactcttcaccgcctgcc | 82 | 458 |
| 348666 | Coding | 11 | 333 | atctcaaattgtgactcttc | 58 | 459 |
| 348667 | Coding | 11 | 339 | atgtccatctcaaattgtga | 80 | 460 |
| 348668 | 3'UTR | 11 | 373 | gaagcatcattgcgtcctac | 90 | 461 |
| 348669 | 3'UTR | 11 | 455 | gtggccgacccacacccagt | 80 | 462 |
| 348670 | 3'UTR | 11 | 460 | actgggtggccgacccacac | 62 | 463 |
| 348671 | 3'UTR | 11 | 465 | gcaggactgggtggccgacc | 83 | 464 |
| 348672 | 3'UTR | 11 | 495 | tcaaggcagagctggcaccc | 79 | 465 |
| 348673 | 3'UTR | 11 | 513 | tgctggtgttcacaaaattc | 77 | 466 |
| 348674 | 3'UTR | 11 | 543 | tcggtatagacagaggcaca | 86 | 467 |
| 348675 | 3'UTR | 11 | 554 | gcagtagcagctcggtatag | 79 | 468 |
| 348676 | 3'UTR | 11 | 567 | gagtcattccctgcagtag | 81 | 469 |
| 348677 | 3'UTR | 11 | 598 | ctggagctccatgcagggag | 48 | 470 |
| 348678 | 3'UTR | 11 | 613 | ctctgagtccactcgctgga | 83 | 471 |
| 348679 | 3'UTR | 11 | 627 | attctgatagactcctctga | 76 | 472 |
| 348680 | 3'UTR | 11 | 643 | ctaggattgccagatcattc | 79 | 473 |
| 348681 | 3'UTR | 11 | 675 | aaggaaagatgggtgtgctc | 59 | 474 |
| 348682 | 3'UTR | 11 | 745 | gggtaaatgtggcttttatt | 63 | 475 |
| 348683 | 3'UTR | 11 | 750 | gcctagggtaaatgtggctt | 71 | 476 |
| 348684 | 3'UTR | 11 | 786 | tggaaaacagttcagacagg | 77 | 477 |
| 348685 | 3'UTR | 11 | 847 | gtacagggaaatcacaccat | 76 | 478 |
| 348686 | 3'UTR | 11 | 1333 | tgatggctcactaccatcta | 46 | 479 |
| 348687 | 3'UTR | 11 | 1408 | agtctacctaacatataata | 57 | 480 |
| 348688 | 3'UTR | 11 | 1575 | caagcacatatgataatgta | 58 | 481 |
| 348689 | 3'UTR | 11 | 1584 | ctggtataacaagcacatat | 68 | 482 |
| 348690 | 3'UTR | 11 | 1604 | tgctctgctgacccagagtg | 79 | 483 |
| 348691 | 3'UTR | 11 | 1628 | cagctgtaaattgacagtaa | 75 | 484 |
| 348692 | 3'UTR | 11 | 1654 | agagggctagcttcagccag | 64 | 485 |
| 348693 | 3'UTR | 11 | 1666 | gtccaggcccatagagggct | 48 | 486 |
| 348694 | 3'UTR | 11 | 1703 | ctgctactaaaaataattac | 13 | 487 |
| 348695 | 3'UTR | 11 | 1714 | ggtaacacttgctgctacta | 83 | 488 |
| 348696 | 3'UTR | 11 | 1719 | acaaaggtaacacttgctgc | 79 | 489 |
| 348697 | 3'UTR | 11 | 1739 | aaaggtgaccatctcactgg | 85 | 490 |

TABLE 7-continued

Antisense inhibition of mouse eIF4E-BP1 by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 348698 | 3'UTR | 11 | 1778 | atgtggaccgaaggctctac | 74 | 491 |
| 348699 | 3'UTR | 11 | 1813 | gcagcacacacagagatgat | 66 | 492 |
| 348700 | 3'UTR | 11 | 1860 | acctcagtaaaatcctatta | 65 | 493 |

As shown in Table 6, SEQ ID NOs 52, 53, 64, 65, 76, 81, 177, 179, 182, 190, 191, 192, 193, 198, 202, 203, 213, 221, 222, 245, 440, 441, 442, 443, 444, 446, 448, 449, 450, 451, 452, 453, 454, 456, 457, 458, 459, 460, 461, 462, 463, 464, 465, 466, 467, 468, 469, 471, 472, 473, 474, 475, 476, 477, 478, 480, 481, 482, 483, 484, 485, 488, 489, 490, 491, 492 and 493 demonstrated at least 57% inhibition of mouse eIF4E-BP1 expression in this experiment and are therefore preferred. The target regions to which these preferred sequences are complementary are herein referred to as "preferred target segments" and are therefore preferred for targeting by compounds of the present invention. The preferred target segments to which SEQ ID NOs 64, 65, 76, 81, 177, 179, 182, 190, 191, 192, 193, 198, 202, 203, 221, 222 and 245 are complementary are illustrated in Table 5. The preferred target segments to which SEQ ID NOs 52, 53, 213, 440, 441, 442, 443, 444, 446, 448, 449, 450, 451, 452, 453, 454, 456, 457, 458, 459, 460, 461, 462, 463, 464, 465, 466, 467, 468, 469, 471, 472, 473, 474, 475, 476, 477, 478, 480, 481, 482, 483, 484, 485, 488, 489, 490, 491, 492 and 493 are complementary are shown in Table 8. These sequences are shown to contain thymine (T) but one of skill in the art will appreciate that thymine (T) is generally replaced by uracil (U) in RNA sequences. The sequences represent the reverse complement of the preferred antisense compounds disclosed herein. "Target site" indicates the first (5'-most) nucleotide number on the particular target nucleic acid to which the compound binds. Also shown in Table 8 is the species in which each of the preferred target segments was found.

TABLE 8

Sequence and position of preferred target segments indentified in eIF4E-BP1

| SITE ID | TARGET SEQ ID NO | Target Site | SEQUENCE | REV COMP OF SEQ ID NO | ACTIVE IN | SEQ ID NO |
|---|---|---|---|---|---|---|
| 93708 | 11 | 181 | tgatggagtgtcggaactca | 52 | M. musculus | 494 |
| 93709 | 11 | 183 | atggagtgtcggaactcacc | 53 | M. musculus | 495 |
| 239019 | 11 | 476 | cagtcctgctcctcactcag | 213 | M. musculus | 496 |
| 261635 | 436 | 4809 | attctagctgaaggggtggc | 440 | M. musculus | 497 |
| 261636 | 436 | 11960 | cccttactcagattctgccg | 441 | M. musculus | 498 |
| 261637 | 436 | 13902 | cccaccaggaaccaggatta | 442 | M. musculus | 499 |
| 261638 | 436 | 14565 | ggctcctattgtcacggaag | 443 | M. musculus | 500 |
| 261639 | 436 | 15656 | tctctccacaggtgaagagt | 444 | M. musculus | 501 |
| 261641 | 11 | 156 | aggattatctatgaccggaa | 446 | M. musculus | 502 |
| 261643 | 11 | 166 | atgaccggaaatttctgatg | 448 | M. musculus | 503 |
| 261644 | 11 | 177 | tttctgatggagtgtcggaa | 449 | M. musculus | 504 |
| 261645 | 11 | 192 | cggaactcacctgtggccaa | 450 | M. musculus | 505 |
| 261646 | 11 | 218 | cccaaaggacctgccagcca | 451 | M. musculus | 506 |
| 261647 | 11 | 226 | acctgccagccattcctggg | 452 | M. musculus | 507 |
| 261648 | 11 | 232 | cagccattcctggggtcact | 453 | M. musculus | 508 |
| 261649 | 11 | 266 | tgagcctcccatgcaagcca | 454 | M. musculus | 509 |
| 261651 | 11 | 277 | tgcaagccaaccagagccaa | 456 | M. musculus | 510 |
| 261652 | 11 | 289 | agagccaactgcccagcagc | 457 | M. musculus | 511 |

TABLE 8-continued

Sequence and position of preferred target segments indentified in eIF4E-BP1

| SITE ID | TARGET SEQ ID NO | Target Site | SEQUENCE | REV COMP OF SEQ ID NO | ACTIVE IN | SEQ ID NO |
|---|---|---|---|---|---|---|
| 261653 | 11 | 323 | ggcaggcggtgaagagtcac | 458 | M. musculus | 512 |
| 261654 | 11 | 333 | gaagagtcacaatttgagat | 459 | M. musculus | 513 |
| 261655 | 11 | 339 | tcacaatttgagatggacat | 460 | M. musculus | 514 |
| 261656 | 11 | 373 | gtaggacgcaatgatgcttc | 461 | M. musculus | 515 |
| 261657 | 11 | 455 | actgggtgtgggtcggccac | 462 | M. musculus | 516 |
| 261658 | 11 | 460 | gtgtgggtcggccacccagt | 463 | M. musculus | 517 |
| 261659 | 11 | 465 | ggtcggccacccagtcctgc | 464 | M. musculus | 518 |
| 261660 | 11 | 495 | gggtgccagctctgccttga | 465 | M. musculus | 519 |
| 261661 | 11 | 513 | gaattttgtgaacaccagca | 466 | M. musculus | 520 |
| 261662 | 11 | 543 | tgtgcctctgtctataccga | 467 | M. musculus | 521 |
| 261663 | 11 | 554 | ctataccgagctgctactgc | 468 | M. musculus | 522 |
| 261664 | 11 | 567 | ctactgcaggggaatgactc | 469 | M. musculus | 523 |
| 261666 | 11 | 613 | tccagcgagtggactcagag | 471 | M. musculus | 524 |
| 261667 | 11 | 627 | tcagaggagtctatcagaat | 472 | M. musculus | 525 |
| 261668 | 11 | 643 | gaatgatctggcaatcctag | 473 | M. musculus | 526 |
| 261669 | 11 | 675 | gagcacacccatctttcctt | 474 | M. musculus | 527 |
| 261670 | 11 | 745 | aataaaagccacatttaccc | 475 | M. musculus | 528 |
| 261671 | 11 | 750 | aagccacatttaccctaggc | 476 | M. musculus | 529 |
| 261672 | 11 | 786 | cctgtctgaactgttttcca | 477 | M. musculus | 530 |
| 261673 | 11 | 847 | atggtgtgatttccctgtac | 478 | M. musculus | 531 |
| 261675 | 11 | 1408 | tattatatgttaggtagact | 480 | M. musculus | 532 |
| 261676 | 11 | 1575 | tacattatcatatgtgcttg | 481 | M. musculus | 533 |
| 261677 | 11 | 1584 | atatgtgcttgttataccag | 482 | M. musculus | 534 |
| 261678 | 11 | 1604 | cactctgggtcagcagagca | 483 | M. musculus | 535 |
| 261679 | 11 | 1628 | ttactgtcaatttacagctg | 484 | M. musculus | 536 |
| 261680 | 11 | 1654 | ctggctgaagctagccctct | 485 | M. musculus | 537 |
| 261683 | 11 | 1714 | tagtagcagcaagtgttacc | 488 | M. musculus | 538 |
| 261684 | 11 | 1719 | gcagcaagtgttacctttgt | 489 | M. musculus | 539 |
| 261685 | 11 | 1739 | ccagtgagatggtcacctttt | 490 | M. musculus | 540 |
| 261686 | 11 | 1778 | gtagagccttcggtccacat | 491 | M. musculus | 541 |
| 261687 | 11 | 1813 | atcatctctgtgtgtgctgc | 492 | M. musculus | 542 |
| 261688 | 11 | 1860 | taataggattttactgaggt | 493 | M. musculus | 543 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of eIF4E-BP1.

According to the present invention, antisense compounds include antisense oligomeric compounds, antisense oligonucleotides, siRNAs, external guide sequence (EGS) oligonucleotides, alternate splicers, primers, probes, and other short oligomeric compounds which hybridize to at least a portion of the target nucleic acid.

Example 17

Reduction of Blood Glucose Levels in Ob/Ob Mice by Antisense Inhibition of eIF4E-BP1

Ob/ob mice have a mutation in the leptin gene which results in obesity and hyperglycemia. As such, these mice are a useful model for the investigation of obesity and diabetes and treatments designed to treat these conditions. In accordance with the present invention, compounds targeted to eIF4E-BP1 are tested in the ob/ob model of obesity and diabetes.

Seven-week old male C57Bl/6J-Lep ob/ob mice (Jackson Laboratory, Bar Harbor, Me.) are fed a diet with a fat content of 10-15% and are subcutaneously injected with oligonucleotides at a dose of 25 mg/kg two times per week for 4 weeks. eIF4E-BP1 antisense oligonucleotides used were ISIS 229685 (SEQ ID NO: 164) and ISIS 229688 (SEQ ID NO: 167). ISIS 116847, targeted to mouse PTEN, was used as a positive control. Saline-injected animals, leptin wildtype littermates (i.e. lean littermates) and ob/ob mice fed a standard rodent diet also serve as controls. After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from antisense inhibition of target mRNA, the ob/ob mice that receive antisense oligonucleotide treatment are further evaluated at the end of the treatment period for serum lipids, serum free fatty acids, serum cholesterol, liver triglycerides, fat tissue triglycerides and liver enzyme levels. Hepatic steatosis, or accumulation of lipids in the liver, is assessed by measuring the liver triglyceride content. Hepatic steatosis is assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are evaluated in the ob/ob mice treated with antisense oligonucleotides. Plasma glucose is measured at the start of the antisense oligonucleotide treatment and following two and four weeks of treatment. Both fed and fasted plasma glucose levels were measured. At start of study, the treatment groups of mice are chosen to have an average fed plasma glucose level of about 350 mg/dL. Plasma insulin is also measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose and insulin levels are measured before the insulin or glucose challenge and at 15, 20 or 30 minute intervals for up to 3 hours.

In mice treated with ISIS 229685 (SEQ ID NO: 164), an antisense inhibitor of eIF4E-BP1, plasma glucose levels were approximately 370 mg/dL at week 0, 390 mg/dL at week 2 and 200 mg/dL at week 4. In mice treated with ISIS 229688 (SEQ ID NO: 167), another antisense inhibitor of eIF4E-BP1, plasma glucose levels were approximately 370 mg/dL at week 0, 280 mg/dL at week 2 and 170 mg/dL at week 4. In contrast, mice treated with saline alone had fed plasma glucose levels of approximately 370 mg/dL at week 0, 445 mg/dL at week 2 and 320 mg/dL at week 4. Mice treated with a positive control oligonucleotide, ISIS 116847 (CT-GCTAGCCTCTGGATTTGA; SEQ ID NO: 544), targeted to PTEN, had fed plasma glucose levels of approximately 370 mg/dL at week 0, 245 mg/dL at week 2 and 150 mg/dL at week 4.

At the end of the study, serum transaminases were measured. AST levels were approximately 225 IU/L for saline treated mice, 225 IU/L for ISIS 229685-treated mice, 350 IU/L for ISIS 229688-treated mice and 500 IU/L for ISIS 116847-treated mice. ALT levels were approximately 310 IU/L for saline treated mice, 420 IU/L for ISIS 229685-treated mice, 460 IU/L for ISIS 229688-treated mice and 790 IU/L for ISIS 116847-treated mice.

Serum lipids were also measured at the end of the study. Cholesterol levels were approximately 230 mg/dL for saline treated mice, 290 mg/dL for ISIS 229685-treated mice, 280 mg/dL for ISIS 229688-treated mice and 250 mg/dL for ISIS 116847-treated mice. Triglycerides were approximately 140 mg/dL for saline treated mice, 110 mg/dL for ISIS 229685-treated mice, 100 mg/dL for ISIS 229688-treated mice and 120 mg/dL for ISIS 116847-treated mice.

eIF4E-BP1 mRNA levels in liver were measured at the end of study using RiboGreen™ RNA quantification reagent (Molecular Probes, Inc. Eugene, Oreg.) as taught in previous examples above. eIF4E-BP1 mRNA levels were reduced by approximately 54% in mice treated with ISIS 229685, and by approximately 52% in mice treated with ISIS 229688, when compared to saline treatment. Target reduction was actually increased by 32% in mice treated with ISIS 116847, the control oligonucleotide targeted to PTEN.

What is claimed is:

1. A compound comprising a modified oligonucleotide consisting of 13 to 50 linked nucleosides and having at least an 8 contiguous nucleobase portion of a nucleobase sequence which is complementary to nucleotides 423-457, nucleotides 459-495, nucleotides 484-544, nucleotides 550-569, nucleotides 587-637, nucleotides 666-728, nucleotides 742-761 or nucleotides 767-786 of SEQ ID NO:4 encoding eIF4E-BP1, wherein the modified oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned between the 5' wing segment and the 3' wing segment and wherein each of said nucleosides of each of said wing segments comprises a modified sugar.

2. The compound of claim 1 which is 15 to 30 nucleobases in length.

3. The compound of claim 1 having at least 90% complementarity with nucleotides 423-457, nucleotides 459-495, nucleotides 484-544, nucleotides 550-569, nucleotides 587-637, nucleotides 666-728, nucleotides 742-761 or nucleotides 767-786 of SEQ ID NO:4.

4. The compound of claim 1 having at least 95% complementarity with nucleotides 423-457, nucleotides 459-495, nucleotides 484-544, nucleotides 550-569, nucleotides 587-637, nucleotides 666-728, nucleotides 742-761 or nucleotides 767-786 of SEQ ID NO:4.

5. The compound of claim 1 having at least 99% complementarity with nucleotides 423-457, nucleotides 459-495, nucleotides 484-544, nucleotides 550-569, nucleotides 587-637, nucleotides 666-728, nucleotides 742-761 or nucleotides 767-786 of SEQ ID NO:4.

6. The compound of claim 1, wherein at least one modified sugar comprises a 2'-O-methoxyethyl.

7. The compound of claim 1, wherein at least one internucleoside linkage is a phosphorothioate internucleoside linkage.

8. The compound of claim 1, wherein at least one modified nucleobase is a 5-methylcytosine.

9. The compound of claim 1, wherein said compound comprises at least a 13-nucleobase portion of SEQ ID NO: 125, 126, 127 or 128.

10. The compound of claim 1, wherein said nucleobase sequence is selected from the group consisting of SEQ ID NOs: 125, 126, 127 and 128.

11. The compound of claim 1 wherein said nucleobase sequence is complementary to nucleotides 676-695, nucleotides 678-697, nucleotides 680-699, or nucleotides 687-706, all of SEQ ID NO: 4.

12. The compound of claim 1 wherein at least one of the modified sugars is a bicyclic sugar.

13. The compound of claim 1, wherein the modified oligonucleotide comprises:
a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each of said nucleosides of each of said wing segments comprises a 2'-O-methoxyethyl sugar; and wherein each internucleoside linkage is a phosphorothioate linkage.

14. The compound of claim 1, wherein the modified oligonucleotide consists of 20 linked nucleosides.

15. A composition comprising the modified oligonucleotide of claim 1 or a salt thereof and a pharmaceutically acceptable carrier or diluent.

16. The compound of claim 1 wherein said nucleobase sequence is complementary to nucleotides 423-457 of SEQ ID NO: 4.

17. The compound of claim 1 wherein said nucleobase sequence is complementary to nucleotides 459-495 of SEQ ID NO: 4.

18. The compound of claim 1 wherein said nucleobase sequence is complementary to nucleotides 484-544 of SEQ ID NO: 4.

19. The compound of claim 1 wherein said nucleobase sequence is complementary to nucleotides 550-569 of SEQ ID NO: 4.

20. The compound of claim 1 wherein said nucleobase sequence is complementary to nucleotides 587-637 of SEQ ID NO: 4.

21. The compound of claim 1 wherein said nucleobase sequence is complementary to nucleotides 666-728 of SEQ ID NO: 4.

22. The compound of claim 1 wherein said nucleobase sequence is complementary to nucleotides 742-761 of SEQ ID NO: 4.

23. The compound of claim 1 wherein said nucleobase sequence is complementary to nucleotides 767-786 of SEQ ID NO: 4.

24. The compound of claim 1 wherein said nucleobase sequence is complementary to nucleotides 676-706 of SEQ ID NO: 4.

25. The compound of claim 1 having 100% complementarity with nucleotides 423-457, nucleotides 459-495, nucleotides 484-544, nucleotides 550-569, nucleotides 587-637, nucleotides 666-728, nucleotides 742-761 or nucleotides 767-786 of SEQ ID NO:4.

26. A compound comprising a modified oligonucleotide consisting of 13 to 50 linked nucleosides and having a nucleobase sequence which is complementary to nucleotides 423-457, nucleotides 459-495, nucleotides 484-544, nucleotides 550-569, nucleotides 587-637, nucleotides 666-691, nucleotides 742-761 or nucleotides 767-786 of SEQ ID NO:4 encoding eIF4E-BP1.

27. The compound of claim 26 which is 15 to 30 nucleobases in length.

28. The compound of claim 26 comprising a DNA oligonucleotide.

29. The compound of claim 26 comprising an RNA oligonucleotide.

30. The compound of claim 26 which is a double-stranded oligonucleotide.

31. The compound of claim 26 comprising a chimeric oligonucleotide.

32. The compound of claim 26 wherein at least a portion of said compound hybridizes with RNA to form an oligonucleotide-RNA duplex.

33. The compound of claim 26 having at least 90% complementarity with nucleotides 423-457, nucleotides 459-495, nucleotides 484-544, nucleotides 550-569, nucleotides 587-637, nucleotides 666-691, nucleotides 742-761 or nucleotides 767-786 of SEQ ID NO:4.

34. The compound of claim 26 having at least 95% complementarity with nucleotides 423-457, nucleotides 459-495, nucleotides 484-544, nucleotides 550-569, nucleotides 587-637, nucleotides 666-691, nucleotides 742-761 or nucleotides 767-786 of SEQ ID NO:4.

35. The compound of claim 26 having at least 99% complementarity with nucleotides 423-457, nucleotides 459-495, nucleotides 484-544, nucleotides 550-569, nucleotides 587-637, nucleotides 666-691, nucleotides 742-761 or nucleotides 767-786 of SEQ ID NO:4.

36. The compound of claim 26 having 100% complementarity with nucleotides 423-457, nucleotides 459-495, nucleotides 484-544, nucleotides 550-569, nucleotides 587-637, nucleotides 666-691, nucleotides 742-761 or nucleotides 767-786 of SEQ ID NO:4.

37. The compound of claim 26 having at least one modified internucleoside linkage, modified sugar, or modified nucleobase.

38. The compound of claim 37, wherein at least one modified sugar comprises a 2'-O-methoxyethyl.

39. The compound of claim 37, wherein at least one internucleoside linkage is a phosphorothioate internucleoside linkage.

40. The compound of claim 37, wherein the modified nucleobase is a 5-methylcytosine.

41. The compound of claim 37 wherein at least one of the modified sugars is a bicyclic sugar.

42. The compound of claim 26, consisting of a single-stranded oligonucleotide.

43. A composition comprising the modified oligonucleotide of claim 26 or a salt thereof and a pharmaceutically acceptable carrier or diluent.

* * * * *